US012589115B2

(12) United States Patent
Kranc et al.

(10) Patent No.: US 12,589,115 B2
(45) Date of Patent: Mar. 31, 2026

(54) HAEMATOPOIETIC STEM CELL TREATMENT

(71) Applicant: THE UNIVERSITY COURT OF THE UNIVERSITY OF EDINBURGH, Edinburgh (GB)

(72) Inventors: Kamil Romuald Kranc, London (GB); Dónal O'Carroll, Edinburgh (GB)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 1160 days.

(21) Appl. No.: 17/042,008

(22) PCT Filed: Mar. 29, 2019

(86) PCT No.: PCT/GB2019/050918
§ 371 (c)(1),
(2) Date: Sep. 25, 2020

(87) PCT Pub. No.: WO2019/186191
PCT Pub. Date: Oct. 3, 2019

(65) Prior Publication Data
US 2021/0154236 A1 May 27, 2021

(30) Foreign Application Priority Data
Mar. 29, 2018 (GB) ...................................... 1805287

(51) Int. Cl.
*A61K 35/28* (2015.01)
*A61P 35/02* (2006.01)
*C12N 9/22* (2006.01)
*C12N 15/113* (2010.01)

(52) U.S. Cl.
CPC .............. *A61K 35/28* (2013.01); *A61P 35/02* (2018.01); *C12N 9/22* (2013.01); *C12N 15/113* (2013.01); *C12N 2310/14* (2013.01); *C12N 2310/16* (2013.01); *C12N 2310/20* (2017.05)

(58) Field of Classification Search
CPC .............. A61K 31/711; A61K 31/7115; A61K 31/712; C12N 15/11; C12P 19/34; C12Y 207/07
USPC ..................... 435/6.1, 91.1, 91.31, 455, 458; 514/44 A, 44 E, 44 R; 536/23.1, 24.5
See application file for complete search history.

(56) References Cited

U.S. PATENT DOCUMENTS 5,475,096 A 12/1995 Gold et al.
7,790,039 B2 9/2010 Bosch et al.
2016/0186266 A1* 6/2016 Alarcon ........... G01N 33/57484
702/20

FOREIGN PATENT DOCUMENTS

EP 2 377 559 A1 10/2011
WO WO-00/63364 A2 10/2000
WO WO-00/63364 A3 10/2000
WO WO-2013/176772 A1 11/2013
WO WO-2014/093595 A1 6/2014
WO WO-2018085486 A1 * 5/2018 ........... A61K 31/194

OTHER PUBLICATIONS

Li et al (Oncotarget, vol. 9, No. 3, pp. 3752-3764 (publ. Dec. 2017) (Year: 2017).*
Tudung et al (Genes, Chromosomes and Cancer, vol. 45, pp. 918-932 (2006)). (Year: 2006).*
Roberts et al (Nature Reviews: Drug Discovery, vol. 19, pp. 673-694 (2020)) (Year: 2020).*
See Damase et al (Frontiers in Bioengineering and Biotech., vol. 9, article 628137, pp. 1-24 (2021)) (Year: 2021).*
Shen, X. et al. (Jan. 11, 2021). "YTHDF2 Inhibits Gastric Cancer Cell Growth by Regulating FOXC2 Signaling Pathway," *Frontiers in Genetics* 11:592042.
Vu, L.P. et al. (Nov. 2017). "The N6-methyladenosine (m6A)-forming enzyme METTL3 controls myeloid differentiation of normal hematopoietic and leukemia cells," *Nature Medicine* 23(11):1369-1376.
Zhang, J. et al. (2017). "Knockdown of YTH N⁶-methyladenosine RNA binding protein 2 (YTHDF2) inhibits proliferation and promotes apoptosis in MGC-803 gastric cancer cells," *Chin J Cell Mol Immunol* 33(12):1628-1634. (English Translation of Abstract only).
Zhou, Y. et al. (Mar. 4, 2023). "YTHDF2 exerts tumor-suppressor roles in gastric cancer via up-regulating PPP2CA independently of m⁶A modification," *Biological Procedures Online* 25(1):6.
Agasti et al. "Photocleavable DNA barcode-antibody conjugates allow sensitive and multiplexed protein analysis in single cells," J Am Chem Soc. 134(45):18499-18502, 2012.
Alonso et al., "A rapid and sensitive high-throughput screening method to identify compounds targeting protein-nucleic acids interactions," Nucleic Acids Res. 43(8): e52, 2015.
Ashkenazi et al., "Effective cell-free drug screening protocol for protein-protein interaction," Anal Biochem. 532(53-59, 2017.
Bachas, C. et al. (Apr. 7, 2015). "Gene Expression Profiles Associated with Pediatric Relapsed Aml," PLoS One 10(4):e0121730.
Bak et al., "CRISPR/Cas9 genome editing in human hematopoietic stem cells," Nature Protocols. 13:358-376, 2018.
Bamforth et al., "Cardiac malformations, adrenal agenesis, neural crest defects and exencephaly in mice lacking Cited2, a new Tfap2 co-activator," Nat Genet. 29(4): 469-474, 2001.

(Continued)

*Primary Examiner* — Jane J Zara
(74) *Attorney, Agent, or Firm* — MINTZ, LEVIN, COHN, FERRIS, GLOVSKY AND POPEO, P.C.

(57) ABSTRACT

The present invention relates to modified haematopoietic stem cells, methods for preparing them, and their use in therapy; as well as methods and reagents for expanding haematopoietic stem cells (HSC) and methods for treating haematological disorders. A particular aspect relates to a method for treating a disease or condition characterised by elevated YTHDF2 expression comprising administering to a patient an effective amount of an YTHDF2 inhibitor. Certain aspects of the invention rely on YTFIDF2 protein level or function and use of YTFIDF2 inhibitors.

7 Claims, 14 Drawing Sheets

Specification includes a Sequence Listing.

(56) References Cited

OTHER PUBLICATIONS

Barbieri, I. et al. (Dec. 7, 2017, e-published Nov. 27, 2017). Promoter-bound METTL3 maintains myeloid leukaemia by m 6 A-dependent translation control, Nature 552(7683):126-131.

Chen, G. et al. (2017). "Hepatitis B reactivation in hepatitis B and C coinfected patients treated with antiviral agents: A systematic review and meta-analysis," Hepatology 66(1):13-26.

Chen, J. et al. (2017). "YTH domain family 2 orchestrates epithelial-mesenchymal transition/proliferation dichotomy in pancreatic cancer cells," Cell Cycle 16(23):2259-2271.

Chery, J. "RNA therapeutics: RNAi and antisense mechanisms and clinical applications," Postdoc J 4(7):35-50, 2016.

Crew et al. (2017). "Identification and Characterization of Von Hippel-Lindau-Recruiting Proteolysis Targeting Chimeras (PROTACs) of TANK-Binding Kinase 1," J. Medicinal Chemistry.

De Boer et al., "Transgenic mice with hematopoietic and lymphoid specific expression of Cre," Eur J Immunol. 33(2): 314-325, 2003.

Desrosiers et al., "Identification of methylated nucleosides in messenger RNA from Novikoff hepatoma cells," Proc Natl Acad Sci U S A. 71(10): 3971-3975, 1974.

Dohner et al., "Acute Myeloid Leukemia," N Engl J Med. 373(12): 1136-1152, 2015.

Dominissini et al. "Topology of the human and mouse m6A RNA methylomes revealed by m6A-seq," Nature. 485(7397): 201-206, 2012.

Drabkin et al. "Quantitative HOX expression in chromosomally defined subsets of acute myelogenous leukemia," Leukaemia. 16(2): 186-195, 2002.

Du, H. et al. (Aug. 25, 2016). "YTHDF2 destabilizes m(6)A-containing RNA through direct recruitment of the CCR4-NOT deadenylase complex," Nature Communications 7(1):12626.

Egholm et al. PNA hybridizes to complementary oligonucleotides obeying the Watson-Crick hydrogen-bonding rules Nature. 365:566, 1993.

Elbashir et al., "Duplexes of 21-nucleotide RNAs mediate RNA interference in cultured mammalian cells," Nature. 411:494-98, 2000.

Eppert et al., "Stem cell gene expression programs influence clinical outcome in human leukemia," Nat Med 17:1086-1093, 2011.

Fire et al., "Potent and specific genetic interference by double-stranded RNA in Caenorhabditis," Nature. 391:806, 1998.

Guitart et al., Blood. "Hif-2α is not essential for cell-autonomous hematopoietic stem cell maintenance," 122(10): 1741-1745, 2013.

Guitart et al., "Fumarate hydratase is a critical metabolic regulator of hematopoietic stem cell functions," J Exp Med. 214(3): 719-735, 2017.

Guo et al., "Antagonism of PPAR-γ signaling expands human hematopoietic stem and progenitor cells by enhancing glycolysis," Nat Med. 24(3): 360¬367, 2018.

Haferlach, C. et al. (Oct. 2009). "AML with mutated NPM1 carrying a normal or aberrant karyotype show overlapping biologic, pathologic, immunophenotypic, and prognostic features," Blood 114(14):3024-3032.

Haferlach, T. et al. (May 20, 2010). "Clinical utility of microarray-based gene expression profiling in the diagnosis and subclassification of leukemia: report from the International Microarray Innovations in Leukemia Study Group," 28(15):2529-2537.

Hamilton et at, "A Species of Small Antisense RNA in Post-transcriptional Gene Silencing in Plants," Science. 286:950-951, 1999.

Hanoun et al., "Acute myelogenous leukemia-induced sympathetic neuropathy promotes malignancy in an altered hematopoietic stem cell niche," Cell Stem Cell. 15(3): 365-375, 2014.

Herzog et al., "Thiol-linked alkylation of RNA to assess expression dynamics," Nat Methods 14:1198-1204, 2017.

Horwitz et al., "Umbilical cord blood expansion with nicotinamide provides long-term multilineage engraftment," J Clin Invest. 124(7): 3121-3128, 2014.

Ichihara et al. (2007) "Thermodynamic instability of siRNA duplex is a prerequisite for dependable prediction of siRNA activities," Nucleic Acids Res., 35(18): 123e.

International Search Report mailed on Jun. 7, 2019, for PCT Application No. PCT/GB2019/050918, filed Mar. 29, 2019, 5 pages.

Ivanova et al., The RNA m6A Reader YTHDF2 Is Essential for the Post-transcriptional Regulation of the Maternal Transcriptome and Oocyte Competence, Mol Cell. 67(6): 1059-1067 e1054, 2017.

Karvela et al., "ATG7 regulates energy metabolism, differentiation and survival of Philadelphia-chromosome-positive cells," Autophagy. 12(6): 936-948, 2016.

Klein, H-U. et al. (Dec. 15, 2009). "Quantitative comparison of microarray experiments with published leukemia related gene expression signatures," BMC Bioinformatics 10:422.

Kondo, M. et al. (2003). "Biology of hematopoietic stem cells and progenitors: implications for clinical application," Annu Rev Immunol 21:759-806.

Kranc et al. "Cited2 is an essential regulator of adult hematopoietic stem cells," Cell Stem Cell. 5(6): 659-665, 2009.

Kranc et al., "Transcriptional coactivator Cited2 induces Bmi1 and Mel18 and controls fibroblast proliferation via Ink4a/ARF," Mol Cell Biol. 23(21): 7658-7666, 2003.

Kroon et al., "Hoxa9 transforms primary bone marrow cells through specific collaboration with Meis1a but not Pbx1b" EMBO J. 17(13): 3714-3725, 1998.

Kuhn et al., "Inducible gene targeting in mice," Science. 269(5229): 1427-1429, 1995.

Laurenti et al., "CDK6 levels regulate quiescence exit in human hematopoietic stem cells," Cell Stem Cell. 16(3): 302-313, 2015.

Lawrence et al. "Frequent co-expression of the HOXA9 and MEIS1 homeobox genes in human myeloid leukemias," Leukemia. 13(12): 1993-1999, 1999.

Li et al., "Cytoplasmic m6A reader YTHDF3 promotes mRNA translation," Cell Res. 27(3): 444-447, 2017.

Li, J. et al. (Dec. 18, 2017). "Downregulation of N 6-methyladenosine binding YTHDF2 protein mediated by miR-493-3p suppresses prostate cancer by elevating N 6-methyladenosine levels," Oncotarget 9(3):3752-3764.

Lin et al., "The m(6)A Methyltransferase METTL3 Promotes Translation in Human Cancer Cells," Mol Cell 62, 335-345, 2016.

Lin et at. "RNA interference. Policing rogue genes," Nature. 402:128-129, 1999.

Ling, K-W et al. (Apr. 2002). "Ontogeny and genetics of the hemato/lymphopoietic system," Current Opinion in Immunology 14(2):186-191.

Lowenberg et al. "Acute myeloid leukemia," N Engl J Med. 341(14): 1051-1062, 1999.

Lu et al. (2008) "OligoWalk: an online siRNA design tool utilizing hybridization thermodynamics," Nucleic Acids Res., 36:W104-108.

Mandal et al. "Efficient ablation of genes in human hematopoietic stem and effector cells using CRISPR/Cas9," CellStemCell.15(5):643-652, 2014.

Mead et al., "Niche-mediated depletion of the normal hematopoietic stem cell reservoir by Flt3-ITD-induced myeloproliferation," J Exp Med. 214(7): 2005-2021, 2017.

Mehta et al. "Optimizing the CD34 + cell dose for reduced-intensity allogeneic hematopoietic stem cell transplantation," Leukaemia and Lymphoma. 50(9):1434-1441, 2009.

Metzelder, S.K. et al. (Jul. 2015). "NFATc1 as a therapeutic target in FLT3-ITD-positive AML," Leukemia 29(7):1470-1477.

Metzeler, K.H. et al. (Nov. 15, 2008). "An 86-probe-set gene-expression signature predicts survival in cytogenetically normal acute myeloid leukemia," Blood 112(10):4193-4201.

Meyer et al. ", Rethinking m6A Readers, Writers, and Erasers" Annu Rev Cell Dev Biol. 33(319-342, 2017.

Meyer et al., "Comprehensive analysis of mRNA methylation reveals enrichment in 3' UTRs and near stop codons," Cell. 149(7): 1635-1646, 2012.

Mills, K.I. et al. (Jul. 30, 2009). "Microarray-based classifiers and prognosis models identify subgroups with distinct clinical outcomes and high risk of AML transformation of myelodysplastic syndrome," Blood 114(5):1063-1072.

(56) References Cited

OTHER PUBLICATIONS

Miraki-Moud et al., Acute myeloid leukemia does not deplete normal hematopoietic stem cells but induces cytopenias by impeding their differentiation, Proc Natl Acad Sci U S A. 110(33): 13576-13581, 2013.

Mortensen et al., "The autophagy protein Atg7 is essential for hematopoietic stem cell maintenance," J Exp Med. 208(3): 455-467, 2011.

Ng et al., "A 17-gene stemness score for rapid determination of risk in acute leukaemia," Nature. 540(7633): 433-437, 2016.

Nguyen, T.T. et al. (Oct. 2006). "Identification of novel Runx1 (AML1) translocation partner genes SH3D19, YTHDf2, and ZNF687 in acute myeloid leukemia," Genes Chromosomes Cancer 45(10):918-932.

Nikiforow et al. "Dramatic Expansion of HSCs: New Possibilities for HSC Transplants?," Cell Stem Cell. 18(1): 10-12, 2016.

Nirantar et al. "Rapid screening of protein-protein interaction inhibitors using the protease exclusion assay," Biosens Bioelectron. 56(250-257, 2014.

Notta et al., "Distinct routes of lineage development reshape the human blood hierarchy across ontogeny," Science. 351(6269): aab2116, 2016.

Orkin, S.H. et al. (Feb. 22, 2008). "Hematopoiesis: an evolving paradigm for stem cell biology," Cell 132(4):631-644.

Perry et al. "Existence of Methylated Messenger RNA in Mouse L Cells," Cell. 1(1): 37-42, 1974.

Pigazzi, M. et al. (Mar. 2011). "MLL partner genes drive distinct gene expression profiles and genomic alterations in pediatric acute myeloid leukemia: an AIEOP study," Leukemia 25(3):560-563.

Reynolds et al. (2004) "Rational siRNA design for RNA interference," Nature Biotechnol., 22:326-330.

Rubinstein et al., "Processing and cryopreservation of placental/umbilical cord blood for unrelated bone marrow reconstitution," Proc Natl Acad Sci U S A. 92(22): 10119-10122. 1995.

Sarry et al., "Human acute myelogenous leukemia stem cells are rare and heterogeneous when assayed in NOD/SCID/IL2Rγc-deficient mice," J Clin Invest 121:384-395, 2011.

Sinclair et al., "CXCR2 and CXCL4 regulate survival and self-renewal of hematopoietic stem/progenitor cells," Blood. 128(3): 371-383, 2016.

Shi et al., "YTHDF3 facilitates translation and decay of N6-methyladenosine-modified RNA," Cell Res. 27(3): 315-328, 2017.

Stein et al. "Antisense oligonucleotides as therapeutic agents—is the bullet really magical?" Science. 261:1004, 1993.

Tanabe et al., "RNA helicase YTHDC2 promotes cancer metastasis via the enhancement of the efficiency by which HIF-1α mRNA is translated," Cancer Lett. 376(1): 34-42, 2016.

Tanabe et al., "Transcriptional machinery of TNF-α-inducible YTH domain containing 2 (YTHDC2) gene," Gene. 535(1): 24-32, 2014.

Taskesen, E. et al. (Feb. 24, 2011). "Prognostic impact, concurrent genetic mutations, and gene expression features of AML with CEBPA mutations in a cohort of 1182 cytogenetically normal AML patients: further evidence for CEBPA double mutant AML as a distinctive disease entity," Blood 117(8):2469-2475.

Theler, D. et al. (2014). "Solution structure of the YTH domain in complex with N6-methyladenosine RNA: a reader of methylated RNA," Nucleic Acids Research 42(22): 13911-13919.

Tomasson, M.H. et al. (May 1, 2008). "Somatic mutations and germline sequence variants in the expressed tyrosine kinase genes of patients with de novo acute myeloid leukemia," Blood 111(9):4797-4808.

Velasco-Hernandez et al., HIF-1α can act as a tumor suppressor gene in murine acute myeloid leukemia, Blood. 124(24):3597-3607, 2014.

Velasco-Hernandez et al., "Potential Pitfalls of the Mx1-Cre System: Implications for Experimental Modeling of Normal and Malignant Hematopoiesis," Stem Cell Reports. 7(1): 11-18, 2016.

Vukovic et al., "Adult hematopoietic stem cells lacking Hif-1α self-renew normally," Blood. 127(23): 2841-2846, 2016.

Vukovic et al., "Hif-1α and Hif-2α synergize to suppress AML development but are dispensable for disease maintenance," J Exp Med. 212(13):2223-2234, 2015.

Wagner et al. "Phase I/II Trial of StemRegenin-1 Expanded Umbilical Cord Blood Hematopoietic Stem Cells Supports Testing as a Stand-Alone Graft," Cell Stem Cell. 18(1): 144-155, 2016.

Wang et al. "N(6)-methyladenosine Modulates Messenger RNA Translation Efficiency," Cell. 161(6): 1388-1399, 2015.

Wang et al., "Reduced hematopoietic stem cell frequency predicts outcome in acute myeloid leukemia," Haematologica. 102(9): 1567-1577, 2017.

Wang et al. "N6-methyladenosine-dependent regulation of messenger RNA stability," Nature. 505(7481): 117-120, 2014.

Wang et al. "The Wnt/beta-catenin pathway is required for the development of leukemia stem cells in AML," Science. 327(5973): 1650-1653, 2010.

Wei et al., "Methylated nucleotides block 5' terminus of HeLa cell messenger RNA," Cell. 4(4): 379-386 1975.

Written Opinion mailed on Jun. 7, 2019, for PCT Application No. PCT/GB2019/050918, filed Mar. 29, 2019, 6 pages.

Xiao et al., "Nuclear m(6)A Reader YTHDC1 Regulates mRNA Splicing," Mol Cell. 61(4): 507-519, 2016.

Zamore et al., "RNAi: double-stranded RNA directs the ATP-dependent cleavage of mRNA at 21 to 23 nucleotide intervals," Cell, 101:25-33, 2000.

Zhang, C. et al. (Sep. 14, 2017, e-published Sep. 6, 2017). "m6A modulates haematopoietic stem and progenitor cell specification," Nature 549(7671):273-276.

Zhang, S. et al. (Apr. 10, 2017). "The m6A Demethylase ALKBH5 Maintains Tumorigenicity of Glioblastoma Stem-like Cells by Sustaining FOXM1 Expression and Cell Proliferation Program," Cancer Cell 31(4):591-606.e6.

Zhao et al., "Post-transcriptional gene regulation by mRNA modifications," Nat Rev Mol Cell Biol. 18(1): 31-42, 2017.

Zhou, J. et al. (Oct. 22, 2015). "Dynamic m6A mRNA methylation directs translational control of heat shock response," Nature 526(7574):591-594.

Wu De Pei Sun Ai Ning (Jan. 1, 1991). Chapter 5: Hematopoiesis and Immune Reconstruction, Section 1: Hematopoietic Reconstruction in *Clinical Hematopoietic Stem Cell Transplantation*.

Li, Z. et al. (Sep. 2018, e-published Jul. 31, 2018). "Suppression of m6A reader Ythdf2 promotes hematopoietic stem cell expansion," *Cell Research* 28(9):904-917.

Tan, B. et al. (Jan. 2018, e-published Nov. 6, 2017). "Viral and cellular N6-methyladenosine and N6,2'-O-dimethyladenosine epitranscriptomes in the KSHV life cycle," *Nature Microbiology* 3(1):108-120.

Zhong, X. et al. (Nov. 13, 2018). "Circadian Clock Regulation of Hepatic Lipid Metabolism by Modulation of m6A mRNA Methylation," *Cell Reports* 25(7):1816-1828.e4.

Chen, Z. et al., (May 6, 2021) "YTHDF2 is a potential target of AML1/ETO-HIF1α loop-mediated cell proliferation in t(8;21) AML," *Oncogene* 40:3786-3798.

Einstein, J.M. et al. (Aug. 5, 2021). "Inhibition of YTHDF2 triggers proteotoxic cell death in MYC-driven breast cancer," *Molecular Cell* 81(15):3048-3064.

Ogawa, S. et al. (Aug. 2015, e-published May 3, 2015). "Identification of a fusion gene composed of a Hippo pathway gene MST2 and a common translocation partner ETV6 in a recurrent translocation t(8;12)(q22;p13) in acute myeloid leukemia," *Ann Hematol* 94(8):1431-1433.

Paris, J. et al. (Jul. 3, 2019), "Targeting the RNA m6A Reader YTHDF2 Selectively Compromises Cancer Stem Cells in Acute Myeloid Leukemia," *Cell Stem Cell* 25(1):137-148.

Zhang, Z. et al. (Jan. 2024) "RNA m6A reader YTHDF2 facilitates precursor miR-126 maturation to promote acute myeloid leukemia progression," *Genes & Diseases* 11, 382-396.

* cited by examiner

A

B

C

A

B

C

SEQUENCE LISTING

<160> NUMBER OF SEQ ID NOS: 8

<210> SEQ ID NO 1
<211> LENGTH: 579
<212> TYPE: PRT
<213> ORGANISM: Homo sapiens
<300> PUBLICATION INFORMATION:
<308> DATABASE ACCESSION NUMBER: NCBI NP_057342
<309> DATABASE ENTRY DATE: 2019-02-28
<313> RELEVANT RESIDUES IN SEQ ID NO: (1)..(579)

<400> SEQUENCE: 1

```
Met Ser Ala Ser Ser Leu Leu Glu Gln Arg Pro Lys Gly Gln Gly Asn
1               5                   10                  15

Lys Val Gln Asn Gly Ser Val His Gln Lys Asp Gly Leu Asn Asp Asp
            20                  25                  30

Asp Phe Glu Pro Tyr Leu Ser Pro Gln Ala Arg Pro Asn Asn Ala Tyr
        35                  40                  45

Thr Ala Met Ser Asp Ser Tyr Leu Pro Ser Tyr Tyr Ser Pro Ser Ile
    50                  55                  60

Gly Phe Ser Tyr Ser Leu Gly Glu Ala Ala Trp Ser Thr Gly Gly Asp
65                  70                  75                  80

Thr Ala Met Pro Tyr Leu Thr Ser Tyr Gly Gln Leu Ser Asn Gly Glu
                85                  90                  95

Pro His Phe Leu Pro Asp Ala Met Phe Gly Gln Pro Gly Ala Leu Gly
            100                 105                 110
```

-continued

```
Ser Thr Pro Phe Leu Gly Gln His Gly Phe Asn Phe Phe Pro Ser Gly
        115                 120                 125

Ile Asp Phe Ser Ala Trp Gly Asn Asn Ser Ser Gln Gly Gln Ser Thr
    130                 135                 140

Gln Ser Ser Gly Tyr Ser Ser Asn Tyr Ala Tyr Ala Pro Ser Ser Leu
145                 150                 155                 160

Gly Gly Ala Met Ile Asp Gly Gln Ser Ala Phe Ala Asn Glu Thr Leu
                165                 170                 175

Asn Lys Ala Pro Gly Met Asn Thr Ile Asp Gln Gly Met Ala Ala Leu
                180                 185                 190

Lys Leu Gly Ser Thr Glu Val Ala Ser Asn Val Pro Lys Val Val Gly
                195                 200                 205

Ser Ala Val Gly Ser Gly Ser Ile Thr Ser Asn Ile Val Ala Ser Asn
        210                 215                 220

Ser Leu Pro Pro Ala Thr Ile Ala Pro Pro Lys Pro Ala Ser Trp Ala
225                 230                 235                 240

Asp Ile Ala Ser Lys Pro Ala Lys Gln Gln Pro Lys Leu Lys Thr Lys
                245                 250                 255

Asn Gly Ile Ala Gly Ser Ser Leu Pro Pro Pro Ile Lys His Asn
                260                 265                 270

Met Asp Ile Gly Thr Trp Asp Asn Lys Gly Pro Val Ala Lys Ala Pro
        275                 280                 285

Ser Gln Ala Leu Val Gln Asn Ile Gly Gln Pro Thr Gln Gly Ser Pro
        290                 295                 300

Gln Pro Val Gly Gln Gln Ala Asn Asn Ser Pro Pro Val Ala Gln Ala
305                 310                 315                 320

Ser Val Gly Gln Gln Thr Gln Pro Leu Pro Pro Pro Pro Gln Pro
        325                 330                 335

Ala Gln Leu Ser Val Gln Gln Ala Ala Gln Pro Thr Arg Trp Val
        340                 345                 350

Ala Pro Arg Asn Arg Gly Ser Gly Phe Gly His Asn Gly Val Asp Gly
        355                 360                 365

Asn Gly Val Gly Gln Ser Gln Ala Gly Ser Gly Ser Thr Pro Ser Glu
        370                 375                 380

Pro His Pro Val Leu Glu Lys Leu Arg Ser Ile Asn Asn Tyr Asn Pro
385                 390                 395                 400

Lys Asp Phe Asp Trp Asn Leu Lys His Gly Arg Val Phe Ile Ile Lys
                405                 410                 415

Ser Tyr Ser Glu Asp Asp Ile His Arg Ser Ile Lys Tyr Asn Ile Trp
        420                 425                 430

Cys Ser Thr Glu His Gly Asn Lys Arg Leu Asp Ala Ala Tyr Arg Ser
        435                 440                 445

Met Asn Gly Lys Gly Pro Val Tyr Leu Leu Phe Ser Val Asn Gly Ser
    450                 455                 460

Gly His Phe Cys Gly Val Ala Glu Met Lys Ser Ala Val Asp Tyr Asn
465                 470                 475                 480

Thr Cys Ala Gly Val Trp Ser Gln Asp Lys Trp Lys Gly Arg Phe Asp
                485                 490                 495

Val Arg Trp Ile Phe Val Lys Asp Val Pro Asn Ser Gln Leu Arg His
            500                 505                 510

Ile Arg Leu Glu Asn Asn Glu Asn Lys Pro Val Thr Asn Ser Arg Asp
        515                 520                 525

Thr Gln Glu Val Pro Leu Glu Lys Ala Lys Gln Val Leu Lys Ile Ile
```

```
          530              535              540
Ala Ser Tyr Lys His Thr Thr Ser Ile Phe Asp Asp Phe Ser His Tyr
545              550              555              560

Glu Lys Arg Gln Glu Glu Glu Glu Ser Val Lys Lys Glu Arg Gln Gly
              565              570              575

Arg Gly Lys

<210> SEQ ID NO 2
<211> LENGTH: 3073
<212> TYPE: DNA
<213> ORGANISM: Homo sapiens
<300> PUBLICATION INFORMATION:
<308> DATABASE ACCESSION NUMBER: NCBI: NM_016258
<309> DATABASE ENTRY DATE: 2019-03-03
<313> RELEVANT RESIDUES IN SEQ ID NO: (1)..(3073)

<400> SEQUENCE: 2
ctttccaggt gttagtcgaa acctcgtggt gcgaccctgg tcgtcccaaa ccccctaggc      60
cttaatcctg gggcggtggg ggcggggagg ccgtgagcac ggcttccgct cctccaatcc     120
gccagagggc gcagcggccg gcctctccct tcccggggtt cttcgcgccg ggccccttcc     180
gcgtgggtga gtgaatgtga gagtcagcgc tcgcgccgcg cgcgccgccc gcctccgctg     240
ttcggcgctc tgctttaggc ggtggggggc gggcgcgcgc gtaaaagcat agagacgggc     300
attgagctct tgggctagag cgtcgccgag tcggagccgg agcctgagcc gcgcgctgtg     360
tctccgctgc gtccgccgag gcccccgagt gtcagggaca aaagcctccg cctgctcccg     420
cagccggggc tcatctgccg ccgccgccgc gctgaggaga gttcgccgcc gtcgccgccc     480
gtgaggatct gagagccatg tcggccagca gcctcttgga gcagagacca aaaggtcaag     540
gaaacaaagt acaaaatgga tctgtacatc aaaaggatgg attaaacgat gatgattttg     600
aaccttactt gagtccacag gcaaggccca ataatgcata tactgccatg tcagattcct     660
acttacccag ttactacagt ccctccattg gcttctccta ttctttgggt gaagctgctt     720
ggtctacggg gggtgacaca gccatgccct acttaacttc ttatggacag ctgagcaacg     780
gagagcccca cttcctacca gatgcaatgt ttgggcaacc aggagcccta ggtagcactc     840
catttcttgg tcagcatggt tttaatttct ttcccagtgg gattgacttc tcagcatggg     900
gaaataacag ttctcaggga cagtctactc agagctctgg atatagtagc aattatgctt     960
atgcacctag ctccttaggt ggagccatga ttgatggaca gtcagctttt gccaatgaga    1020
ccctcaataa ggctcctggc atgaatacta tagaccaagg gatggcagca ctgaagttgg    1080
gtagcacaga agttgcaagc aatgttccaa aagttgtagg ttctgctgtt ggtagcgggt    1140
ccattactag taacatcgtg gcttccaata gtttgcctcc agccaccatt gctcctccaa    1200
aaccagcatc ttgggctgat attgctagca agcctgcaaa acagcaacct aaactgaaga    1260
ccaagaatgg cattgcaggg tcaagtcttc cgccaccccc gataaagcat aacatggata    1320
ttggaacttg ggataacaag ggtcccgttg caaaagcccc ctcacaggct ttggttcaga    1380
atataggtca gccaacccag gggtctcctc agcctgtagg tcagcaggct aacaatagcc    1440
caccagtggc tcaggcatca gtagggcaac agacacagcc attgcctcca cctccaccac    1500
agcctgccca gctttcagtc cagcaacagg cagctcagcc aacccgctgg gtagcacctc    1560
ggaaccgtgg cagtgggttc ggtcataatg gggtggatgg taatggagta ggacagtctc    1620
aggctggttc tggatctact ccttcagaac cccacccagt gttggagaag cttcggtcca    1680
ttaataacta taacccccaaa gattttgact ggaatctgaa acatggccgg gttttcatca    1740
```

```
ttaagagcta ctctgaggac gatattcacc gttccattaa gtataatatt tggtgcagca    1800
cagagcatgg taacaagaga ctggatgctg cttatcgttc catgaacggg aaaggccccg    1860
tttacttact tttcagtgtc aacggcagtg gacacttctg tggcgtggca gaaatgaaat    1920
ctgctgtgga ctacaacaca tgtgcaggtg tgtggtccca ggacaaatgg aagggtcgtt    1980
ttgatgtcag gtggattttt gtgaaggacg ttcccaatag ccaactgcga cacattcgcc    2040
tagagaacaa cgagaataaa ccagtgacca actctaggga cactcaggaa gtgcctctgg    2100
aaaaggctaa gcaggtgttg aaaattatag ccagctacaa gcacaccact tccatttttg    2160
atgacttctc acactatgag aaacgccaag aggaagaaga agtgttaaa aaggaacgtc     2220 aaggtcgtgg gaaataaaag gcagttctac acagactgca gcaacggttg catctgcata    2280
tcctaagagg aaaaaatgac cttcaagaga attaggactt tttcttaat ttcactgact     2340 tcagagacga ttgcagactt gcagtttaag tattggaatt tcacaaaaga cataggactt    2400
aactggaaaa tgaaaaaaaa aagaaaaaga aaaaactaaa caaaaaatcc ctctaggtag    2460
tttaggtgaa aaatgtccct tttattttgg ctttggttgt gatttcagag cataatgcta    2520 tgttttttttg tctttttact atgttttttcg gattttttaag tccgtaagtg catacagttt   2580
tctctaattt ttaaacccctt tcctcctccc attttgacat ttgcacttgg agaacacttg   2640
agttgtgaag gttttgggca tccaccccag aaagtgggaa tttgattttta tccttccgaa    2700 ctggaagaac atttttatga agaattttttg tctaggagaa tataacagtg ttacccaagg    2760 ttgtgtctttt aagggtggtt cattttctct gaccttttgt tactcaaagt aaagtactag    2820
gagtcctaag aaatgttctg ttcttgtaca ttatactgat taagtcagga ttaatttgat    2880
ttcaaagctg agaacagtgg taaaaactcg tttacagaaa tgcattttgg aagagaaaaa    2940
tactgtaaaa cgtgtcgtga atgtttcttc agtttcttgt tcagccaatg aggaaagggc    3000
attgcctttc tttttaccat taatcacttc tcaataaacg tgagatcctg ttgagcatca    3060
aaaaaaaaaa aaa                                                       3073
```

```
<210> SEQ ID NO 3
<211> LENGTH: 58
<212> TYPE: DNA
<213> ORGANISM: Artificial Sequence
<220> FEATURE:
<223> OTHER INFORMATION: Example of a DNA sequence encoding hairpin
      shRNA

<400> SEQUENCE: 3
ccggtactga ttaagtcagg attaactcga gttaatcctg acttaatcag tattttttg       58

<210> SEQ ID NO 4
<211> LENGTH: 58
<212> TYPE: DNA
<213> ORGANISM: Artificial Sequence
<220> FEATURE:
<223> OTHER INFORMATION: Example of a DNA sequence encoding hairpin
      shRNA

<400> SEQUENCE: 4
ccggcggtcc attaataact ataacctcga ggttatagtt attaatggac cgtttttg        58

<210> SEQ ID NO 5
<211> LENGTH: 58
<212> TYPE: DNA
<213> ORGANISM: Artificial Sequence
<220> FEATURE:
```

```
<223> OTHER INFORMATION: Example of a DNA sequence encoding hairpin
      shRNA

<400> SEQUENCE: 5
ccgggctact ctgaggacga tattcctcga ggaatatcgt cctcagagta gctttttg          58

<210> SEQ ID NO 6
<211> LENGTH: 21
<212> TYPE: RNA
<213> ORGANISM: Artificial Sequence
<220> FEATURE:
<223> OTHER INFORMATION: Single stranded RNAi molecule

<400> SEQUENCE: 6
uacugauuaa gucaggauua a                                                   21

<210> SEQ ID NO 7
<211> LENGTH: 21
<212> TYPE: RNA
<213> ORGANISM: Artificial Sequence
<220> FEATURE:
<223> OTHER INFORMATION: Single stranded RNAi molecule

<400> SEQUENCE: 7
cgguccauua auaacuauaa c                                                   21

<210> SEQ ID NO 8
<211> LENGTH: 21
<212> TYPE: RNA
<213> ORGANISM: Artificial Sequence
<220> FEATURE:
<223> OTHER INFORMATION: Single stranded RNAi molecule

<400> SEQUENCE: 8
gcuacucuga ggacgauauu c                                                   21
```

HAEMATOPOIETIC STEM CELL TREATMENT

FIELD OF THE INVENTION

The present invention relates to modified haematopoietic stem cells, methods for preparing them, and their use in therapy; as well as methods and reagents for expanding haematopoietic stem cells (HSC) and treating haematological disorders.

INTRODUCTION

Haematopoietic stem cells (HSCs) have a unique capacity to self-renew and differentiate into any cell of the hematopoietic system. From this rare cell population, the entire mature hematopoietic system, comprising lymphocytes (B and T cells of the immune system) and myeloid cells (erythrocytes, megakaryocytes, granulocytes and macrophages) is formed and sustained. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies, provides protection against cancer cells, scavenges foreign materials, produces platelets, and the like. The erythroid lineage provides red blood cells, which act as oxygen carriers. As used herein, the term "stem cell" refers to HSCs and not stem cells of other cell types.

Stem cell transplantation can be used to replace a functional hematopoietic system. Allogeneic stem cell transplantation, in which stem cells are sourced from adult donors or cord blood (CB), offers treatment of choice for many diseases, including blood malignancies (such as lymphoma, myeloma and leukaemia), severe immunodeficiencies and bone marrow failures (Horwitz et al., J Clin Invest. 124(7): 3121-3128, 2014, Nikiforow and Ritz, Cell Stem Cell. 18(1): 10-12, 2016). Furthermore, erythrocyte disorders such as thalassaemia and sickle-cell anaemia have been successfully treated by transplantation of allogeneic stem cells. However, the shortage of suitable adult donors, together with low stem cell yield from CB donations, limits the widespread use of stem cell transplantation. This underscores the paramount importance of expanding fully functional multipotent stem cells. Despite the availability of numerous methods for ex vivo expansion of HSCs in culture, these methods remain inadequate for the production of HSCs for transplantation that maintain long-term self-renewal capacity and multilineage differentiation potential. While several studies reported expansion of CB HSCs by using differentiation inhibitors (Horwitz et al., J Clin Invest. 124(7): 3121-3128, 2014, Nikiforow and Ritz, Cell Stem Cell. 18(1): 10-12, 2016, Wagner et al., Cell Stem Cell. 18(1): 144-155, 2016), long-term persistence of the expanded CB HSCs was not fully achieved. Therefore, the expansion of HSCs with long-term self-renewal and multilineage differentiation potential remains an unmet clinical need.

One problem with stem cell transplantation is that it does not restore mature haematopoietic cells immediately after transplantation (Nikiforow and Ritz, Cell Stem Cell. 18(1): 10-12, 2016). Due to the time required to generate mature cells from reinfused stem cells, there is a lag during which the patient remains immunocompromised. One proposed solution has been to expand the purified stem cells ex vivo to generate a cell population having both stem cells and slightly more differentiated cells (i.e. primitive progenitor cells), which would be able to provide both short- and long-term haematopoietic recovery. Efficient means of expanding primitive progenitor cells remain to be identified.

There is a clinical need to provide means for efficiently expanding both stem cells and primitive progenitor cells ex vivo for transplantation purposes. Furthermore, it is also important to protect HSC/progenitor cells and enhance their regenerative potential during ongoing blood malignancy or following chemotherapy.

N6-methyladenosine (m$^6$A) RNA Modification

RNA modifications affect the processing and metabolism of mRNA and thereby regulate gene expression. N6-methyladenosine (m$^6$A) is one of the most abundant and conserved internal mRNA modifications that plays important roles in regulation of gene expression. The m$^6$A-RNA modification has been discovered decades ago (Desrosiers et al., Proc Natl Acad Sci USA. 71(10): 3971-3975, 1974, Perry and Kelley, Cell. 1(1): 37-42, 1974) but due to technical limitations only recently it became possible to map the modification in the yeast and in mammalian transcriptomes through immunoprecipitation with m$^6$A specific antibodies and high-throughput sequencing (Dominissini et al., Nature. 485(7397): 201-206, 2012, Meyer et al., Cell. 149 (7): 1635-1646, 2012). The modification is highly abundant as it constitutes 0.1%-0.4% of all adenosines in mammals (Wei et al., Cell. 4(4): 379-386, 1975). m6A is predominantly present in mRNA near stop codons and 3'-untranslated regions (3'UTR) (Desrosiers et al., Proc Natl Acad Sci USA. 71(10): 3971-3975, 1974, Perry and Kelley, Cell. 1(1): 37-42, 1974, Dominissini et al., Nature. 485(7397): 201-206, 2012, Zhao et al., Nat Rev Mol Cell Biol. 18(1): 31-42, 2017).

The deposition of m$^6$A modification is catalysed by the METTL3, METTL14, and WTAP methyltransferase complexes referred to as 'writers' and removed by demethylases (including FTO and ALKBH5) collectively called 'erasers' (Zhao et al., Nat Rev Mol Cell Biol. 18(1): 31-42, 2017).

The m$^6$A modification is recognised by the YTH domain proteins (including YTHDF1, YTHDF2, YTHDF3, YTHDC1 and YTHDC2) which act as 'readers' of the m$^6$A modification and execute the m$^6$A functions (Meyer and Jaffrey, Annu Rev Cell Dev Biol. 33(319-342, 2017, Zhao et al., Nat Rev Mol Cell Biol. 18(1): 31-42, 2017). The YTH-domain-containing proteins can be nuclear (YTHDC1) and cytoplasmic (YTHDF1-3 and YTHDC2) (Meyer and Jaffrey, Annu Rev Cell Dev Biol. 33(319-342, 2017, Zhao et al., Nat Rev Mol Cell Biol. 18(1): 31-42, 2017). All members contain highly conserved C-terminal YTH-domain which consist of around 145 amino acids with two or three tryptophan residues that form a binding pocket for m$^6$A. YTHDC1 is a nuclear protein with a YTH domain and regulates RNA splicing (Xiao et al., Mol Cell. 61(4): 507-519, 2016). YTHDC2 is a nucleocytoplasmic RNA helicase which primarily binds to noncoding RNAs as well as pre-RNA intronic and intergenic regions (Tanabe et al., Gene. 535(1): 24-32, 2014, Tanabe et al., Cancer Lett. 376(1): 34-42, 2016). YTHDF1, 2 and 3 are paralogous proteins and are mostly present in the cytoplasm (Meyer and Jaffrey, Annu Rev Cell Dev Biol. 33(319-342, 2017, Zhao et al., Nat Rev Mol Cell Biol. 18(1): 31-42, 2017). YTHDF1 is a reader protein that facilitates translation by coupling m$^6$A-modified RNA with translation initiation factors, and does not affect RNA stability (Wang et al., Cell. 161(6): 1388-1399, 2015). YTHDF2 binds RNA predominantly at the 3'UTR and near the stop codon which overlaps with the m⁶A pattern of distribution, and controls RNA decay (Wang et al., Nature. 505(7481): 117-120, 2014). YTHDF3 promotes protein synthesis and mRNA decay through interactions with YTHDF1 and YTHDF2 respectively (Li et al., Cell Res. 27(3): 444-447, 2017, Shi et al., Cell Res. 27(3): 315-328, 2017).

The functions of m⁶A readers in normal and leukaemic stem cell biology remains unexplored.

SUMMARY OF THE INVENTION

In a first aspect, the invention provides a method for treating a disease or condition characterised by elevated YTHDF2 expression in a patient in need thereof, comprising administering to the patient an effective amount of an YTHDF2 inhibitor.

As would be understood by a person skilled in the art this aspect also relates to a YTHDF2 inhibitor for use in a method of treating a patient with a disease or condition characterised by elevated YTHDF2 expression.

In a second aspect, the invention provides an in vitro method for determining whether a YTHDF2 inhibitor test compound has potential as an agent to treat a haematological disorder, comprising determining the effect that the test compound has on the amount or function of YTHDF2 protein expressed in a cell that has been contacted with the test compound, wherein if the test compound causes a decrease in YTHDF2 protein level or function in the contacted cell then the test compound has potential as an agent to treat a haematological disorder.

In a third aspect, the invention provides a method for selecting a compound for use in the treatment of a haematological disorder, comprising determining in an in vitro setting whether the test compound is capable of inhibiting YTHDF2 protein, wherein a test compound that inhibits YTHDF2 protein is selected for use in the treatment of a haematological disorder.

In particular embodiments, the test compound identified from the second or third aspects of the invention can be formulated into a pharmaceutical composition and used in the method of treatment of the first aspect of the invention.

In a fourth aspect, the invention provides a method for selecting a haematological cancer patient for treatment with an YTHDF2 inhibitor comprising, determining whether the patient's cancer cells (i) express elevated YTHDF2 transcript or protein levels relative to a control or normal cell, wherein if YTHDF2 transcript or protein levels in the individual's cells are elevated relative to a control or normal cell the individual is selected for treatment with an YTHDF2 inhibitor.

In a fifth aspect, the invention provides a method for preparing an inactivated YTHDF2 HSC comprising transfecting a HSC with a nucleic acid molecule capable of inactivating the YTHDF2 gene in the HSC.

In a sixth aspect, the invention provides a haematopoietic stem cell characterised in that the cell has been treated to inactivate YTHDF2 gene or YTHDF2 function.

In a seventh aspect, the invention provides a method for the expansion of HSCs comprising culturing the HSC(s) produced according to aspect 6 of the invention so as to expand the HSCs.

In an eighth aspect, the invention provides a method for ex vivo expansion of multipotent hematopoietic cells, comprising culturing multipotent hematopoietic cells in a medium comprising an YTHDF2 inhibitor, wherein said inhibitor is present in an amount effective to produce a cell population to expand said multipotent hematopoietic cells.

In one embodiment, such expanded HSCs have long-term self-renewal and multilineage differentiation potential.

In a ninth aspect, the invention provides a pharmaceutical composition comprising HSCs prepared according to aspects 5, 6, 7 or 8.

In a tenth aspect, the invention provides a YTHDF2 inactivated HSC or a pharmaceutical composition comprising a YTHDF2 inactivated HSC for use in therapy, particularly haematopoietic stem cell transplantation (HSCT). In one embodiment, the YTHDF2 inactivated HSC is produced according to a method of the invention, such as aspects 5, 7 or 8.

It will be understood to those skilled in the art that features, including optional, suitable, and preferred features of any particular aspect of the present invention may, unless stated otherwise, apply as features, including optional, suitable, and preferred features of any other aspect of the present invention.

DETAILED DESCRIPTION OF THE INVENTION

The various aspects and embodiments of the invention arise from the discovery that inactivation of YTHDF2 inhibits AML initiation and propagation in mouse AML models and results in apoptosis of human AML cells. Furthermore, inactivation of YTHDF2 promotes mouse HSC expansion, increases their self-renewal and enhances their capacity to reconstitute the haematopoietic system.

YTHDF2 is the key m⁶A reader responsible for m⁶A-mediated RNA decay. YTHDF2 protein (579 amino acids) consists of two key domains, namely P/Q/N-rich domain (P/Q/N-rich domain; residues 1-400) which binds CNOT (of the CCR4-NOT deadenylase complex) (Du et al., Nat Commun. 7(12626, 2016) and the YTH domain (residues 401-579) responsible for binding to m⁶A of m⁶A-modified transcripts (Wang et al., Nature. 505(7481): 117-120, 2014). YTHDF2 binds m⁶A-modified transcripts through its aromatic cage within its YTH domain (formed by Trp432, Trp486 and Trp491 residues), recruits the CCR4-NOT deadenylase complex) to its P/Q/N-rich domain (Du et al., Nat Commun. 7, article number:12626, 2016), thus triggering RNA deadenylation and subsequent RNA degradation.

The discovery that YTHDF2 inhibition negatively impacts on AML and increases HSC numbers and activity opens the door to a new way of treating AML and other diseases or disorders characterised by aberrant cells that express elevated levels of YTHDF2, such as haematological disorders. The findings open the possibility to employ a new therapeutic paradigm of efficiently targeting LSCs while simultaneously enhancing normal HSC functions in AML. Furthermore, the results pave the way for therapeutic ex vivo HSC expansion for stem cell transplantation purposes, the enhancement of human haematopoietic reconstitution upon transplantation, efficient blood regeneration following chemotherapy or robust HSC maintenance under leukaemic conditions.

Key Definitions

Herein, haematopoietic stem cells (HSCs) are cells of the blood system which have the capacity to self-renew and differentiate into any cell of the hematopoietic system. They are thus multipotent cells. See further discussion in Introduction section. Primitive progenitor cells are one of the products of stem cells. The term "progenitor cell", "primitive progenitor cell" or "early progenitor cell" are used interchangeably herein. It is a biological cell that, like a stem cell, has a tendency to differentiate into a specific type of cell, but is already more specific than a stem cell and is pushed to differentiate into its "target" cell. Progenitor cells are early descendants of stem cells that can differentiate to form one or more kinds of cells. The most important difference between stem cells and progenitor cells is that stem cells can replicate indefinitely, whereas progenitor cells can divide only a limited number of times. Most progenitors are described as oligopotent, they may be compared to adult stem cells. Progenitors are said to be in a further stage of cell differentiation. They are in the "center" between stem cells and fully differentiated cells.

Herein, the term "culture medium" refers to a medium enabling the growth and survival of mammalian cells in vitro. A culture medium for use in the invention may be a cell culture minimum medium (CCMM), which generally comprises a carbon source, a nitrogen source and trace elements. Examples of a CCMM include, but are not limited to, DMEM (Dulbecco's Modified Eagle's Medium), MEM (Minimal Essential Medium), BME (Basal Medium Eagle), RPMI1640, F-10, F-12, alpha MEM (alpha Minimal Essential Medium), GMEM (Glasgow's Minimal Essential Medium), and IMDM (Iscove's Modified Dulbecco's Medium). A culture medium for use in the invention may further contain one or more additives, as is known in the art, for example, an antibiotic, such as penicillin, streptomycin, gentamicin or combinations thereof, amino acids, vitamins, fetal calf serum or a substitute thereof.

Herein, the term "cultured" in reference to cells means a cell population that has been grown in the presence of defined culture medium under controlled environmental conditions, typically in an environment maintained at 37° C., and containing about 21% oxygen and about 5-10% $CO_2$ for mammalian cells. Similarly, the term "culturing" refers to the process of producing an enlarged population of cells by growth of a cell or cells of interest under controlled environmental conditions, typically in an incubator maintained at a set temperature and providing defined concentrations of oxygen and $CO_2$, and optionally other parameters such as humidity, and agitation in a controlled manner at a set rate.

The term "patient" as used herein refers to an animal, such as a mammal or a bird. In a particular embodiment, the patient is a primate, such as a human.

As used herein an agent that inhibits YTHDF2 is also referred to as a YTHDF2 inhibitor.

As used herein, the term "inhibit" refers to reducing or stopping the amount of or function/activity of the protein, e.g. YTHDF2. For example, an inhibitor of YTHDF2 may affect the amount of YTHDF2 protein produced by the cell, e.g. by targeting the transcription or translation of the protein in the cell. Alternatively, it may affect the function of the protein, e.g. by preventing the protein from forming a complex or catalysing a reaction e.g., the ability of YTHDF2 to form a complex with CCR4-NOT; or, the ability of YTHDF2 to interact with $m^6A$, such that the aforementioned amount of protein or level of function of the protein is less than that observed in the absence of the inhibiting compound (e.g. inhibitor). Inhibition may be reversible or irreversible. Such reduction can be complete (100%), or a lesser amount, such as reduced by 99%, 90%, 75%, 50%, 35%, 25%, 15%, 15%, 5% or less.

As used herein, the terms "compound" and "agent" are used interchangeably. The YTHDF2 inhibitor for use in the invention is preferably a small molecule compound, a nucleic acid molecule, such as an RNA inhibitor, or a peptide-based molecule, such as an aptamer.

A "small molecule compound" as used herein, is an organic molecule that is less than about 5 kilodaltons (KDa) in mass. In some embodiments, the small molecule is less than about 3 KDa, or less than about 2 KDA, or less than about 1.5 KDa, or less than about 1 KDa. In some embodiments, the small molecule is less than about 800 daltons (Da), less than about 600 Da, less than about 500 Da, less than about 400 Da, less than about 300 Da, less than about 200 Da, or less than about 100 Da. Often, a small molecule has a mass of at least 50 Da. In some embodiments, a small molecule is non-polymeric. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

Unless otherwise stated, as used herein, the terms "about" or "approximately" when used in conjunction with a stated numerical value or range denotes somewhat more or somewhat less than the stated value or range, to within a range of ±15% of that stated, ±10% of that stated, ±5% of that stated in different embodiments.

As used herein, the term "treatment" (also "treat" or "treating") refers to any administration of a substance that partially or completely alleviates, ameliorates, relives, inhibits, delays onset of, reduces severity of, and/or reduces frequency, incidence or severity of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition. In such case, a subject may receive YTHDF2 inhibitor to eliminate developing and established cancer stem cells, singly or in combination with the relevant cancer treatments (e.g. standard chemotherapies) to eliminate the cancer bulk.

As used herein, the term "effective amount" or "therapeutically effective amount" refers to an amount of an agent which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, an "effective amount" refers to an amount of a therapeutic agent effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease.

An effective amount is commonly administered in a dosing regimen that may comprise multiple unit doses. For any particular therapeutic agent, an effective amount (and/or an appropriate unit dose within an effective dosing regimen) may vary, for example, depending on route of administration, on combination with other agents. Also, a specific effective amount (and/or unit dose) for any particular patient may depend upon a variety of factors including what disorder is being treated; disorder severity; activity of specific agents employed; specific composition employed; age, body weight, general health, and diet of a patient; time of administration, route of administration; treatment duration; and like factors as is well known in the medical arts.

According to a first aspect of the invention there is provided a method for treating a disease, disorder or condition characterised by elevated YTHDF2 expression in a patient in need thereof, comprising administering to the patient an effective amount of an YTHDF2 inhibitor. In a particular embodiment, the YTHDF2 inhibitor is in a pharmaceutical composition comprising at least one pharmaceutically acceptable excipient.

In particular embodiments, the disease, disorder or condition is characterised by cells (aberrant cells) that express increased levels of YTHDF2 mRNA or YTHDF2 protein relative to normal cells, such as haematopoietic cells with respect to a haematological cancer. In a particular embodiment, the YTHDF2 inhibitor targets the YTHDF2 protein which has a sequence disclosed in SEQ ID NO: 1, or one with at least 95% sequence identity thereto.

In the art, the terms disease, disorder or condition are often used interchangeably to refer to a ill-health/malady/illness that can benefit from medical treatment or intervention, and include a disease or symptoms of a disease.

According to: https://www.healthwriterhub.com/disease-disorder-condition-syndrome-whats-the-difference/, the definition of "disease" is: resulting from a pathophysiological response to external or internal factors; the definition of "disorder" is a disruption of the disease to the normal or regular functions in the body or a part of the body; and, the definition of "condition" is an abnormal state of health that interferes with the usual activities of feeling or wellbeing.

Merriam-Webster's dictionary definition of "disease" is: a condition of the living animal or plant body or of one of its parts that impairs normal functioning and is typically manifested by distinguishing signs and symptoms Merriam-Webster's dictionary definition of "condition" is: a usually defective state of health Merriam-Webster's dictionary definition of "disorder" is: an abnormal physical or mental condition.

As used herein, the terms "condition", "disease" or "disorder" are synonymous and can be used interchangeably and cover any and all of the above definitions.

In particular embodiments, the aberrant cells express a clinically statistically significant increase in levels of YTHDF2 mRNA or YTHDF2 protein relative to normal cells.

In particular embodiments, the aberrant cells express at least 1.2-fold, such as at least 1.5-fold, at least 2-, 3-, 4-, 5-, 6-, 7-, 8-, 9-, 10- and 25-fold increased levels of YTHDF2 mRNA or YTHDF2 protein relative to normal cells.

There are various well-known methods for determining the amount of protein or mRNA in a cell. Immunohistochemistry, ELISA, bar-coded antibody or mass spectroscopy methods, such as liquid-chromatography mass spectroscopy (LC-MS) are particularly suitable methods. A digital barcoded antibody is an antibody whereby DNA molecules are attached to the antibody as a barcode. The antibody can be specific for a particular protein (e.g. YTHDF2). To detect distinct proteins, multiple barcoded antibodies can be assayed in parallel and subsequently analysed by DNA sequencing (E.g. see Agasti et al. J Am Chem Soc. 134(45): 18499-18502, 2012).

For mRNA determination, methods involving hybridisation to the target mRNA using a complementary nucleic acid can be employed. Various adaptations of reverse transcription polymerase chain reaction (RT-PCR), such as quantitative PCR or competitive RT-PCR, are suitable quantitative methods for determining the relative amount of a mRNA species in a normal cell versus an aberrant cell. The person skilled in the art is able to employ a suitable method for detection of the amount or protein or mRNA in the cell or cells.

This aspect of the invention is particularly suitable for treating a haematological cancer, such as AML. Thus, according to a particular aspect of the invention there is provided a method for treating a haematological disorder in a patient in need thereof, comprising administering to the patient an effective amount of an YTHDF2 inhibitor. Thus, according to a particular aspect of the invention there is provided a method for treating AML in a patient in need thereof, comprising administering to the patient an effective amount of an YTHDF2 inhibitor.

In a particular embodiment, the patient is identified as having a disease or condition characterised by elevated YTHDF2 expression prior to administration of the inhibitor. Such identification can be carried out according to a variety of methods as described herein.

The invention further provides a compound for decreasing the amount or function of YTHDF2 protein in a cell and a method for decreasing the amount of YTHDF2 in a cell comprising contacting the cell with a YTHDF2 inhibitor. In particular embodiments, the cell is a cell of an animal, preferably of a mammal or a bird. In a particular embodiment, the cell is a primate cell, preferably a human cell. In another embodiment, the method for decreasing the amount or function of YTHDF2 protein in a cell is performed in vitro.

The inventors have found that not only does inhibiting YTHDF2 cause leukaemic cells to die or lose their leukaemic activity but it also promotes expansion of normal (non-leukaemic) HSCs. Accordingly, the invention further provides a method for enhancing in vivo expansion of haematopoietic stem cells in a patient in need thereof, comprising administering to the patient an effective amount of an YTHDF2 inhibitor.

The person skilled in the art would appreciate that any agent that could inhibit YTHDF2, for example at the nucleic acid (e.g. mRNA) or protein level or function, would have utility in the present invention.

In a particular embodiment, the YTHDF2 inhibitor is specific for YTHDF2. By specific is meant that it preferentially affects YTHDF2 over other targets (particularly over the other YTH domain proteins: YTHDF1, YTHDF3, YTHDC1 and YTHDC2) by at least 5-fold, at least 10-fold, at least 20-fold, at least 50-fold or at least 100-fold. As will be appreciated, specific inhibitors are less likely to initiate off-target effects (such as toxic effects) mediated by inhibition of other targets.

In particular embodiments, the amount of the YTHDF2 inhibitor is effective to reduce YTHDF2 protein level, YTHDF2 function, YTHDF2 interactions with the CCR4-NOT complex or YTHDF2 interaction with $m^6A$ mRNA in the cell.

Functional inhibitor agents can be identified on the basis of their ability to induce a down-regulation or inhibition of gene expression and/or down-regulation or inhibition of the activity/function of a transcriptional or translational product thereof (i.e. YTHDF2/YTHDF2). The expression or activity/function is for example reduced or down-regulated to less than 90%, such as less than 80% such as less than 70% for example less than 60%, for example less than 50%, such as less than 40%, such as less than 30% such as less than 20% for example less than 10%, for example less than 5%, such as completely inhibited (0%) relative to the expression or activity in the absence of the agent that inhibits YTHDF2.

A new approach to protein inhibition called proteolysis targeting chimeras (PROTAC) involving the use of small bi-functional molecules that can inhibit a protein via the induction of its degradation (see Crew et al., J. Medicinal Chemistry. DOI: 10.1021/acs.jmedchem.7b00635, 2017). Thus, in one particular embodiment, the YTHDF2 inhibitor for use in the invention is a PROTAC molecule that inhibits YTHDF2 via the induction of its degradation.

Nucleic acid compounds are another class of therapeutic compounds that can be used to inhibit YTHDF2, by targeting the YTHDF2 gene product, especially YTHDF2 mRNA. Nucleic acid compounds are typically oligomeric and include nucleotide sequences at least partially complementary to a target nucleic acid of interest (e.g. YTHDF2 mRNA) which alter the amount of the produced target protein both in vitro and in vivo. When delivered to a cell containing a target nucleic acid (such as mRNA), nucleic acid compounds have been shown to modulate the expression of the target resulting in altered transcription or translation of the target nucleic acid. In certain instances, the oligomeric compound can reduce the expression of the gene by inhibiting the nucleic acid target and/or triggering the degradation of the target nucleic acid. An example of such nucleic acid oligomeric compounds is the aptamer, a class of high-affinity nucleic acid ligands that specifically bind a desired target molecule (see U.S. Pat. No. 5,475,096).

If the target nucleic acid is mRNA, one mechanism by which an expression-inhibiting oligomeric compound can modulate the expression of the mRNA target is through RNA interference. RNA interference refers to the process of sequence-specific post-transcriptional gene silencing in animals mediated by short interfering RNAs (siRNAs) (e.g. Zamore et al., Cell, 101:25-33, 2000; Fire et al., Nature. 391:806, 1998; Hamilton et al., Science. 286:950-951, 1999; Lin et al., Nature. 402:128-129, 1999; and Elbashir et al., Nature. 411:494-98, 2000). The types of synthetic RNA or RNA-like molecules that can trigger the RNAi response mechanism may be comprised of modified nucleotides and/or one or more non-phosphodiester linkages. In a particular embodiment, the RNAi molecule targets the sequence disclosed in SEQ ID NO: 2, or one with at least 95% sequence identity thereto.

Additionally, single-stranded RNA and RNA-like molecules, which can also include modified nucleotides and have one or more non-phosphodiester linkages, can also alter the expression of a target nucleic acid, such as a target mRNA. These molecules are termed antisense oligonucleotides (ASO). In a particular embodiment, the ASO molecule targets the sequence disclosed in SEQ ID NO: 2, or one with at least 95% sequence identity thereto.

Presently there are many different nucleic acid molecules that can inhibit translation of an mRNA and/or decrease the stability of the RNA. The RNA inhibitor is preferably an RNAi molecule specific for YTHDF2 mRNA or an antisense oligonucleotide (ASO) specific for YTHDF2 mRNA. In this context, specific means that the molecule does not significantly binds to any other mRNA.

Thus, according to another embodiment, the YTHDF2 inhibitor is or comprises a nucleic acid molecule capable of inhibiting mRNA of YTHDF2. In a particular embodiment, the nucleic acid inhibiting molecule targets the sequence disclosed in SEQ ID NO: 2, or one with at least 95% sequence identity thereto.

For a review of RNA therapeutics, see J Chery (Postdoc J 4(7):35-50, 2016).

The term "RNA interference" or "RNAi" refers generally to RNA-dependent silencing of gene expression initiated by double stranded RNA (dsRNA) molecules in a cell's cytoplasm. The dsRNA molecule reduces or inhibits transcription products of a target nucleic acid sequence, thereby silencing the gene or reducing expression of that gene. Thus, the term "RNA interference molecule" or "RNAi molecule" refers to a molecule that is capable of eliciting "RNA interference" or "RNAi".

RNA interference (RNAi) molecules include short interfering RNA (siRNA), short hairpin RNA (shRNA) and micro RNA (miRNA) molecules. These are an RNA duplex of nucleotides that target to mRNA of a sequence of interest, The RNA duplex portion can be part of a hairpin structure (such as with shRNA). Having bound to a target mRNA it induces an enzymatic degradation reaction leading to destruction of the mRNA, which is then no longer available for translation into the protein. RNA interference is therefore a type of sequence-specific post-transcriptional gene silencing through inhibition of gene expression. The technique of gene-silencing is sometimes called knock-down. It causes a reduction in gene expression. The term reduced, as used herein indicates that the target gene expression is reduced by 1-100%.

The RNAi molecules of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Methods and algorithms to predict nucleotide sequences that are likely to be effective at RNAi-mediated silencing (or antisense oligonucleotide silencing, see later) of a target gene are known in the art. Non-limiting examples of such methods and algorithms include "i-score", described by Ichihara et al. (2007) Nucleic Acids Res., 35(18): 123e; "Oligowalk", publicly available at rna.urmc.rochester.edu/servers/oligowalk and described by Lu et al. (2008) Nucleic Acids Res., 36:W104-108; and "Reynolds score", described by Khovorova et al. (2004) Nature Biotechnol., 22:326-330. RNAi technologies are suitably advanced that the person skilled in the art would be able to make an RNAi molecule that could inhibit YTHDF2 mRNA.

Examples of three hairpin RNAi molecules that can inhibit YTHDF2 mRNA are those encoded by SEQ ID NO: 3, 4 or 5. When these sequences are transduced into a cell using a suitable viral vector the encoded RNAi hairpin sequences are produced. These small hairpin RNAs (shRNA) molecules are sequences of RNA, that include a region of internal hybridization that creates a hairpin structure. shRNA molecules are processed within the cell to form siRNA which in turn knock down gene expression.

Shorter linear RNAi molecules (within these hairpin sequences) which could be transduced directly into a cell to effect transient knockdown of YTHDF2 have the sequences disclosed in SEQ ID NO: 6-8. The The RNAi sequence in SEQ ID NO: 3 (underlined) is disclosed in SEQ ID NO: 6. The RNAi sequence in SEQ ID NO: 4 (underlined) is disclosed in SEQ ID NO: 7. The RNAi sequence in SEQ ID NO: 5 (underlined) is disclosed in SEQ ID NO: 8.

```
                                        (SEQ ID NO: 3)
CCGGTACTGATTAAGTCAGGATTAACTCGAGTTAATCCTGACTTAATCAG
TATTTTTG-3';

(SEQ ID NO: 4)
5'-CCGGCGGTCCATTAATAACTATAACCTCGAGGTTATAGTTATTAATG
GACCGTTTTTG-3';

(SEQ ID NO: 5)
5'-CCGGGCTACTCTGAGGACGATATTCCTCGAGGAATATCGTCCTCAGA
GTAGCTTTTTG-3';

(SEQ ID NO: 6)
UACUGAUUAAGUCAGGAUUAA;

(SEQ ID NO: 7)
CGGUCCAUUAAUAACUAUAAC;

(SEQ ID NO: 8)
GCUACUCUGAGGACGAUAUUC.
```

In particular embodiments, the RNAi molecule for use in the present invention is one having a sequence as disclosed in any of SEQ D Nos: 3-8.

Surprisingly, only a few molecules of RNAi are required to block gene expression which implies the mechanism is catalytic. The site of action appears to be nuclear as little if any RNAi is detectable in the cytoplasm of cells indicating that RNAi exerts its effect during mRNA synthesis or processing. RNAi molecules as large as 1000 bp derived from coding sequence are effective inhibitors of gene expression.

Accordingly, an RNAi molecule for use in the invention will typically have a size from 10-1000 nucleobases (nb), such as from 12-500, from 12-100 nb, or from 12-35 nb in length.

The invention also provides an isolated RNAi molecule having about 12-100 bases, such as about 15-35 bases, wherein the RNAi molecule comprises a continuous stretch of at least 7 bases that is complementary to and capable of hybridizing to a continuous stretch of at least 7 bases that is complementary to and capable of hybridizing to YTHDF2 mRNA. In particular embodiments, the isolated RNAi molecule comprises a sequence disclosed in any of SEQ ID Nos: 3-5.

Antisense technology is another effective way to reduce the expression of a specific gene product. An antisense oligonucleotide (ASO) is a short single stranded oligonucleotide molecule that is capable of hybridising to a target mRNA of interest. Once bound it reduces the ability of that mRNA to be used for translation, such as via steric interference and other mechanisms.

ASO molecules typically comprise 8-35, such as 12-30, linked nucleosides that comprise a nucleobase sequence capable of hybridising the target mRNA sequence of interest. In order to minimise off-target hybridisation, the target complementary/hybridising portion is generally at least 8 nucleobases in length.

The antisense oligonucleotides are typically modified at one or more of the sugar moieties, the bases and/or the internucleotide linkages as well as the phosphate moieties. For example, the modifications of the oligonucleotides comprise modifications such as phosphorothioate (S-ODN) internucleotide linkages, methylphosphonate internucleotide linkages, phosphoramidate linkages, peptide linkages, 2'-O-alkyl modifications of the sugar, in particular methyl, ethyl, propyl, butyl and the like, 2'-methoxyethoxy modifications of the sugar and/or modifications of the bases. The various modifications may be combined in one oligonucleotide. These modifications serve to increase such properties as: the stability and binding of the molecule to the target, reduced degradation (hence increased half-life), increased cellular uptake, increased binding affinity, and the like.

Certain antisense compounds having a gapmer motif (wing:gap:wing) wherein an internal "gap" region having a plurality of nucleotides that supports RNaseH cleavage is positioned between external "wing" regions having a plurality of nucleotides that are chemically distinct from the nucleosides of the internal region. In certain embodiments, the regions of a gapmer are differentiated by the types of sugar moieties comprising each distinct region. The types of sugar moieties that are used to differentiate the regions of a gapmer may in some embodiments include 3-D-ribonucleosides, β-D-deoxyribonucleosides, 2'-modified nucleosides (such 2'-modified nucleosides may include 2'-MOE and 2'-0-CH3, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl (cEt) or linked nucleic acid (LNA).

Antisense oligonucleotides may be administered in the form of single-stranded, double-stranded, circular or hairpin and may contain structural elements such as internal or terminal bulges or loops. Once administered, the antisense oligonucleotides may elicit the action of one or more enzymes or structural proteins to effect modification of the target nucleic acid.

ASOs; like RNAi molecules; can be introduced into cells using transfection or transduction according to well-known methods. A suitable reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide. Electroporation can also be used to introduce ASOs into cells.

As used herein, the term "oligonucleotide" refers to an oligomer or polymer of RNA or DNA or mimetics, chimeras, analogs and homologs thereof. This term includes oligonucleotides composed of naturally occurring nucleobases; sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

Phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage.

ASOs can be made in vitro using enzymatic or chemical synthetic methods such as those described WO 00/63364.

The person skilled in the art is able to design and make an ASO capable of inhibiting YTHDF2 mRNA.

Agents that decrease expression of YTHDF2 include non-enzymatic nucleic acid molecules that binds to target RNA by means of RNA-RNA or RNA-DNA or RNA-PNA (protein nucleic acid; Egholm et al., Nature. 365:566, 1993) interactions and alters the activity of the target RNA (for a review see Stein and Cheng, Science. 261:1004, 1993) as well as enzymatic nucleic acid agents. Merely by way of example, a suitable embodiment of an agent that decreases expression of YTHDF2 may be selected from the group consisting of: agents for use in RNA interference (RNAi), including small interfering RNA (siRNA) molecules that inhibit YTHDF2 expression; antisense oligonucleotides that inhibit YTHDF2 expression; and ribozymes that inhibit YTHDF2 expression. Suitable antisense oligonucleotides may be designed with reference to the previously published sequences of nucleic acids, such as mRNA, that encode YTHDF2. Suitable examples of siRNA molecules that may be used as agents that decrease expression of YTHDF2, and which may be employed in the methods or uses of the invention, may be commercially available siRNA molecules that inhibit YTHDF2 expression. Merely by way of example, suitable siRNA molecules include those in Example 12 herein (see also FIGS. 6H, I and J).

An enzymatic nucleic acid molecule is one that has complementarity in a substrate binding region to a specified gene target (e.g. YTHDF2), and also has an enzymatic activity which is active to specifically cleave target RNA Such that the enzymatic nucleic acid molecule is able to intermolecularly cleave RNA and thereby inactivate a target RNA molecule. The complementary regions allow sufficient hybridization of the enzymatic nucleic acid molecule to the target RNA and thus permit cleavage. One hundred percent complementarity is preferred, but complementarity as low as 50-75% may also be useful in this invention. The nucleic acids may be modified at the base, sugar, and/or phosphate groups. The term enzymatic nucleic acid molecule is used interchangeably with phrases such as enzymatic nucleic acid, ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. Any of these types of molecule can be used as a YTHDF2 inhibitor in the invention.

In other embodiments, the agent that inhibits YTHDF2 is a nucleic acid or peptide-based aptamer.

Aptamer technology started in the early 1990s and has advanced to the stage where therapeutics have now been approved (e.g. FDA approved pegaptanib for age-related macular degeneration in 2004). The person skilled in the art would be able to design a nucleic acid or peptide-based aptamer against YTHDF2.

In particular embodiment, the YTHDF2 inhibitor molecule is selected from the group consisting of small molecule compound, RNA interference (RNAi), antisense oligonucleotide (ASO), and nucleic acid and peptide-based aptamer. As noted above, the YTHDF2 inhibitor for use in the method of treatment or medical uses described herein can be present in a pharmaceutical composition comprising at least one pharmaceutically acceptable excipient.

YTHDF2 is known as: YTH N6-Methyladenosine RNA binding protein 2. Synonyms for YTHDF2 Include CAHL, HGRG8, and NY-REN-2. The gene and protein sequences for YTHDF2 (from various animals including human) are known and available from various gene sequence databases such as Ensembl, GenBank, and UniProt. Human YTHDF2 protein sequence can be found in NCBI ACCESSION: NP_057342 (and SEQ ID NO: 1); and the YTHDF2 mRNA transcript can be found in NCBI ACCESSION: NM_016258 (and SEQ ID NO: 2).

The person skilled in the art is able to design nucleic-acid based molecules capable of hybridising to and inhibiting the YTHDF2 mRNA transcript sequence disclosed herein.

A disease, disorder or condition characterised by elevated YTHDF2 expression include haematological disorders and cancers, genitourinary or gynecologic cancers, breast cancer, melanoma and lung adenocarcinoma. Examples of suitable genitourinary or gynecologic cancers include: testicular germ cell cancer, uterine endometrial cancer, cervical squamous cell carcinoma and ovarian cancer. Examples of suitable haematological disorders include blood cancers such as acute lymphocytic leukaemia (AML), chronic lymphocytic leukaemia (CLL), diffuse large B-cell lymphoma (DLBCL), T-cell acute lymphoblastic leukaemia (T-ALL) and B-cell acute lymphoblastic leukaemia (B-ALL).

In particular embodiments, the disease, condition or disorder is selected from the group consisting of: a haematological disorder, a genitourinary or gynecologic cancer, breast cancer, melanoma and lung adenocarcinoma. Examples of suitable genitourinary or gynecologic cancers include: testicular germ cell cancer, uterine endometrial cancer, cervical squamous cell carcinoma and ovarian cancer.

In particular embodiments, the disease, condition or disorder is selected from the group consisting of: AML, CLL, DLCL, T-ALL, B-ALL, breast cancer, melanoma cancer, lung cancer, testicular germ cell cancer, uterine endometrial cancer, cervical squamous cell carcinoma and ovarian cancer. In a particular embodiment, the disease is AML. Given that currently available chemotherapies often fail to fully eradicate LSCs in AML, YTHDF2 serves as an excellent candidate therapeutic target to eliminate LSCs. Furthermore, as chemotherapies cause myelosuppression, inhibition of YTHDF2 offers an opportunity to enhance normal HSC functions and boost haematopoietic regeneration during AML treatment regimens.

Acute myeloid leukaemia (AML) is a blood cancer characterised by an over-proliferation of primitive myeloid progenitors, referred to as blasts, which display a differentiation block (Dohner et al., N Engl J Med. 373(12): 1136-1152, 2015). One of the most prominent symptoms of AML is the suppression of normal haematopoiesis or BM failure. AML is an aggressive clonal disorder of haematopoietic stem and progenitor cells (HSPCs), in which the acquisition of mutations by HSPCs results in a block in their myeloid differentiation, and the generation of self-renewing pre-leukaemic stem cells that eventually form treatment-resistant leukaemic stem cells (LSCs, also referred to as leukaemia-initiating cells) (Dohner et al., N Engl J Med. 373(12): 1136-1152, 2015). Contrary to normal stem cell and primitive progenitor cells, LSCs are characterised by an uncontrolled self-renewal capacity and impaired differentiation potential and have the ability to initiate and propagate leukaemia. Current conventional therapies used to treat patients have remained essentially unchanged for 4 decades (Dohner et al., ibid). While they effectively target the bulk AML population, they often fail to fully eradicate LSCs. The surviving population of LSCs contributes to minimal residual disease, ultimately causing often fatal disease relapses. Overall 5-year survival rate in AML is only 30-40%. Thus, in a significant number of patients, AML will ultimately relapse in a form that is resistant to chemotherapy treatment. Due to the lack of effective therapies and poor survival outcomes, AML remains an unmet clinical need. It is of immense importance to identify therapies which specifically target LSCs.

In blood malignancies such as leukaemias, malignant cells disrupt the bone marrow (BM) microenvironment and compromise HSC functions (Miraki-Moud et al., Proc Natl Acad Sci USA. 110(33): 13576-13581, 2013, Hanoun et al., Cell Stem Cell. 15(3): 365-375, 2014, Mead et al., J Exp Med. 214(7): 2005-2021, 2017). Furthermore, it has been shown that HSC depletion correlates with the aggressive blood malignancy progression (Wang et al., Haematologica. 102(9): 1567-1577, 2017). The collapse of haematopoiesis is frequently manifested by bleeding, anaemia and severe infections, which significantly contribute to morbidity and mortality of leukaemia patients (Lowenberg et al., N Engl J Med. 341(14): 1051-1062, 1999). It is therefore of a major clinical importance to enhance HSC functions and boost normal haematopoiesis during the course of AML. The inventors have found that inhibiting YTHDF2 results in normal HSC and progenitor cell expansion and enhances their activity upon stress. See Examples 2, 3, 4 and 7 herein.

According to another aspect of the invention there is provided a method to boost normal haematopoiesis during the course of leukaemogenesis in AML patients comprising administering to a patient in need thereof a YTHDF2 inhibitor.

In addition to killing LSC, the YTHDF2 inhibitor also increases in vivo expansion of the patient's HSCs. In effect, the YTHDF2 inhibitor serves to treat the disease (e.g. AML) in patients via these two mechanisms (i) kill cancer cells (e.g. LSCs) and (ii) expansion of the patient's normal HSCs.

Administration of a YTHDF2 inhibitor is expected to reduce the number of LSC in the body. One current issue with conventional chemotherapy in AML patients is that of residual LSC survival, which typically result in regression of a chemotherapy resistant form of the disease. The present invention, offers a new way of treating AML patients, whereby the patient is treated with a YTHDF2 inhibitor, optionally in addition to receiving chemotherapy. Without wishing to be bound by theory, the proposed way of treatment is likely to eliminate the bulk AML cells (through standard chemotherapy), and through inhibiting YTHDF2 an reduction or elimination AML-causing LSCs while simultaneously enhancing the regenerative capacity of normal HSCs.

According to one aspect of the invention there is provided a method for reducing the number of LSC in a patient suffering from AML comprising administering to the patient a therapeutically effective amount of a YTHDF2 inhibitor. In one embodiment, the YTHDF2 inhibitor is administered in a pharmaceutical composition comprising at least one pharmaceutically acceptable excipient. In another embodiment, the YTHDF2 inhibitor is administered in combination with chemotherapy.

Currently available chemotherapies used as cancer treatment regimens are particularly cytotoxic to stem and progenitor cells, resulting in their exhaustion and myelosuppression. Given that current cancer therapies fail to protect normal haematopoietic cells, a major clinical need is to minimise the negative impact of chemotherapies on the haematopoietic system. It is therefore of major importance to identify strategies whereby chemotherapy induced bone marrow cytotoxicity is mitigated and the regenerative potential of stem/progenitor cells is boosted.

According to one aspect of the invention there is provided a method for protecting the bone marrow from the toxic effects of chemotherapy comprising administering to the patient a therapeutically effective amount of a YTHDF2 inhibitor prior to chemotherapy. In this context, protecting mean reducing the toxic effect that chemotherapy has on the bone marrow, in particular the haematopoietic cells in the bone marrow. A measure of whether the YTHDF2 inhibitor protects the bone marrow in this fashion is how quickly the haematopoietic cells return to normal or near normal following chemotherapy. In one embodiment, the YTHDF2 inhibitor is administered in a pharmaceutical composition comprising at least one pharmaceutically acceptable excipient.

As would be understood by a person skilled in the art that the method of treatment aspects also relate to a YTHDF2 inhibitor for use in therapy, particularly for use in a method of treating a patient with a disease or condition characterised by elevated YTHDF2 expression. The method involving administering a pharmaceutically effective amount of the YTHDF2 inhibitor, or a pharmaceutical composition comprising it, to a patient in need thereof.

As noted above, the YTHDF2 inhibitor can be any molecule that blocks production of YTHDF2 protein in a cell or interferes with the normal function of the YTHDF2 protein, such as impeding the interaction of YTHDF2 with CCR4-NOT complex or YTHDF2 interaction with $m^6A$.

In a particular embodiment, the amount of the YTHDF2 inhibitor is effective to reduce YTHDF2 protein level, YTHDF2 function, YTHDF2 interactions with the CCR4-NOT complex or YTHDF2 interaction with $m^6A$ mRNA in the cell.

In particular embodiments, the inhibitor is a small chemical compound or a nucleic-acid based molecule.

The invention also provides a YTHDF2 inhibitor for use in a method of treating a patient with a haematological cancer. For example, wherein a pharmaceutically effective amount of the YTHDF2 inhibitor or a pharmaceutical composition containing it is administered to a patient suffering from a haematological disorder.

The invention also provides a YTHDF2 inhibitor for use in a method for enhancing in vivo expansion of haematopoietic stem cells in a patient in need thereof.

The inventors have found that HSCs lacking YTHDF2 have enhanced responses to 5-fluorouracil. This suggests that the combined use of a YTHDF2 inhibitor and chemotherapy would be beneficial in the treatment of AML and other haematological diseases.

Thus, the invention also provides a YTHDF2 inhibitor for use in a method of treating a patient with a haematological cancer, wherein the method also involves treating the patient with chemotherapy or radiotherapy.

An individual who is "suffering from" a disease, disorder, and/or condition has been diagnosed with and/or displays one or more symptoms of the disease, disorder, and/or condition. When referred to herein, an individual who is suffering from a disease (e.g. cancer) is also one who has the disease (e.g. cancer) or one who is in need of treatment for the disease (e.g. cancer).

Pharmaceutical Compositions of a YTHDF2 Inhibitor

As noted above, an YTHDF2 inhibitor of the invention can be incorporated into pharmaceutical compositions suitable for administration, for example, in accordance with the methods of treatment or medical uses described herein.

Thus, according to another aspect of the invention there is provided a pharmaceutical composition comprising an YTHDF2 inhibitor and at least one therapeutically acceptable excipient. In one embodiment, the YTHDF2 inhibitor is a small molecule compound or a nucleic acid based molecule, such as an RNAi molecule. In one embodiment, the nucleic acid based inhibitor molecule is a nucleic acid molecule capable of inhibiting mRNA of YTHDF2.

Pharmaceutical compositions typically comprise the agent/compound and a pharmaceutically acceptable excipient. The term "pharmaceutically-acceptable excipient" as used herein refers to an ingredient in a pharmaceutical formulation, other than an active ingredient, which is non-toxic to a subject. A pharmaceutically acceptable excipient includes, but is not limited to, a buffer, carrier, additive, stabilizer, or preservative. It may comprise one or more compatible solid or liquid fillers, diluents or encapsulating substances that are suitable for administration into a human. The term "excipient" denotes an organic or inorganic ingredient, natural or synthetic, with which the active ingredient is combined to facilitate the application.

Types of suitable excipient are salts, buffering agents, wetting agents, emulsifiers, preservatives, compatible carriers, diluents, carriers, vehicles, supplementary immune potentiating agents such as adjuvants and cytokines that are well known in the art and are available from commercial sources for use in pharmaceutical preparations (see, e.g. Remington: The Science and Practice of Pharmacy with Facts and Comparisons: Drugfacts Plus, $20^{th}$ Ed. Mack Publishing; Kibbe et al., (2000) Handbook of Pharmaceutical Excipients, $3^{rd}$ Ed., Pharmaceutical Press; and Ansel et al., (2004) Pharmaceutical Dosage Forms and Drug Delivery Systems, $7^{th}$ Ed., Lippencott Williams and Wilkins). Optionally, the pharmaceutical compositions contain one or more other therapeutic agents or compounds. Suitable pharmaceutically acceptable excipients are relatively inert and can facilitate, for example, stabilisation, administration, processing or delivery of the active compound/agent into preparations that are optimised for delivery to the body, and preferably directly to the site of action.

The pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

When administered, the pharmaceutical compositions of the present invention are administered in pharmaceutically acceptable preparations/compositions. Such preparations may routinely contain one or more pharmaceutically acceptable "excipients".

Administration may be topical, i.e., substance is applied directly where its action is desired, enteral or oral, i.e., substance is given via the digestive tract, parenteral, i.e., substance is given by other routes than the digestive tract such as by injection. Nucleic acid and peptide-based molecules are typically administered by injection.

Pharmaceutical compositions for parenteral administration (e.g. by injection), include aqueous or non-aqueous, isotonic, pyrogen-free, sterile liquids (e.g. solutions, suspensions), in which the active ingredient is dissolved, suspended, or otherwise provided (e.g. in a liposome or other microparticulate). Such liquids may additionally contain one or more pharmaceutically acceptable excipients, such as anti-oxidants, buffers, stabilisers, preservatives, suspending agents, and solutes that render the formulation isotonic with the blood (or other relevant bodily fluid) of the intended patient. In particular embodiments, the composition may be lyophilised to provide a powdered form that is ready for reconstitution as and when needed. When reconstituted from lyophilised powder the aqueous liquid may be further diluted prior to administration. For example, diluted into an infusion bag containing 0.9% sodium chloride injection, USP, or equivalent, to achieve the desired dose for administration. In particular embodiments, such administration can be via intravenous infusion using an IV apparatus.

The term "parenteral," as used herein, includes intravenous, intramuscular, subcutaneous, rectal, vaginal, and intraperitoneal administration.

Typically, the YTHDF2 inhibitor for intravenous administration is formulated in sterile isotonic aqueous buffer. Where necessary, the compositions can also include a solubilizing agent. Compositions for intravenous administration can optionally include a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule. Where the YTHDF2 inhibitor is to be administered by infusion, it can be dispensed, for example, with an infusion bottle containing sterile pharmaceutical grade water or saline. Where the YTHDF2 inhibitor is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavouring agents such as peppermint, oil of wintergreen, or cherry; colouring agents; and preserving agents, to provide a pharmaceutically palatable preparation. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like.

Compositions for use in accordance with the present invention can be formulated in conventional manner using one or more physiologically acceptable excipients. Thus, the active agent (YTHDF2 inhibitor) and optionally another therapeutic or prophylactic agent and their physiologically acceptable salts and solvates can be formulated into pharmaceutical compositions for administration by inhalation or insufflation (either through the mouth or the nose) or oral, parenteral or mucosal (such as buccal, vaginal, rectal, sublingual) administration. In one aspect, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable excipients (as additives) such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavouring, colouring and sweetening agents as appropriate.

The pharmaceutical compositions of the invention are for administration in an effective amount. An "effective amount" is the amount of a composition that alone, or together with further doses, produces the desired response.

In certain embodiments, the agent that inhibits YTHDF2 can be administered as a pharmaceutical composition in which the pharmaceutical composition comprises between 0.1-1 mg, 1-10 mg, 10-50 mg, 50-100 mg, 100-500 mg, or 500 mg to 5 g of the active agent (YTHDF2 inhibitor).

In particular embodiments, the YTHDF2 inhibitor will be administered at approximately 10, 20, 30, 40, 50, 60, 70, 80, 90, 100 mg/Kg body weight per dose. Other embodiments comprise the administration of the YTHDF2 inhibitor at about 200, 300, 400, 500, 600, 700, 8000, 900, 1000, 1100, 1200, 1300, 1400, 1500, 1600, 1700, 1800, 1900 or 2000 mg/Kg body weight dose. Using the teaching herein, one of skill in the art can determine the effective dose and dosing schedule/regime of the YTHDF2 inhibitor based on preclinical and clinical studies and standard medical and biochemical measurements and techniques.

Pharmaceutical Compositions of a HSC

A population of HSC for administration to a patient in need thereof, e.g. HSCT can be formulated using any suitable pharmaceutical excipients known in the art and according to standard procedures. It is envisaged that most HSC containing pharmaceutical compositions of the invention will be injections, infusions or implants comprising the stem cell compositions of the present invention.

Also provided are compositions including the YTHDF2 inactivated HSC, including pharmaceutical compositions and formulations, such as unit dose form compositions including the number of cells for administration in a given dose or fraction thereof. The pharmaceutical compositions and formulations generally include one or more optional pharmaceutically acceptable excipients. In some embodiments, the composition includes at least one additional therapeutic agent. Suitable pharmaceutically-acceptable excipients for use with HSCs can be the same as for a chemical inhibitor or other agent, such as described herein.

In some embodiments, the choice of excipient is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some embodiments, a mixture of two or more preservatives is used. The preservative or mixtures thereof are typically present in an amount of about 0.0001 to about 2% by weight of the total composition. Excipients are described, e.g., by Remington's Pharmaceutical Sciences 16th edition, Osol, A. Ed. (1980). Pharmaceutically acceptable excipients are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

In some embodiments, buffering agents are included in the compositions. Suitable buffering agents include, for example, citric acid, sodium citrate, phosphoric acid, potassium phosphate, and various other acids and salts. In some embodiments, a mixture of two or more buffering agents is used. The buffering agent or mixtures thereof are typically present in an amount of about 0.001 to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition comprising cells it will generally be formulated in a unit dosage injectable form (solution, suspension, emulsion).

For standard cord blood (CB) stem transplantation, CB units are thawed using standard methods (Rubinstein et al., Proc Natl Acad Sci USA. 92(22): 10119-10122. 1995). HSPCs are CD34 enriched using, e.g. a CliniMACS Cell Selection Device (Miltenyi) or similar, followed by intravenous infusion (Wagner et al., Cell Stem Cell. 18(1): 144-155, 2016).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some embodiments be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise excipients, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavouring agents, and/or colours, depending upon the route of administration and the preparation desired. Standard texts may in some embodiments be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

It will be appreciated by the person skilled in the art that the precise manner of administering to a subject a therapeutically effective amount of a YTHDF2 inhibitor or a YTHDF2-inactivated haematopoietic stem or progenitor cell, or a population thereof, of the invention for treating condition, disease or disorder will be at the discretion of the attending physician. The mode of administration, including the dosage and posology, and the like may be selected based on the severity of the disease and a host of other consideration such as the subject's condition, size, weight sex, age and history. However, as a guide the following information will be useful.

Dosing of Cells

Dose Amount

In some embodiments, the dose of HSC (e.g. YTHDF2 inactivated HSC) administered to a patient is in the range from about $10^5$ to about $10^8$ cells per kilogram body weight of the subject. For example, in some embodiments, the dose includes about $1\times10^5$, or about $2\times10^5$, or about $5\times10^5$, or about $1\times10^6$, or about $5\times10^6$ or about $1\times10^7$ or about $5\times10^7$, or about $1\times10^8$ of such cells per kilogram body weight of the subject, or a value within the range between any two of the foregoing values. In particular embodiments, the numbers and/or concentrations of cells refer to the number of HSC and/or primitive progenitor cells. In other embodiments, the numbers and/or concentrations of cells refer to the number or concentration of all cells, stem cells, primitive progenitor cells and/or haematopoietic cells administered.

In some embodiments, for example, where the subject is a human, the first or subsequent dose includes fewer than about $1\times10^8$ total cells, e.g., in the range of about $1\times10^6$ to $1\times10^8$ such cells, such as $2\times10^6$, $5\times10^6$, $1\times10^7$, $5\times10^7$, or $1\times10^8$ cells/Kg, or the range between any two of the foregoing values, such as between $1\times10^6$ and $1\times10^7$ cells/Kg.

The therapeutic dose of HSC or HSCP to administer to an individual patient can be determined by standard dose ranging studies. For example, for patients with hematologic malignancies undergoing reduced-intensity allogeneic blood cell transplantation, doses in the range of $2-8\times10^6$ cells/Kg ideal body weight (IBW) have been used. In a dose ranging study Mehta et al. (Leukaemia and Lymphoma. 50(9): 1434-1441, 2009) found that $6-8\times10^6$ cells/Kb IBW was optimal.

A therapeutic dosing regimen may require multiple doses, interspersed by a period of time.

The number of doses and interdose period of time will be determined by the attending physician according to standard clinical practice. In some aspects, the size of the first and/or subsequent dose is determined based on one or more criteria such as response of the subject to prior treatment, e.g. chemotherapy, disease burden in the subject, such as tumour load, bulk, size, or degree, extent, or type of metastasis, stage, and/or likelihood or incidence of the subject developing toxic outcomes, e.g., CRS, macrophage activation syndrome, tumour lysis syndrome, neurotoxicity, and/or a host immune response against the cells and/or recombinant receptors being administered.

In some embodiments, the number of cells administered in the subsequent dose is the same as or similar to the number of cells administered in the first dose in any of the embodiments herein.

In other embodiments, the number of cells administered in the subsequent dose is lower than the number of cells administered in the first dose.

In some embodiments, multiple subsequent doses are administered following the first dose, such that an additional dose or doses are administered following administration of the second (or other subsequent) dose. In some aspects, the number of cells administered to the subject in the additional subsequent dose or doses (i.e., the third, fourth, fifth, and so forth) is the same as or similar to the first dose, the second dose, and/or other subsequent dose. In some embodiments, the additional dose or doses are larger than prior doses.

In some embodiments, the first dose includes the cells in an amount that does not cause or reduces the likelihood of toxicity or toxic outcomes, such as cytokine release syndrome (CRS), severe CRS (sCRS), macrophage activation syndrome, tumour lysis syndrome, fever of at least at or about 38 degrees Celsius for three or more days and a plasma level of CRP of at least at or about 20 mg/dL, and/or neurotoxicity. In some embodiments, the number of cells administered in the first dose is determined based on the likelihood that the subject will exhibit toxicity or toxic outcomes, such as CRS, sCRS, and/or CRS-related outcomes following administration of the cells. For example, in some embodiments, the likelihood for the development of toxic outcomes in a subject is predicted based on tumour burden. In some embodiments, the methods include detecting or assessing the toxic outcome and/or disease burden prior to the administration of the dose.

In some embodiments, the second (or other subsequent) dose is administered at a time point at which a clinical risk for developing cytokine-release syndrome (CRS), macrophage activation syndrome, or tumour lysis syndrome, or neurotoxicity is not present or has passed or has subsided following the first administration, such as after a critical window after which such events generally have subsided and/or are less likely to occur, e.g., in 60, 70, 80, 90, or 95% of subjects with a particular disease or condition.

Timing of Doses

As noted above, the therapeutic dosing regimen may require multiple doses, interspersed by a period of time.

In some embodiments, the time between the administration of the first dose and the administration of the subsequent dose is about 28 to about 35 days, about 29 to about 35 days, or more than about 35 days. In some embodiments, the administration of the second dose is at a time point more than about 28 days after the administration of the first dose. In some embodiments, the time between the first and subsequent dose is about 28 days.

A treatment regime may require 1, 2, 3, 4, 5, or more individual doses of HSC.

In some embodiments, the timing of the second or subsequent dose is measured from the initiation of the first dose to the initiation of the subsequent dose. In other embodiments, the timing of the subsequent dose is measured from the completion of the first dose, or from the median day of administration of the first dose, e.g. in the context of split dosing, described herein, where a dose is administered over more than one day, e.g. over 2 days or over 3 days.

In some embodiments, an additional dose or doses, e.g. subsequent doses, are administered following administration of the second dose. In some embodiments, the additional dose or doses are administered at least about 28 days following administration of a prior dose. In some embodiments, no dose is administered less than about 28 days following the prior dose.

In some embodiments, the methods reduce toxicity or toxic outcomes as compared to other methods, for example, by allowing the second administration to occur after toxic outcomes following the first dose have cleared, e.g., which may be at a point in time at which a second administration of cells expressing the first receptor would be cleared by an immune response to the first receptor.

In some embodiments, the consecutive doses may be separated by about 14, about 15, about 21, about 27, or about 28 days. In some embodiments, the consecutive dose is administered 21 days following a prior dose. In some embodiments, the consecutive dose is administered between 14 and 28 days following administration of a prior dose.

Screen

YTHDF2 small molecule inhibitors can be identified by screening test compounds for their ability to inhibit the amount or function of YTHDF2. Molecules that demonstrate inhibitory activity can be used in the methods of treatment disclosed herein, or molecules with more desirable properties (such as increased potency, reduced toxicity or increased half-life) can be designed using these initial hit molecules employing standard structure activity relationship drug discovery and development.

Techniques for screening for YTHDF2 inhibitors are known to those skilled in the art. For example, recombinant human active YTHDF2 (readily available commercially) may be utilised in an assay to measure the effect a test compound has on inhibiting the protein or one of its functions.

Assays can be devised that measure whether a test agent/compound can inhibit YTHDF2 function. Two key functions of YTHDF2 are the interaction between YTHDF2 and CNOT and/or the interaction between YTHDF2 and $m^6A$-modified mRNAs. Such a test would assess whether the test molecule could target and impede these two interactions.

Targeting YTHDF2-CNOT interaction: To identify small molecules which disrupt the YTHDF2-CNOT interaction, a split-*Renilla* luciferase (RL) complementation assay can be employed. Briefly, YTHDF2 (or its CNOT binding peptide) is fused to N-terminal part of RL and CNOT fused to C-terminal part of RL. When YTHDF2 and CNOT bind each other, the two fragments of RL become adjacent thus resulting in reconstitution of their enzymatic activity which can be detected in luciferase assays. This system can be used to perform high-throughput screens for small molecules disrupting protein-protein interactions in cell-free or cell-based assays (Ashkenazi et al., Anal Biochem. 532(53-59, 2017).

In another approach, a protease exclusion assay which can be applied to rapidly screen for protein-protein interaction inhibitors can be employed (Nirantar et al., Biosens Bioelectron. 56(250-257, 2014). Briefly, YTHDF2 (or its 2-CNOT interacting domain) is fused to protease cleavage site and a fluorophore and quencher. In the presence of YTHDF2-CNOT interaction, protease is prevented from accessing the cleavage site. Once YTHDF2-CNOT interaction is disrupted by an inhibitor (e.g. small molecule compound), protease cleavage results in the generation of signal (due to the dissociation of the fluorophore from its quencher).

Targeting the YTHDF2-$m^6A$ interaction: To achieve this, a protein-RNA interaction enzyme-linked immunosorbent assay (PRI-ELISA) can be employed (Alonso et al., Nucleic Acids Res. 43(8): e52, 2015). In this assay, a biotin-labeled $m^6A$-modified RNA sequence is linked to the surface of a multiwell plate. Following the addition of YTHDF2, the binding between YTHDF2 and $m^6A$-modified RNA can be detected by chemiluminescence-based Ultra TMB-ELISA method. This approach can be applied to high-throughput drug screening as described by (Alonso et al., Nucleic Acids Res. 43(8): e52, 2015).

Suitable YTHDF2 inhibitors for use in the present invention can be identified by these tests/screens.

According to another aspect of the invention there is provided an in vitro method for determining whether a YTHDF2 inhibitor test compound has potential as an agent to treat a haematological disorder, comprising determining the effect that the test compound has on the amount or function of YTHDF2 protein expressed in a cell that has been contacted with the test compound, wherein if the test compound causes a decrease in YTHDF2 protein level or function in the contacted cell then the test compound has potential as an agent to treat a disease or disorder characterised by elevated YTHDF2, such as a haematopoietic disorder.

In particular embodiments, the effect that the test compound has on disrupting the interaction of (i) YTHDF2 with CCR4-NOT complex or (ii) YTHDF2 interaction with $m^6A$ is determined and a test compound which disrupts at least one of said interactions is one that has potential as an agent to treat a haematopoietic disorder.

According to another aspect of the invention there is provided a method for selecting a compound for use in the treatment of a disease, disorder or condition characterised by elevated YTHDF2 comprising determining in an in vitro setting whether the test compound is capable of inhibiting YTHDF2 protein, wherein a test compound that inhibits YTHDF2 protein is selected for use in the treatment of a disease, disorder or condition characterised by elevated YTHDF2. By inhibiting YTHDF2 protein we mean inhibiting the amount or function (including activity) of the protein.

In a particular embodiment, the disease, disorder or condition characterised by elevated YTHDF2 is a haematopoietic disorder as described herein. In particular embodiments, the disease, disorder or condition is selected from the group consisting of: AML, CLL, DLBCL, T-ALL, B-ALL.

In a particular embodiment, the selected test compound is then formulated with one or more pharmaceutically acceptable excipients as described herein.

Patient Selection

The therapeutic treatments described herein are applicable to patients who possess a disease of condition characterised by elevated YTHDF2, such as a haematological disorder like AML. Accordingly, the invention also provides for methods for identifying such patients/selecting such patients for therapeutic treatment.

In accordance with another aspect of the invention there is provided a method for selecting an individual suffering from a disease or condition characterised by elevated YTHDF2, such as a haematological disorder, comprising determining whether the patient's aberrant cells (i) express elevated YTHDF2 mRNA transcript or protein levels relative to a control or normal cell, wherein if YTHDF2 mRNA transcript or protein levels in the individual's cells are elevated relative to a control or normal cell the individual is selected for treatment with an YTHDF2 inhibitor.

A patient's aberrant cells as used herein refers to diseased cells, for example with a haematological cancer a diseased cancer cell such as a leukaemia cell.

The diagnostic/determining methods of the invention can be undertaken using a sample previously taken from the individual or patient. Such samples may be preserved by freezing or fixed and embedded in formalin-paraffin or other media. Alternatively, a fresh cell (e.g. cancer cell) containing sample may be obtained and used directly or frozen and tested later.

In a particular embodiment, the patient's aberrant cells are in a biological sample previously taken from the patient. Typically, the biological sample comprises biological tissue or fluid. In particular embodiments, the biological sample is selected from the group consisting of: blood, bone marrow, of tumour tissue.

In AML/haematological malignancy patients the sample may be a peripheral blood sample and/or bone marrow aspirate. In other cancers, the sample could be a tissue sample, such as those obtained using thin needle biopsies.

In a particular embodiment, the amount of YTHDF2 protein in the patient's aberrant cells is determined using immunohistochemistry or LC-MS.

In a particular embodiment, the amount of YTHDF2 mRNA transcript in the patient's aberrant cells is determined using quantitative RT-PCR.

YTHDF2⁻ Haematopoietic Stem Cells

The inventors have discovered that inactivating YTHDF2 in haematopoietic stem cells enhances the ability of these cells to self-renew and maintain multilineage differentiation potential. These findings open up the possibility of ex vivo expanding HSC for stem cell transplantation purposes, the enhancement of human haematopoietic reconstitution upon transplantation, efficient blood regeneration following chemotherapy or robust HSC maintenance under leukaemic conditions.

Thus, according to another aspect of the invention there is provided a haematopoietic stem cell characterised in that the cell has been treated to inactivate YTHDF2 gene or YTHDF2 function.

According to another aspect of the invention there is provided a haematopoietic stem cell with an inactive YTHDF2 gene.

In order to prepare a HSC with inactivated YTHDF2 gene or YTHDF2 function the haematopoietic stem cell can be treated with a YTHDF2 inhibitor as described herein. One way to effect this is to culture the HSC in a medium that comprises a YTHDF2 inhibitor in an amount sufficient to cause inactivation of the YTHDF2 gene or to inactivate or impede YTHDF2 function.

Human cord blood HSCs can be cultured in serum-free medium supplemented with Stem cell factor (SCF), Fms-related tyrosine kinase 3 ligand (FLT-3L), thrombopoietin (TPO), and interleukin-6 (IL-6) (all at 50 ng/ml) without the addition of antibiotics for 10-15 days at 37° C.

Thus, according to another aspect of the invention there is provided a method preparing haematopoietic stem cells with inactivated YTHDF2, comprising culturing a population of HSC in a medium that comprises a YTHDF2 inhibitor in an amount sufficient to cause inactivation of the YTHDF2 gene or to inactivate or impede YTHDF2 function in the HSCs.

Human cord blood or BM HSCs can be cultured in serum-free medium supplemented with Stem cell factor (SCF), Fms-related tyrosine kinase 3 ligand (FLT-3L), thrombopoietin (TPO), and interleukin-6 (IL-6) (all at 50 ng/ml) without the addition of antibiotics for 10-15 days (Wagner et al., Cell Stem Cell. 18(1): 144-155, 2016).

HSC to be inactivated in this way can be isolated from bone marrow or blood and then sorted, for example, from adult BM or CB by FACS sorting using the following immunophenotypic features: Lin−CD34+CD38−CD45RA−CD49f+CD90+(Laurenti et al., Cell Stem Cell. 16(3): 302-313, 2015, Notta et al., Science. 351(6269): aab2116, 2016).

Another way to generate a HSC with inactivated YTHDF2 is to transfect a HSC with a nucleic acid molecule capable of transiently or stably inactivating the YTHDF2 gene. The transfection can be conducted using known techniques such as electroporation (see Bak et al., Nature Protocols. 13:358-376, 2018).

Transfection is the process of introducing exogenous nucleic acid into an eukaryotic cell.

Transfection typically involves opening transient "holes" in the cell membrane to allow the nucleic acid material to pass into the cell. Transfection can be carried out using a variety of well-known techniques, including calcium phosphate treatment, cell squeezing, electroporation, or by mixing a cationic lipid with the nucleic acid material to produce liposomes which fuse with the cell membrane and deposit the nucleic acid material inside. If the introduced nucleic acid permanently integrates with the cellular genomic DNA it will be transferred to descendent cells it is said to be stably integrated and the effects of the introduced nucleic acid will last for a long time. In contrast, if the introduced exogenous nucleic acid is not permanently integrated into the cellular genome it is said to be transiently transfected and the effects of the introduced nucleic acid in the cells will only last a short time. Stably and transiently inactivated of YTHDF2 refer to whether or not the effect on inactivation is permanent (stably) or short-term (transient).

The YTHDF2 can be stably inactivated using well known gene-editing techniques such as CRISPR-Cas9 (see Bak et al., Nature Protocols. 13:358-376, 2018) or by inactivating the gene using siRNA. The use of siRNA can generate a HSC that is transiently inactivated. A transiently inactivated HSC has the benefit that after further rounds of self-renewal (via division) the inactivation is lifted and new populations of normal HSC, and thus normal haematopoietic cells (e.g. blood cells) arise.

In particular embodiments, the haematopoietic stem cell is one wherein the YTHDF2 gene is stably or transiently inactivated.

According to another aspect of the invention there is provided a method for preparing a YTHDF2 inactivated HSC comprising introducing into the HSC a nucleic acid molecule capable of blocking or inactivating the YTHDF2 gene in the cell. In one embodiment, the nucleic acid molecule is an siRNA or ASO molecule. In another embodiment, the nucleic acid molecule is a CRISPR-Cas9 guide molecule capable of inactivating, such as deleting, the YTHDF2 gene from the cell using CRISPR-Cas9 homologous recombination technique (e.g. see WO13/176772, WO14/093595; Bak et al., Nature Protocols. 13:358-376, 2018; and Mandal et al. CellStemCell. 15(5):643-652, 2014). In one embodiment, the nucleic acid molecule is introduced into the HSC via transfection. In one embodiment, the nucleic acid molecule is introduced into the HSC by electroporation.

In one embodiment, the YTHDF2 gene is inactivated using a nucleic acid inhibitor molecule capable of binding to YTHDF2 gene or YTHDF2 mRNA transcript.

According to another aspect of the invention there is provided a method for maintaining long-term self-renewal capacity and multilineage differentiation potential in a HSC comprising treating the HSC to inhibit or inactivate YTHDF2 gene or protein.

According to another aspect of the invention there is provided a method for preparing an inactivated YTHDF2 HSC comprising transfecting a HSC with a nucleic acid molecule capable of inactivating the YTHDF2 gene in the HSC.

In one embodiment, the YTHDF2 gene is inactivated using Crispr-Cas9 gene editing.

In another embodiment, the YTHDF2 gene is inactivated by gene-silencing or knock-down, using for example an shRNA molecule.

In another embodiment, the YTHDF2 gene is inactivated using a nucleic acid inhibitor molecule capable of binding to YTHDF2 gene or YTHDF2 mRNA transcript.

In another embodiment, the YTHDF2 gene is inactivated using a lentivirus vector comprising a nucleic acid capable of inactivating YTHDF2 gene. In one embodiment, the lentivirus vector is capable of expressing an RNAi nucleic acid molecule (e.g. shRNA) capable of hybridising to YTHDF2 mRNA.

In another embodiment, the YTHDF2 gene is inactivated using a compound or nucleic acid capable of binding to YTHDF2 protein.

In one embodiment, the YTHDF2 gene function is inactivated

In another embodiment, the YTHDF2 protein function is inactivated

According to particular aspects there is provided a HSC produced by the methods used to inactivate the YTHDF2 gene. In a particular embodiment, there is provided a population of cells that have YTHDF2 gene inactivated.

It will be appreciated that in distinct embodiments, the YTHDF2 gene can be inactivated transiently or stably (permanently) depending on the type of system utilised.

In order to benefit from the invention, it is necessary to lower the amount of YTHDF2 in the cell. In one embodiment, the YTHDF2 gene is silenced or rendered completely inactive. In another embodiment, the amount of YTHDF2 produced by the cell is reduced, such as by at least: 20%, 25%, 30%, 50%, 60%, 75%, 90%, 95%, 96%, 97%, 98% or 99%, when compared to the level in normal cells. Typically, the YTHDF2 in such HSC is still classed as being inactivated, though only partially.

The YTHDF2 inactivated HSC can be used in haematopoietic stem cell transplantation (HSCT). Thus, in one embodiment the YTHDF2 inactivated HSC is formulated for administration to a patient.

Thus, according to one aspect there is provided there is provided a haematopoietic stem cell composition comprising one or more YTHDF2 inactivated stem cells dispersed within a medium. The medium can be a culture medium or other medium that comprises necessary components for cell survival in an ex vivo setting.

According to another aspect there is provided a pharmaceutical composition comprising a YTHDF2 inactivated HSC. In a particular embodiment, a multitude of YTHDF2 inactivated HSCs are formulated for HSCT purposes.

Suitable HSC formulations, dosages and modes of administration are disclosed elsewhere in this specification According to another aspect of the invention there is provided a method of treating a patient in need of HSCT comprising administering to the patient an effective amount of a YTHDF2 inactivated HSC.

According to another aspect of the invention there is provided a method for reconstituting the hematopoietic system or tissue of a patient in need thereof, comprising administering to the patient an effective amount of a YTHDF2 inactivated HSC, or a population thereof.

According to another aspect of the invention there is provided a YTHDF2 inactivated HSC or a population thereof, or a pharmaceutical composition comprising either for use in HSCT.

According to another aspect of the invention there is provided a YTHDF2 inactivated HSC or a population thereof, or a pharmaceutical composition comprising either for reconstituting the hematopoietic system or tissue of a subject.

According to another aspect of the invention there is provided a method for ex vivo expansion of multipotent hematopoietic cells, comprising culturing multipotent YTHDF2 inactivated hematopoietic cells in a culture medium and under conditions to produce a cell population of expanded multipotent hematopoietic cells.

By way of example, such cells can be cultured in serum-free medium supplemented with stem cell factor (SCF), Fms-related tyrosine kinase 3 ligand (FLT-3L), thrombopoietin (TPO), and interleukin-6 (IL-6) (all at 50 ng/ml) without the addition of antibiotics for 10-15 days at 37° C. Other means for culturing cells are known in the art or described elsewhere herein.

In particular embodiments, the multipotent hematopoietic cells are haematopoietic stem cells and/or primitive progenitor cells. In one embodiment, the hematopoietic stem cells and/or primitive progenitor cells are obtained by CD34 selection.

In particular embodiments, the YTHDF2 in the HSC is completely inactive. In other embodiments, the YTHDF2 in the HSC is inactivate by at least 50%, at least 75%, at least 90%, or at least 99%.

In accordance with another aspect of the present invention, there is provided a method for reconstituting the hematopoietic system or tissue of a subject comprising administering to said subject the YTHDF2 inactivated hematopoietic stem cell of the present invention or a population of such cells.

HSC Expansion

According to another aspect of the invention there is provided a method for ex vivo expansion of multipotent hematopoietic cells, comprising culturing multipotent hematopoietic cells in a medium comprising an YTHDF2 inhibitor, wherein said inhibitor is present in an amount effective to produce an expanded cell population of multipotent hematopoietic cells. In particular embodiments, the multipotent hematopoietic cells are haematopoietic stem cells and/or primitive progenitor cells.

In accordance with another aspect of the present invention, there is provided a method for increasing the expansion and/or differentiation of a HSC or HSC population comprising: culturing multipotent hematopoietic cell(s) with an YTHDF2 inhibitor capable of: (i) decreasing the level and/or activity of YTHDF2 protein; or (ii) decreasing the level of a nucleic acid encoding the YTHDF2 protein, in the HSC or HSC population.

The YTHDF2 inhibitor is one that is described elsewhere in this specification.

Multipotent haematopoietic cells (such as stem cells and early/primitive progenitor cells) can be obtained from cord blood, such as from the blood squeezed out of the umbilicus of a newborn animal, e.g. human. Of course, cord blood only has a limited amount of HSC so improved methods of expanding these cells is needed. The blood would be extracted and the different populations of cells sorted into separate fractions of homogeneous or near homogenous populations of cells, using for example, fluorescence activated cell sorting (FACS) apparatus. The multipotent stem and/or early progenitor cells can then be treated with a YTHDF2 inhibitor in accordance with the invention.

Multipotent haematopoietic cells can also be obtained from bone marrow. Multipotent haematopoietic cells present in marrow extracted from a donor or patient can be sorted in the same was as described for cord blood above.

In one embodiment, after a suitable period of culturing, the population of cells is the culture medium is substantially enriched in a subpopulation of multipotent hematopoietic stem cells as compared to expansion of said multipotent hematopoietic cells in the absence of the inhibitor.

In particular embodiments, the multipotent hematopoietic cells are haematopoietic stem cells and/or primitive (early) progenitor cells.

In distinct embodiments, the multipotent hematopoietic stem cells to be expanded are obtained from cord blood, peripheral blood, or bone marrow.

HSCs in blood (cord blood or peripheral blood) can be extracted using pheresis, wherein blood is extracted from the donor, passed through a machine that extracts the stem cells and returns other portions of the blood to the donor.

In particular embodiments, the cells to be expanded are hematopoietic progenitor and/or hematopoietic stem cells. In a particular embodiment, the hematopoietic progenitor and/or hematopoietic stem cells are obtained by CD34 selection. Such as via use of FACS. For example, mononuclear cells can be isolated by density-gradient centrifugation with Ficoll-Paque Plus. CD34$^+$ cells can then be enriched by FACS sorting or using immunomagnetic selection (Guo et al., Nat Med. 24(3): 360-367, 2018). Further enrichment for human HSCs can be achieved by FACS sorting Lin−CD34+CD38−CD45RA−CD49f+CD90+ cells from the CD34-enriched cell fraction (Laurenti et al., Cell Stem Cell. 16(3): 302-313, 2015, Notta et al., Science. 351(6269): aab2116, 2016).

Typical methods for cell enrichment and/or isolation include density step gradients (e.g., Ficoll®, colloidal silica), elutriation, centrifugation, lysis of erythrocytes by hypotonic shock, and various combinations of such methods. For example, purification of stem cells from bone marrow requires removal of erythrocytes and granulocytes, which is often accomplished by Ficoll® density gradient centrifugation, followed by repeated washing steps by conventional centrifugation.

Methods for cell enrichment and/or isolation may also include filtration on various types of filters known in the art for cell separation. For example, tangential flow filtration, also known as cross-flow filtration, may be used for enriching stem cells from a heterogeneous mixture of bone marrow or blood constituents, as disclosed in U.S. Pat. No. 7,790, 039.

Separation of multipotent cells from mixtures may also incorporate a step of absorption to a suitable substrate such as a plastic culture vessel.

In one embodiment, the expanded cells retain the capacity for in vivo hematopoietic reconstitution upon transplantation.

In another embodiment, the growth of said hematopoietic stem cells in the presence of said YTHDF2 inhibitor results in at least a 3-fold, such as at least 5-fold or 10-fold, increase in CD34+CD90+ cells or Lin−CD34+CD38−CD45RA−CD49f+CD90+ cells as compared to growth in the absence of said YTHDF2 inhibitor.

The hematopoietic cells are separated from other cells by selecting for cells for expression of at least one marker associated with stem cells or by physical separation means. In particular embodiments, the marker is selected from the group consisting of Lineage (Lin), CD34, CD38, CD45RA, CD49f, and CD90.

According to another aspect there is provided a YTHDF2 inactivated HSC, as described herein, or a pharmaceutical composition comprising one or more YTHDF2 inactivated HSCs, for use in therapy.

In one embodiment, the YTHDF2 inactivated HSC, or a pharmaceutical composition comprising one or more YTHDF2 inactivated HSCs, is used in haematopoietic stem cell transplantation. In another embodiment, the YTHDF2 inactivated HSC, or a pharmaceutical composition comprising one or more YTHDF2 inactivated HSCs, is for use in replenishing HSC or haematopoietic cells (HCs) in a patient in need thereof. In another embodiment, the patient has been diagnosed with haematological cancer or is in need of HSCT. In one embodiment, the patient receiving the HSCT with one or more YTHDF2 inactivated HSCs has undergone therapy that has ablated the HSC and/or haematopoietic cells. In particular embodiments, the patient has received chemotherapy or radiotherapy. In one embodiment, the patient is given HSCT with one or more YTHDF2 inactivated HSCs in combination with chemotherapy or radiotherapy. In one embodiment, the HSCT is given prior to chemotherapy or radiotherapy. In another embodiment, the HSCT is given after chemotherapy/cancer treatment regimens (including platinum compounds, antimetabolites, alkylating agents, anthracyclines).

The invention will be described further by the following non-limiting examples and Figures.

(A) The sequences encoding the eGFP-PreScission-His6-Flag-HA2 epitope tag were inserted after the starting ATG codon in exon 1 of the Ythdf2 locus, and exon 2 was flanked by LoxP sites (see Ivanova et al., Mol Cell. 67(6): 1059-1067 e1054, 2017). The Ythdf2$^{fl}$ allele codes for eGFP-PreScission-His6-Flag-HA2-YTHDF2 fusion protein (referred to as GFP-YTHDF2 protein). (B) GFP expression in the indicated foetal liver (FL) cell populations from Ythdf2$^{fl/fl}$ 14.5 days post coitum (dpc) embryos. YTHDF2 is uniformly expressed in FL Lin$^-$Sca-1$^+$c-Kit$^+$ (LSK) cells, LSKCD48$^-$CD150$^+$ HSCs, LSKCD48$^-$CD150$^-$ multipotent progenitors (MPPs), primitive haematopoietic progenitor cells (i.e. LSKCD48$^+$CD150$^-$ HPC-1 and LSKCD48$^+$CD150$^+$ HPC-2 populations), and Lin$^-$Sca-1$^-$c-Kit$^+$ (LK) myeloid progenitors, and its expression is decreased in differentiated Lin$^+$ cells. The data represent mean fluorescence intensity (MFI)±SEM (n=3-4 mice per genotype). (C) GFP expression in the BM cell populations from 8-12-week-old mice. YTHDF2 is expressed at higher levels in HSC/progenitor cells compared to the mature Lin$^+$ cell compartment. The data represent MFI±SEM (n=3-4 mice per genotype).

Figure 2:
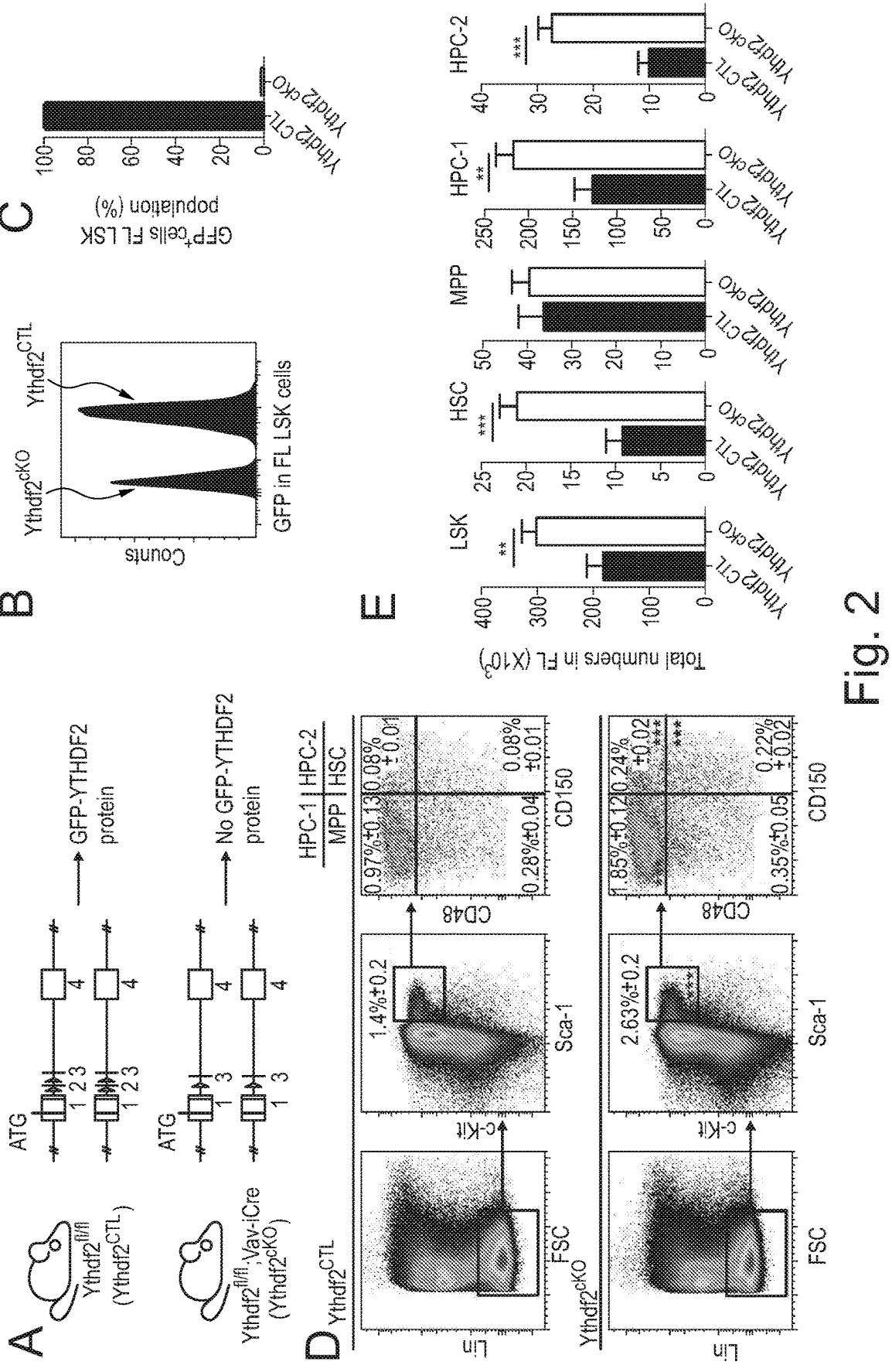
Figure 2:
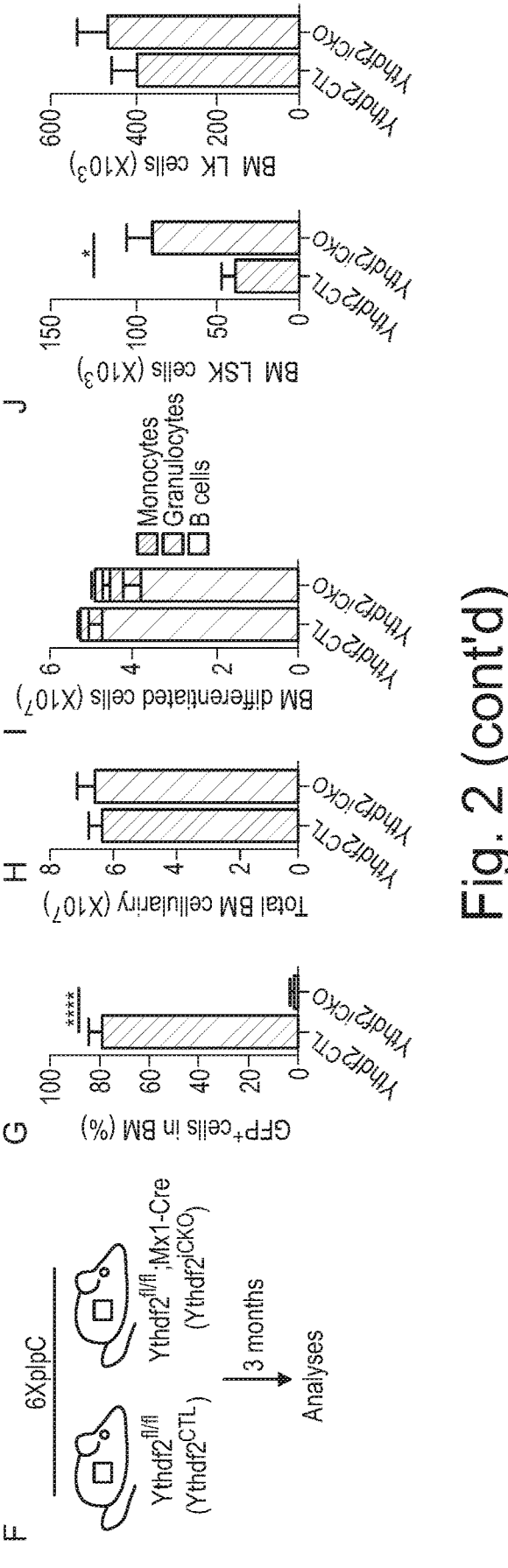

FIG. 2. Ythdf2 deletion promotes FL HSC and primitive progenitor cell expansion. (A) Deletion of Ythdf2 from the haematopoietic system using Vav-iCre. FL cells from control 14.5 dpc Ythdf2$^{fl/fl}$ (Ythdf2$^{CTL}$) embryos produce normal GFP-YTHDF2 protein. In Ythdf2$^{fl/fl}$; Vav-iCre (Ythdf2$^{cKO}$) mice, exon 2 is deleted resulting in a frameshift mutation and a complete loss of the GFP-YTHDF2 protein. (B) A representative histogram showing GFP expression in Ythdf2$^{CTL}$ LSK cells and the lack of GFP expression in Ythdf2$^{cKO}$ LSK cells. (C) Frequency of GFP-positive cells in 14.5 dpc FLs of Ythdf2$^{CTL}$ and Ythdf2$^{cKO}$ embryos. Data are mean±SEM (n=5 per genotype). Haematopoietic cells from Ythdf2$^{CKO}$ embryos/mice have no GFP-YTHDF2 protein expression. (D-E) Frequencies (D) and total numbers (E) of LSK, HSC, MPP, HPC-1 and HPC-2 cell populations in FLs from 14. 5dpc Ythdf2$^{CTL}$ and Ythdf2$^{cKO}$ embryos. Data are mean±SEM (control n=10 per genotype). , P<0.01; *, P<0.001 (Mann-Whitney U test). (F) Ythdf2$^{fl/fl}$; Mx1-Cre (Ythdf2$^{iCKO}$) and control Ythdf2$^{fl/fl}$ (Ythdf2$^{CTL}$) mice were injected with plpC and analyzed 3 months after the last injection. (G) The graph shows the percentage of GFP-positive cells in BM of plpC-treated Ythdf2$^{iCKO}$ and Ythdf2$^{CTL}$ mice (n=10-12). (H) Total BM cellularity of plpC-treated Ythdf2$^{iCKO}$ and Ythdf2$^{CTL}$ mice. (I) Total cell numbers of BM monocytes, granulocytes and B cells. (J) Total cell numbers of BM LSK and LK cell populations.

Figure 3:
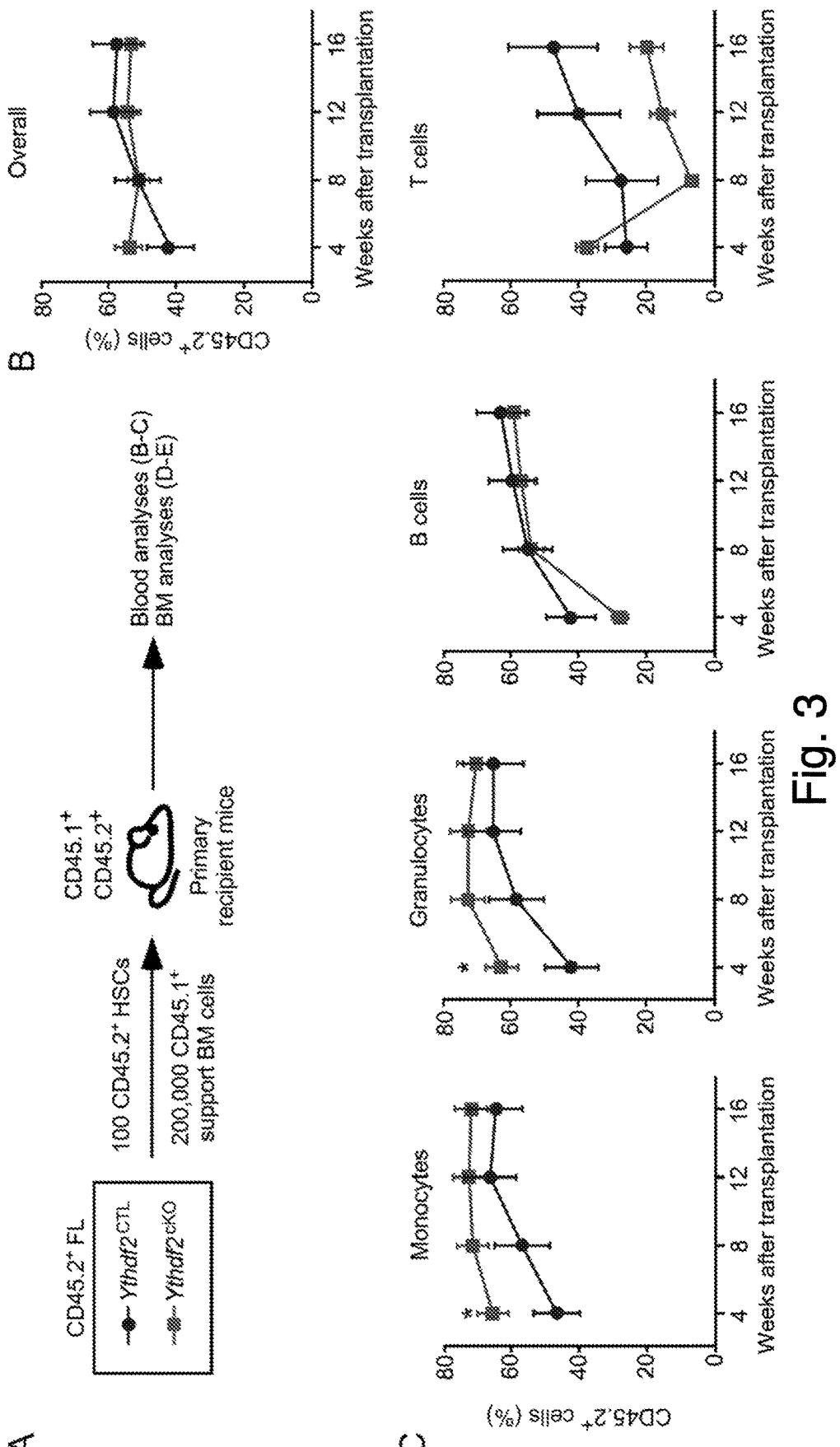
Figure 3:
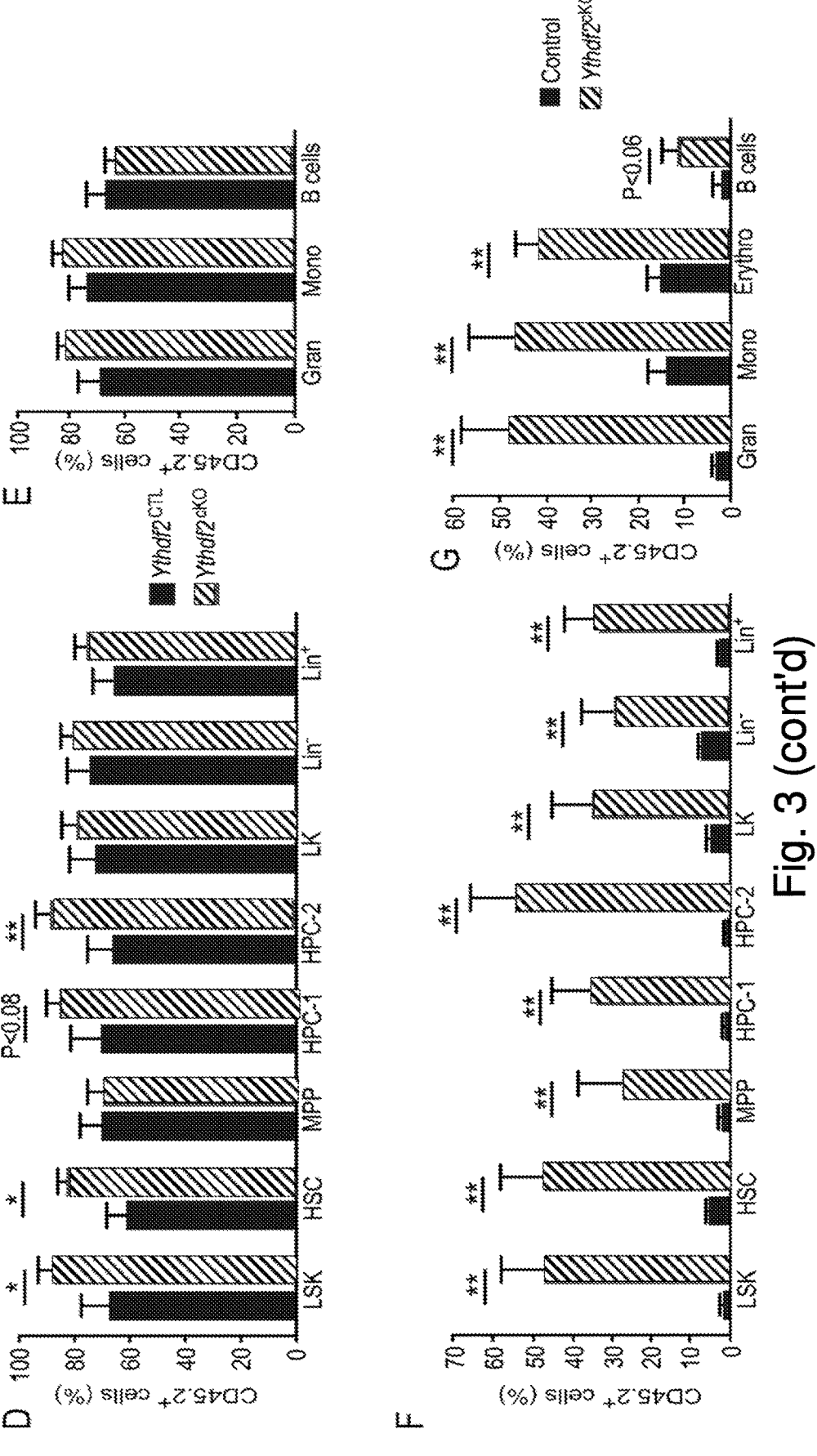

FIG. 3. Ythdf2-deficient FL HSCs display enhanced capacity to reconstitute the HSC pool of the recipient mice upon transplantation. (A) 100 HSCs (CD45.2$^+$LSKCD48$^-$CD150$^+$ cells) sorted from FLs of 14.5 dpc embryos were mixed with 200,000 support CD45.1$^+$ BM cells and injected into lethally irradiated (11 Gy delivered in a split dose) CD45.1$^+$/CD45.2$^+$ recipient mice. n=6-9 recipients per genotype. 16 weeks after transplantation, stem/progenitor cells were harvested and re-transplanted into secondary recipient mice (n=8-9 recipients per genotype). (B) Percentage of donor-derived CD45.2$^+$ cells in the peripheral blood (PB) of the recipient mice. Data are mean±SEM. (C) Percentage of CD45.2$^+$ cells in the monocyte, granulocyte, B cell and T cell compartments in the PB of primary recipients. Data are mean±SEM. *, P<0.05 (Mann-Whitney U test). (D) Percentage of donor-derived CD45.2$^+$ cells in the LSK, HSC, MPP, HPC-1, HPC2, LK, Lin$^-$ and Lin$^+$ cell compartments in the BM of the primary recipient mice 16 weeks after transplantation. Data are mean±SEM. *, P<0.05; , P<0.01 (Mann-Whitney U test). (E) Percentage (mean±SEM) of donor-derived CD45.2$^+$ to differentiated cell compartments in the BM of the primary recipient mice 16 weeks after transplantation. (F) Percentage of donor-derived CD45.2$^+$ cells in the LSK, HSC, MPP, HPC-1, HPC2, LK, Lin$^-$ and Lin$^+$ cell compartments in the BM of the secondary recipient mice 16 weeks after transplantation. Data are mean±SEM. , P<0.01 (Mann-Whitney U test). (G) Percentage (mean±SEM) of donor-derived CD45.2$^+$ to differentiated cell compartments in the BM of the secondary recipient mice 16 weeks after transplantation. Data are mean±SEM. **, P<0.01 (Mann-Whitney U test).

Figure 4:
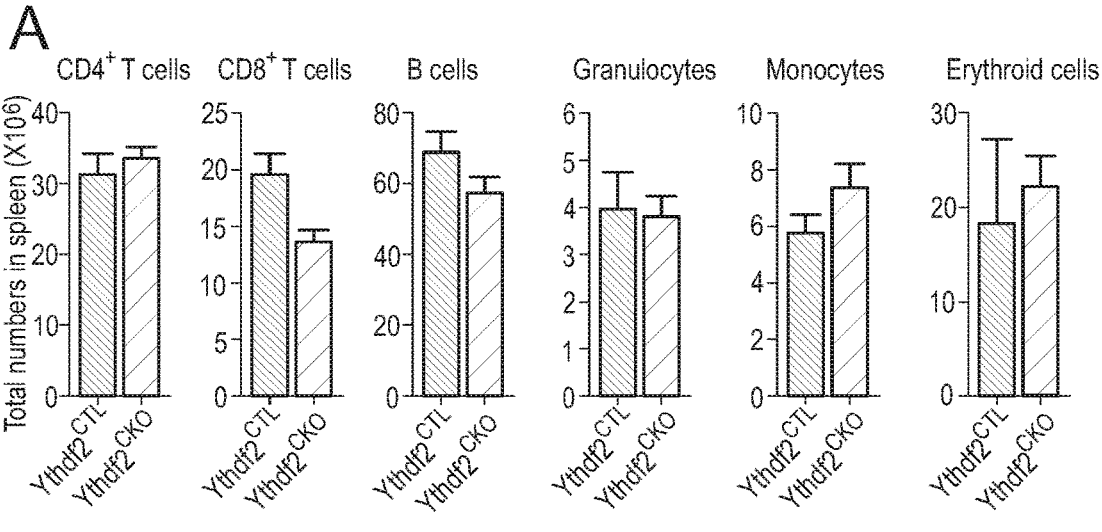
Figure 4:
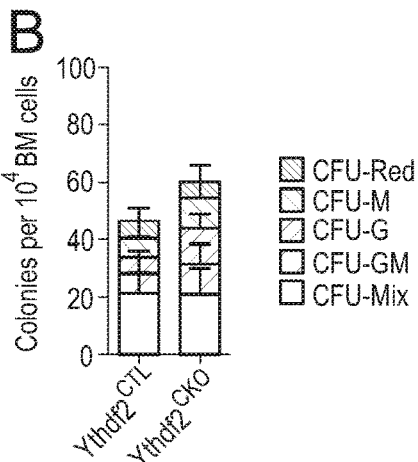
Figure 4:
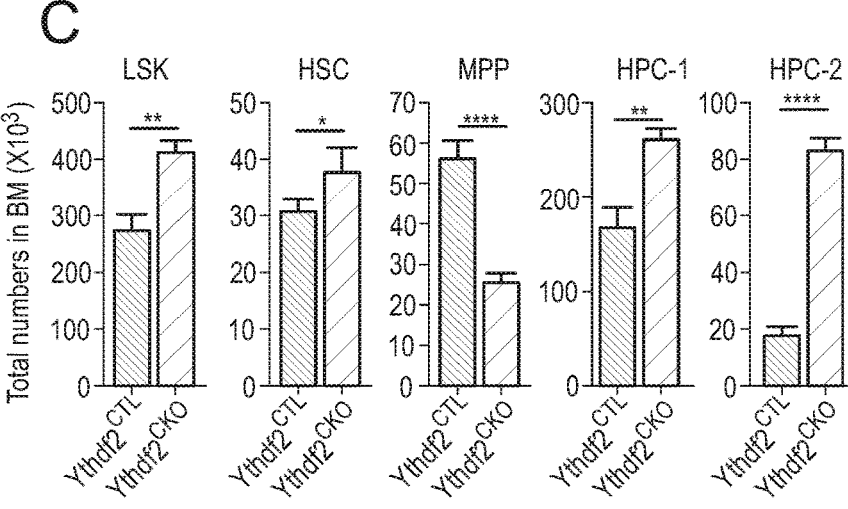
Figure 4:
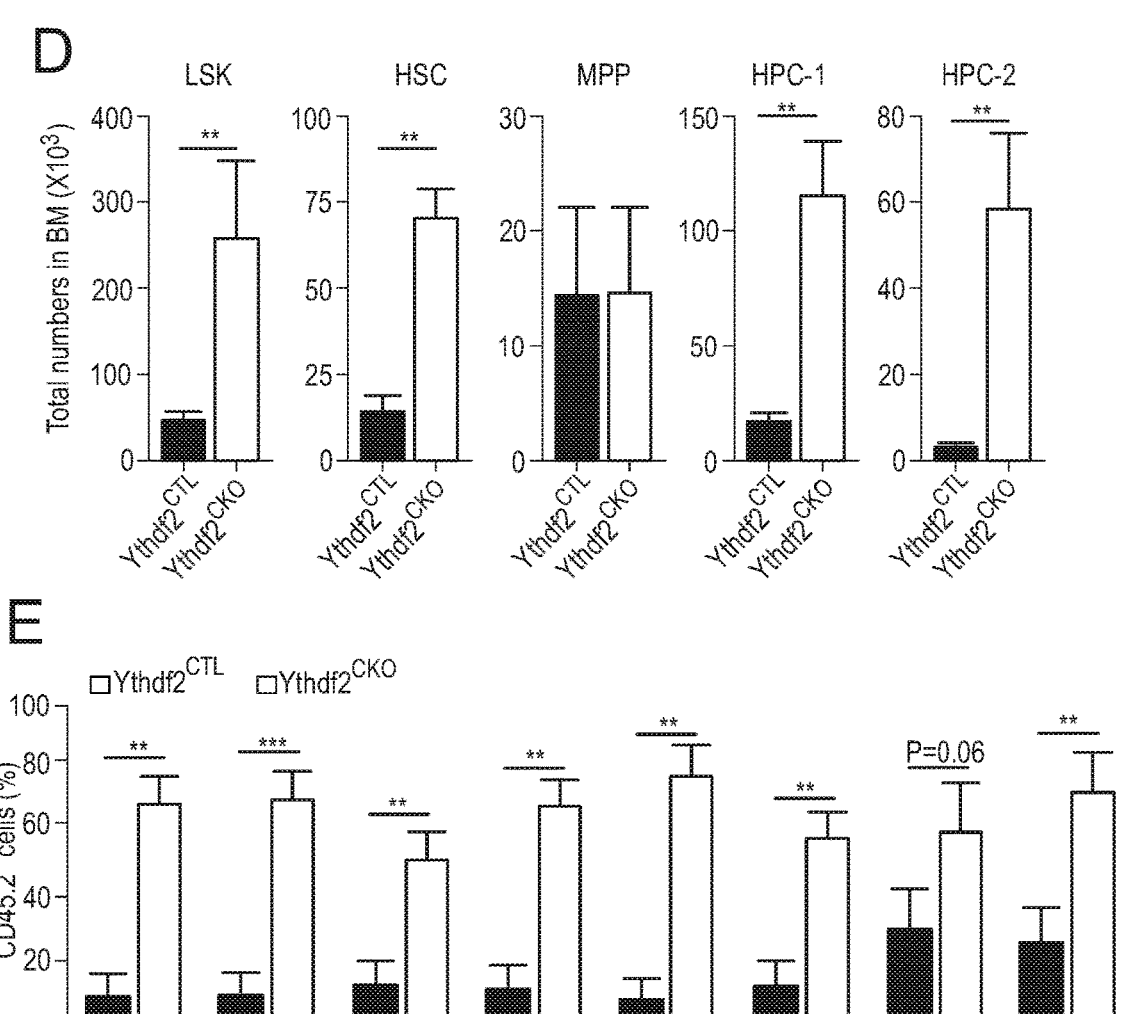
Figure 4:
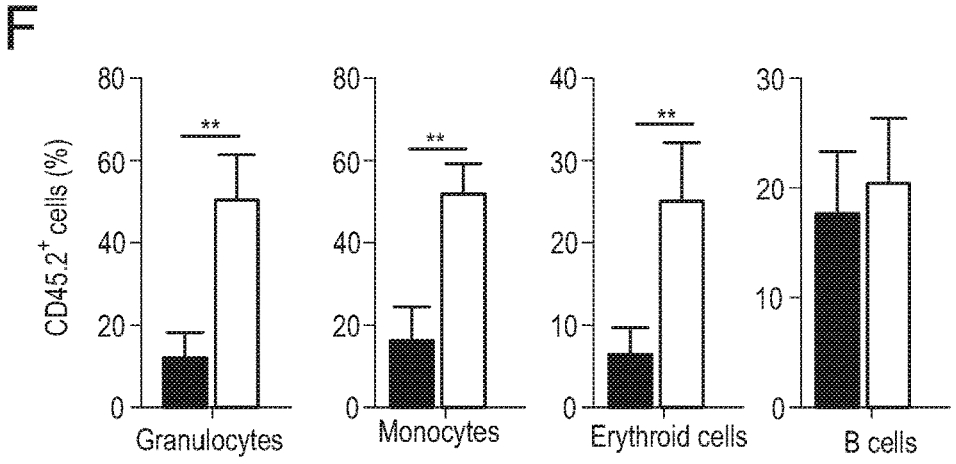

FIG. 4. Ythdf2 deletion results in adult HSC expansion and enhanced HSC reconstitution potential. (A) Total numbers of T cells, B cells, granulocytes monocytes and erythroid cells in spleens from Ythdf2$^{CTL}$ and Ythdf2$^{CKO}$ mice. Data are mean±s.e.m. (n=5-6 mice per genotype). (B) CFU assays performed with BM cells from 8-10-wk-old mice. CFU-Red, CFU-erythroid and/or megakaryocyte; CFU-G, CFU-granulocyte; CFU-M, CFU-monocyte/macrophage; CFU-GM, CFU-granulocyte and monocyte/macrophage; CFU-Mix, at least three of the following: granulocyte, erythroid, monocyte/macrophage, and megakaryocyte. Data are mean±s.e.m. (n=4 per genotype). (C) Total number of BM LSK, HSC, MPP, HPC-1 and HPC-2 cell populations from Ythdf2$^{CTL}$ and Ythdf2$^{CKO}$ mice (n=6-7 mice per genotype). Mice were 8-10 weeks old. *, P<0.05; , P<0.01; , P<0.0001 (D) Total number of BM LSK, HSC, MPP, HPC-1 and HPC-2 cell populations from Ythdf2$^{CTL}$ and Ythdf2$^{CKO}$ mice (n=6-7 mice per genotype) treated with 5-fluorouracil. Mice (8-10 weeks old) were treated with 3 doses of 5-fluorouracil administered every month and analysed a month after last dose. , P<0.01. (E) 200 BM HSCs were transplanted into lethally irradiated 8-10-wk-old syngeneic CD45.1$^+$/CD45.2$^+$ recipient mice (n=6-9 recipients per genotype) together with 2×10$^5$ CD45.1$^+$ competitor BM cells. The graph shows the percentage of CD45.2$^+$ cells in the LSK, HSC, MPP, HPC1-2, LK, Lin$^-$ and Lin$^+$ cells compartments in the BM of recipient mice. Data are mean±s.e.m. , P<0.01. (F) The graph shows the percentage of CD45.2$^+$ cells in differentiated cell compartments in the BM of recipient mice. Data are mean±s.e.m. , P<0.01.

Figure 5:
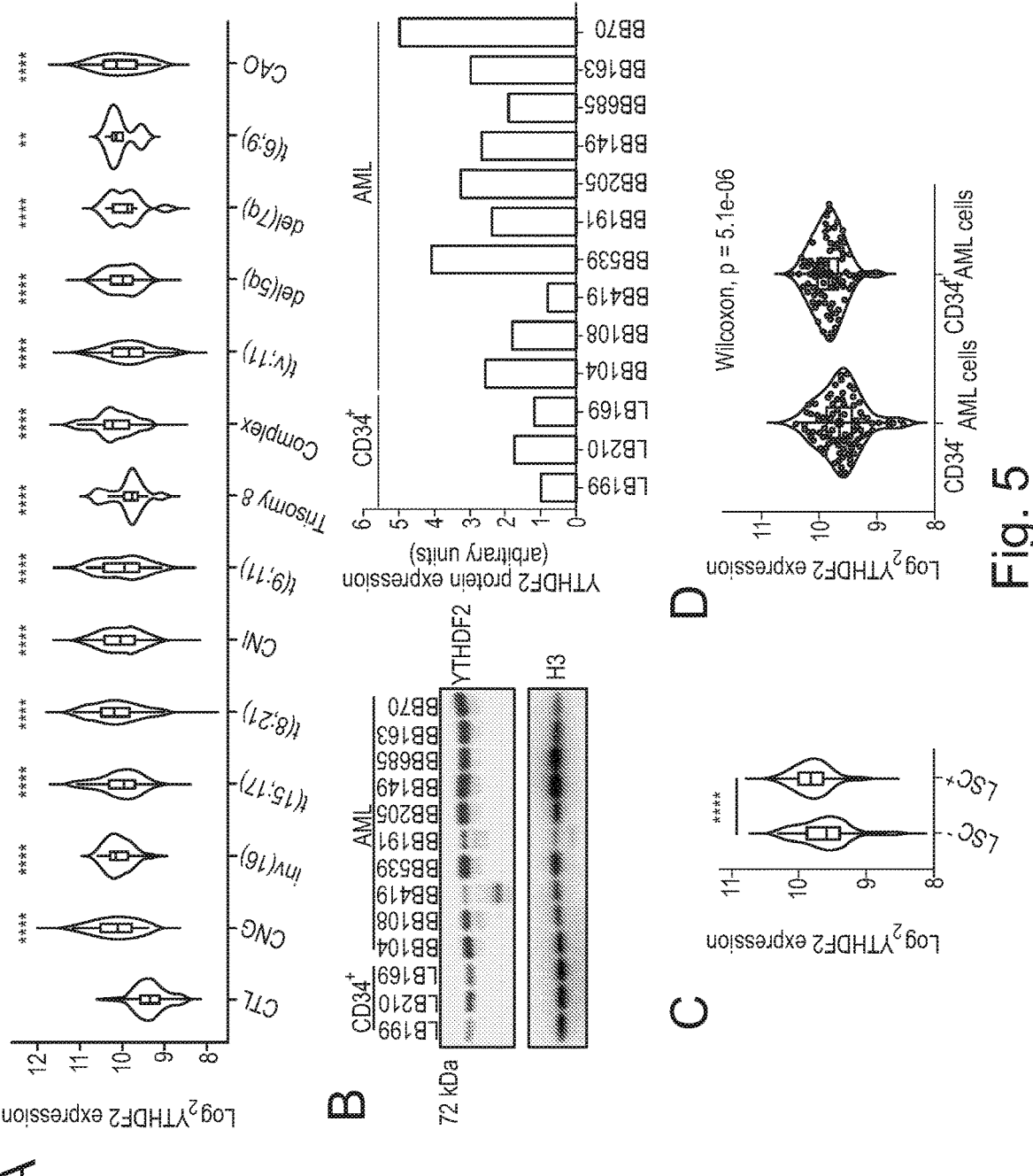

FIG. 5. YTHDF2 gene expression is increased in different AML subtypes and correlates with LSC activity. (A) YTHDF2 gene expression in control (CTL) and different cytogenetic subgroups of human AML blood cell samples. Violin plots show the distribution of log$_2$ expression values. Horizontal line in the boxplots indicates median. , P<0.01; , P<0.0001. CNG, cytologically normal with good prognosis; CNI, cytologically normal with intermediate prognosis; CAO, cytologically abnormal not otherwise specified. (B) Western blot of YTHDF2 in normal human CD34$^+$ cells and AML samples (karyotype details are shown in STAR Methods) is shown (left panel). α-Histone 3 (H3) was used as a loading control. Quantification of YTHDF2 normalized to H3 expression is presented (right panel). (C) YTHDF2 gene expression in primitive AML cell compartments with (LSC$^+$) and without (LSC$^-$) leukaemic engraftment potential. **, P<0.0001. (D) YTHDF2 gene expression in CD34$^-$ and CD34$^+$ AML cell compartments. FIG.

5C-D were generated by reanalysis of the dataset published by Ng S., et al., Nature 540, 433-437, 2016.

Figure 6:
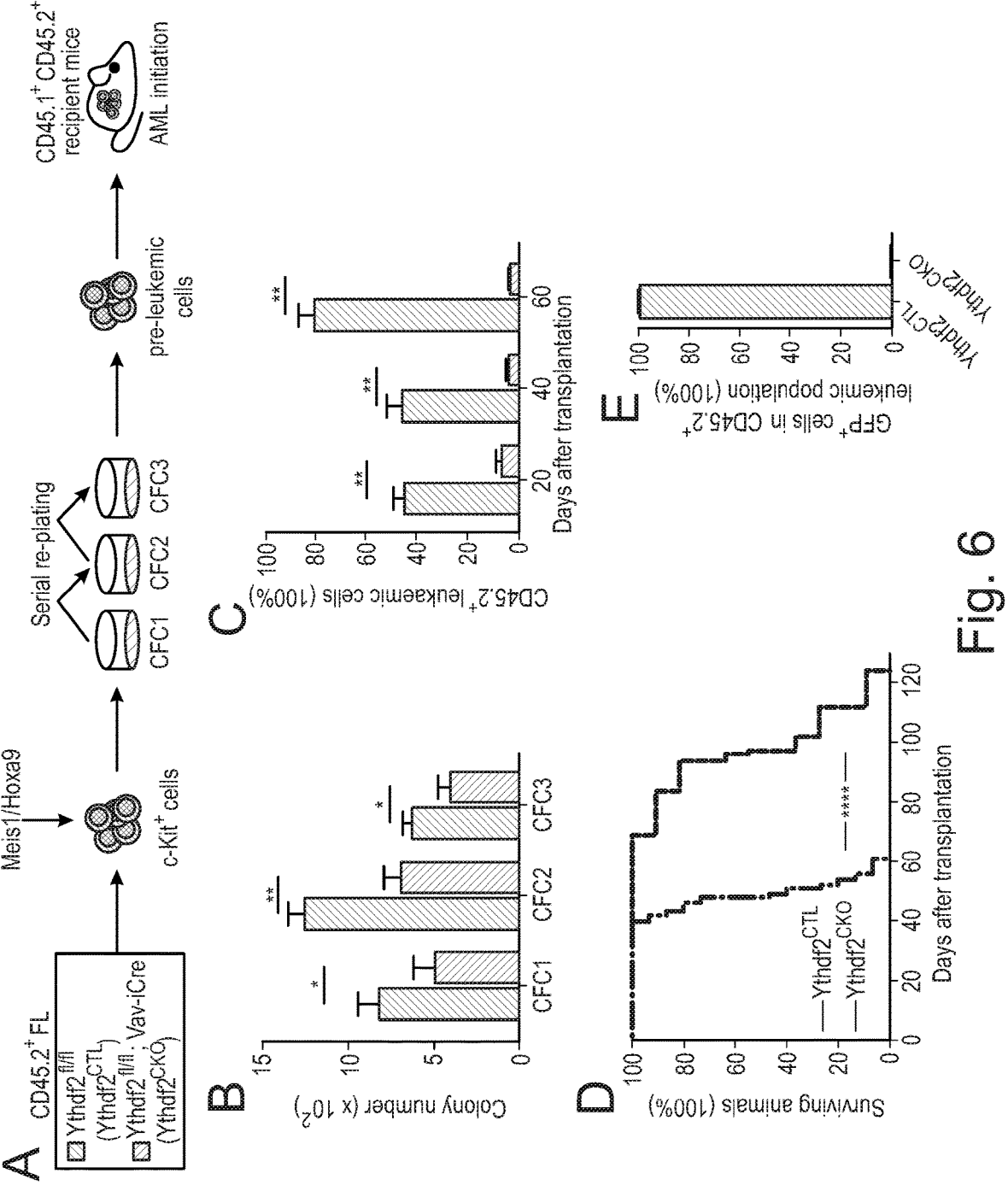
Figure 6:
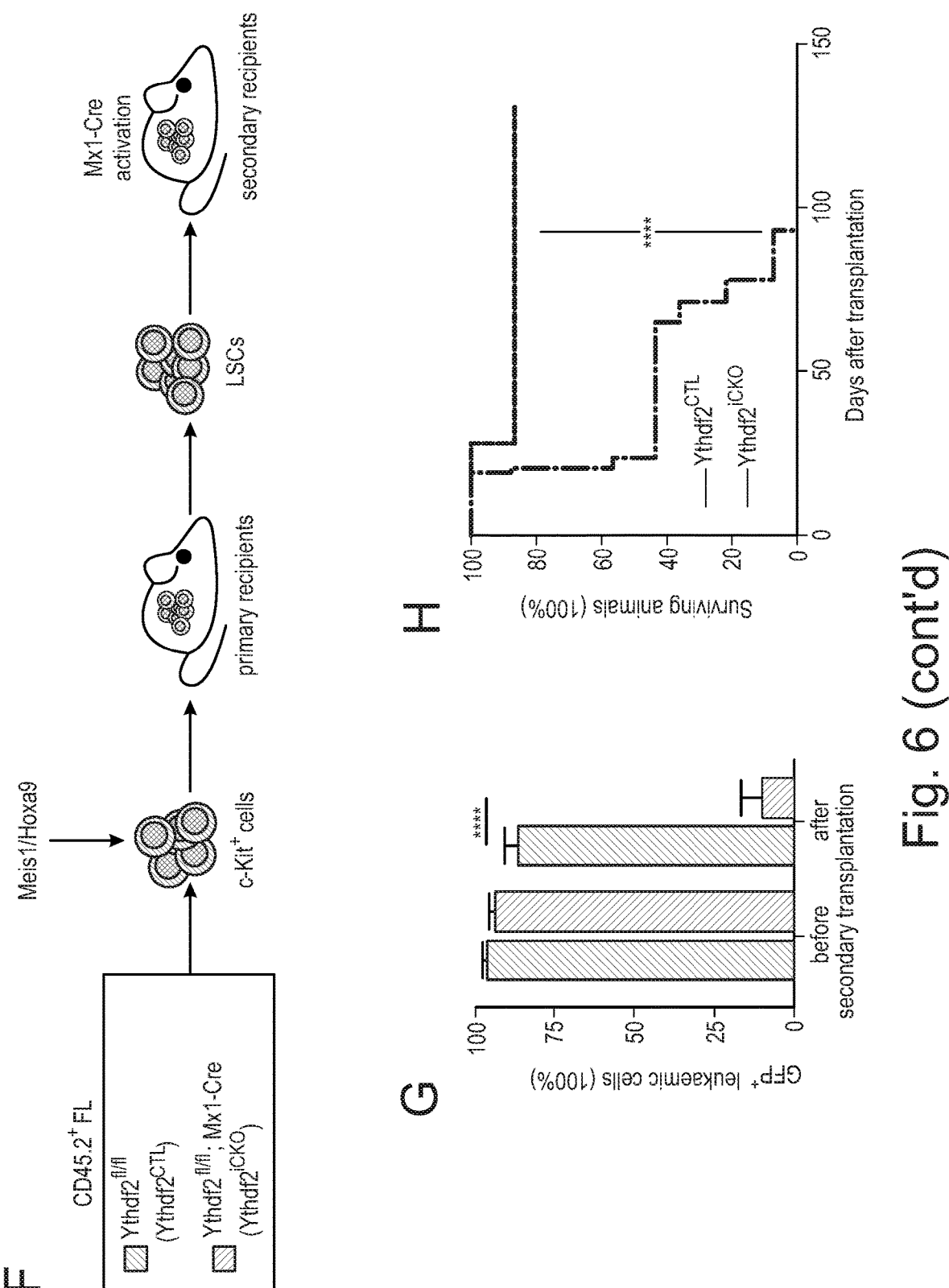

FIG. 6. Ythdf2 inactivation compromises AML initiation and propagation. (A) Control Ythdf2$^{fl/fl}$ (Ythdf2$^{CTL}$) and Ythdf2$^{fl/fl}$; Vav-iCre (Ythdf2$^{CKO}$) FL c-Kit$^{+}$ cells were co-transduced with Meis1 and Hoxa9 retroviruses and serially re-plated. 100,000 c-Kit$^{+}$ pre-leukaemic cells of both genotypes were transplanted into lethally irradiated recipient mice (n=12-14 per genotype) together with 200,000 BM support cells. (B) CFC counts at each re-plating. Data are mean±s.e.m., n=3 per genotype. *, P<0.05; , P<0.01. (C) Percentage of CD45.2$^{+}$ leukaemic cells in the peripheral blood of the recipient mice 20-60 days after transplantation. (n=12-14 per genotype). , P<0.01. (D) Kaplan-Meier survival curve of the recipient mice transplanted with Meis1/ Hoxa9-expressing pre-leukaemic cells. (n=12-14 per genotype), **, P<0.001 Log-rank (Mantel-Cox test). (E) Percentage of GFP-positive cells in the CD45.2$^{+}$ cell population from moribund recipients of Ythdf2$^{CTL}$ and Ythdf2$^{CKO}$ cells (n=5-6). (F) Ythdf2$^{fl/fl}$ (Ythdf2$^{CTL}$) and Ythdf2$^{fl/fl}$; Mx1-Cre (Ythdf2$^{iCKO}$) FL c-Kit$^{+}$ cells were co-transduced with Meis1 and Hoxa9 retroviruses, serially re-plated and transplanted into primary recipient mice, which were left to develop AML. GFP$^{+}$ c-Kit$^{+}$ CD45.2$^{+}$ cells sorted from leukaemic primary recipients were re-transplanted into secondary recipient mice (n=14-16 mice per genotype). (G) Percentage of GFP-expressing cells as a measure of YTHDF2 expression in Ythdf2$^{CTL}$ and Ythdf2$^{iCKO}$ leukaemic cells prior to, and 3 weeks after transplantation. *, P<0.001. (H) Kaplan-Meier survival curve of mice transplanted with Ythdf2$^{CTL}$ and Ythdf2$^{iCKO}$ leukaemic cells. (n=14-16 mice per genotype). ****, P<0.001 Log-rank (Mantel-Cox test).

Figure 7:
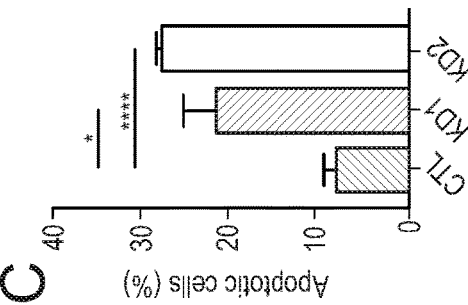
Figure 7:
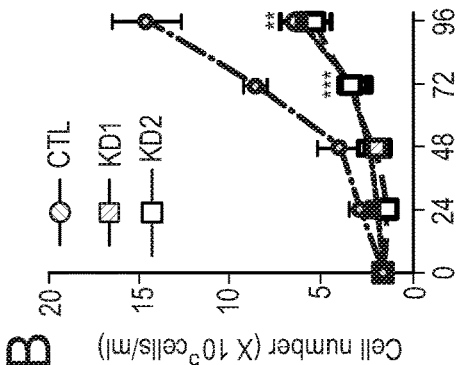
Figure 7:
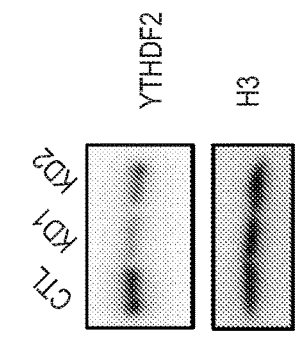
Figure 7:
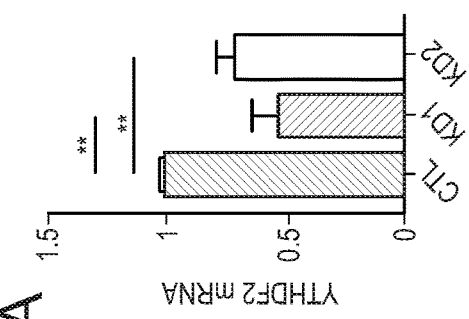
Figure 7:
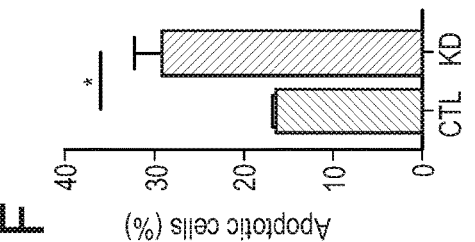
Figure 7:
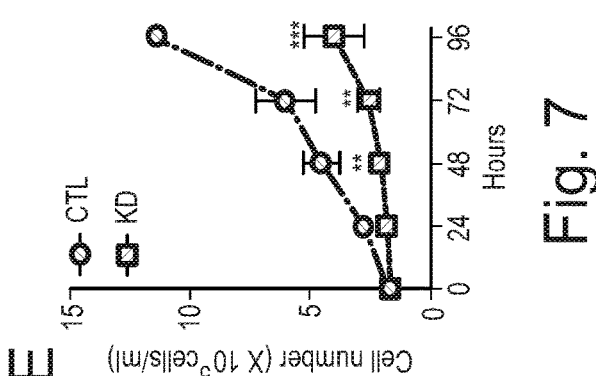
Figure 7:
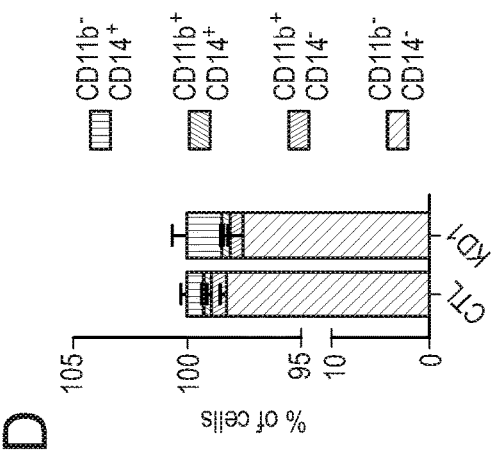
Figure 7:
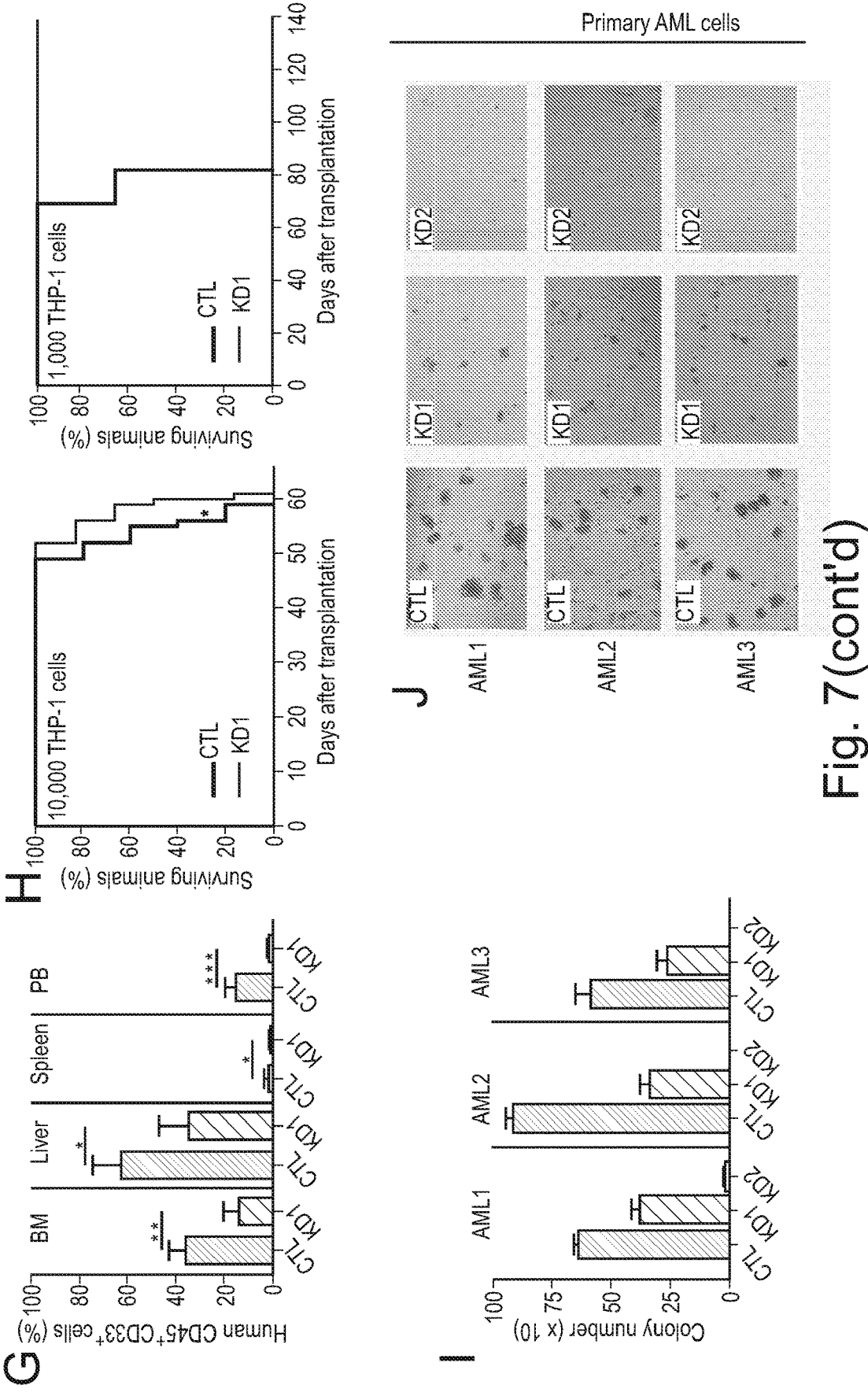

FIG. 7. (A) Relative levels of YTHDF2 mRNA (normalised to ACTB) in human AML THP-1 cells transduced with lentiviruses expressing scrambled shRNA (CTL) and shRNA targeting YHTDF2 (KD). Data are mean±s.e.m., n=3. *, P<0.05. (B) Proliferation assays with THP-1 cells expressing CTL and KD shRNAs. Mean±s.e.m., n=3. , P<0.01; *, P<0.001. (C) Apoptosis assays. The graph depicts the percentage of Annexin V$^{+}$DAPI$^{-}$ cells. Data are mean±s.e.m., n=3. *, P<0.001. (D) Percentage of CD11b$^{-}$ CD14$^{-}$, CD11b$^{+}$CD14$^{-}$, CD11b$^{+}$CD14$^{+}$ and CD11b$^{-}$CD14$^{+}$ cells in cultures shown in FIG. 7B-C. (E) Proliferation assays with NOMO-1 cells expressing CTL and KD shR-NAs. Mean±s.e.m., n=3. , P<0.01; ***, P<0.001. (F) Apoptosis assays. Data are mean±s.e.m., n=3. *, P<0.05. (G) NSG mice were injected with THP-1 cells transduced with CTL (n=4) or KD (n=4) lentiviruses and analysed one month later. Percentage of human CD45$^{+}$CD33$^{+}$ cells in the BM, liver, spleen and PB of the recipient mice is shown. (H) Survival curve of mice transplanted with 10,000 (n=6) and 1,000 (n=3) THP-1 cells. (I) Three independent human primary AML samples (AML1-3) were transduced with CTL, KD1 and KD2 lentiviruses. The graph shows AML-CFC frequencies after 7 days of culture (n=3 technical replicates per sample). (J) Representative colony images from FIG. 7I.

Figure 8:
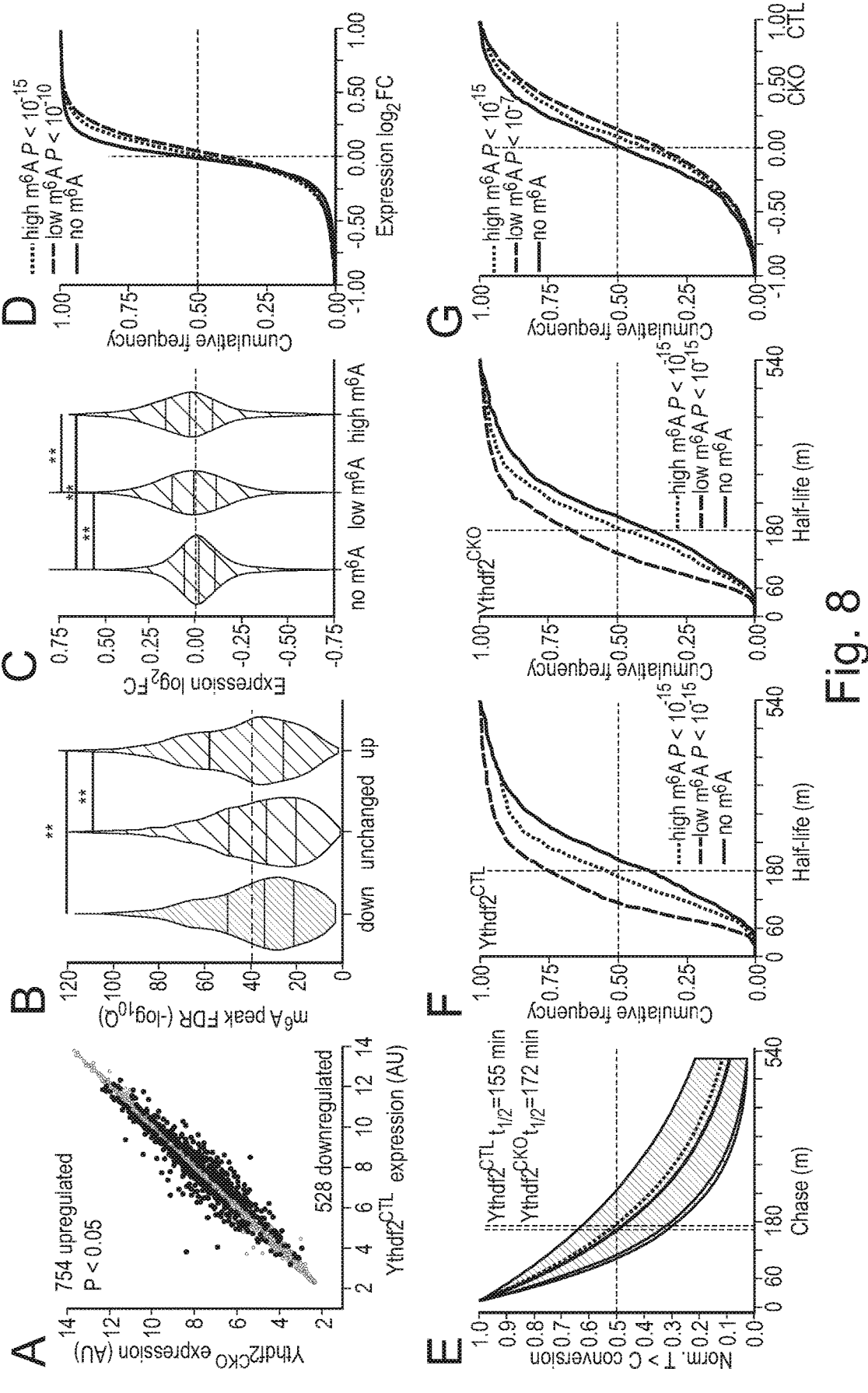
Figure 8:
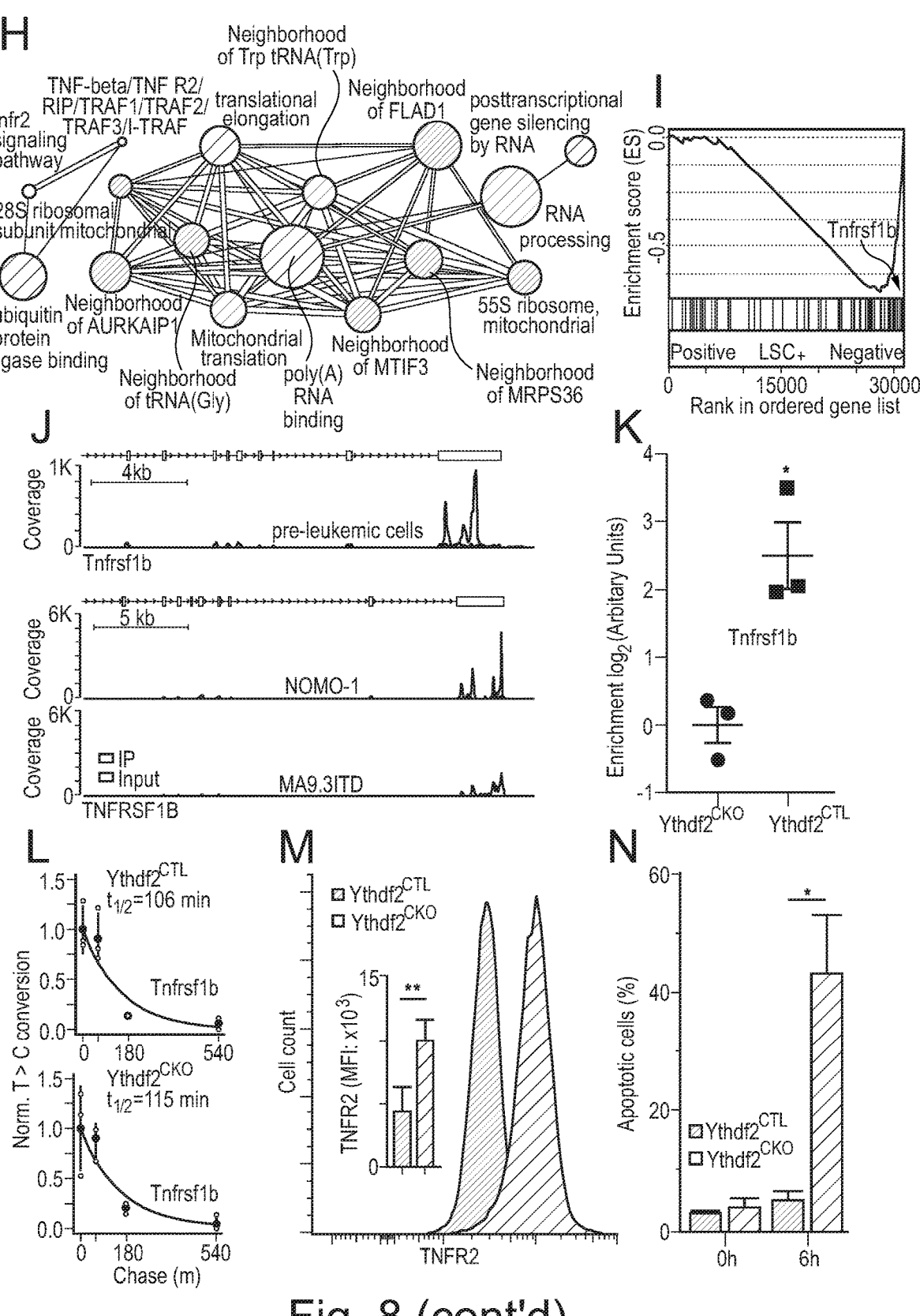

FIG. 8. YTHDF2 loss enhances stability of m$^6$A-modified mRNA in AML. (A) Transcript expression scatter plot from Ythdf2$^{CTL}$ and Ythdf2$^{CKO}$ pre-leukemic cells (n=5). Significantly upregulated or downregulated transcripts are highlighted in red (P<0.05). (B) m$^6$A peak FDR (−log$_{10}$ Q) in Ythdf2$^{CTL}$ pre-leukemic cells for transcripts grouped according to expression changes between Ythdf2$^{CTL}$ and Ythdf2$^{CKO}$ pre-leukemic cells is shown (down, genes significantly downregulated in Ythdf2$^{CKO}$ (P<0.05); unchanged, genes not significantly changing in Ythdf2$^{CKO}$;

up, genes significantly upregulated in Ythdf2$^{CKO}$ (P<0.05). The upper and lower quartiles and the median are shown for each group. (C) Violin plots showing expression change between Ythdf2$^{CTL}$ and Ythdf2$^{CKO}$ pre-leukemic cells for not methylated (no m$^6$A), methylated (m$^6$A, −log$_{10}$ Q≤25) and highly methylated (m$^6$A high, −log$_{10}$ Q>25) transcripts. The upper and lower quartiles and the median are indicated for each group. (D) Cumulative distributions of transcripts' expression change in Ythdf2$^{CTL}$ and Ythdf2$^{CKO}$ pre-leukemic cells for not methylated, methylated and highly methylated transcripts as in C. (E) Mode decay curves for Ythdf2$^{CTL}$ (black) and Ythdf2$^{CKO}$ (red) pre-leukemic cell transcriptomes are shown. The shaded areas indicate the first and third quantile decay curves range for each genotype. Transcripts' half-life modes for each genotype are indicated with horizontal dotted lines and are also shown at the panel top. (F) Cumulative distributions of transcripts' half-life in Ythdf2$^{CTL}$ (left panel) and Ythdf2$^{CKO}$ (right panel) pre-leukemic cells are shown for not methylated, methylated and highly methylated transcripts as in C. The half-life change significance between the methylated and not methylated transcripts are indicated. (G) Cumulative distributions of relative stability change between Ythdf2$^{CTL}$ and Ythdf2$^{CKO}$ pre-leukemic cells are shown for not methylated, methylated and highly methylated transcripts as in C. The relative stability change significances between the methylated and not methylated transcripts are indicated. (H) CPDB analysis of genes significantly upregulated in Ythdf2$^{CKO}$ pre-leukemic cells (P<0.05) with high m$^6$A levels (−log$_{10}$ Q>25) in mouse pre-leukemic cells and also methylated in human AML cell lines. (I) GSEA using LSC signature gene set for genes that negatively correlate with YTHDF2 expression in human AML samples. (J) m$^6$A IP read coverage (blue) from Ythdf2$^{CTL}$ pre-leukemic cells along the Trnfrs1b genomic locus (upper panel) and m$^6$A IP read coverage from NOMO-1, and MA9.3ITD cells along TNFRSF1B genomic locus (lower panels) are shown. Input coverage is shown in green. (K) Tnfrsf1b enrichment in YTHDF2 immuno-precipitates from Ythdf2$^{CTL}$ pre-leukemic cells is shown. Tnfrsf1b background levels were determined using Ythdf2$^{CKO}$ pre-leukemic cells (n=3). (L) Decay curves for Trnfrs1b in Ythdf2$^{CTL}$ (top panel) and Ythdf2$^{CKO}$ (bottom panel) pre-leukemic cells transcriptomes are shown. The centre value and the error bars at each time point indicate the conversion rate mean and standard deviation, respectively. The conversion rates for each biological replicate are indicated with dots. The Trnfrs1b half-life is also shown. (M) FACS plots showing the expression of TNFR2 on the cell surface of Ythdf2$^{CTL}$ and Ythdf2$^{CKO}$ pre-leukemic cells. The inner graph displays the quantification of TNFR2 expression (n=4). (N) Percentage of Annexin V$^{+}$DAPI$^{-}$ pre-leukemic cells treated with TNF-α at 0 and 6-hour timepoints (n=3). *, P<0.05; **, P<0.01

EXAMPLES

Example 1. The Expression of YTHDF2 at Different Levels of Haematopoietic Hierarchy To determine YTHDF2 expression in the haematopoietic system, we employed mice in which eGFP-PreScission-His6-Flag-HA2 tag is inserted after the start codon of YTHDF2 (creating a functional fusion protein), and additionally exon 2 of Ythdf2 is flanked by LoxP sites (FIG. 1A) (Ivanova et al., Mol Cell. 67(6): 1059-1067 e1054, 2017). All the details regarding these mice are described in Ivanova et al. (ibid). In these mice, eGFP fluorescence reports endogenous YTHDF2 protein levels, which can be detects by flow cytometry.

We produced adult mice (by inter-crossing the above mice) and 14.5 days postcoitum (dpc) embryos and obtained 14.5 days postcoitum (dpc) embryos and obtained bone marrow cells (BM) and foetal liver (FL; the major site of definitive haematopoiesis during development) cells using standard protocols as previously described (Mortensen et al., J Exp Med. 208(3): 455-467, 2011; Vukovic et al., J Exp Med. 212(13):2223-2234, 2015; Vukovic et al., Blood. 127(23): 2841-2846, 2016; Guitart et al., J Exp Med. 214(3): 719-735, 2017).

Using staining procedures (Mortensen et al., J Exp Med. 208(3): 455-467, 2011, Vukovic et al., Blood. 127(23): 2841-2846, 2016) with defined antibodies recognising cell surface antigens (Lineage markers, Sca-1, c-Kit$^+$, CD150 and CD48), we performed FACS acquisitions of BM and FL Lin$^-$Sca-1$^+$c-Kit$^+$ (LSK) cells, LSKCD48$^-$CD150$^+$ HSCs, LSKCD48$^-$CD150$^-$ multipotent progenitors (MPPs), primitive haematopoietic progenitor cells (i.e. LSKCD48$^+$CD150$^-$ HPC-1 and LSKCD48$^+$CD150$^+$ HPC-2 populations), and Lin$^-$Sca-1$^-$c-Kit$^+$ (LK) myeloid progenitors, and Lin$^+$ cells, and determined GFP expression in these cells using flow cytometry (FACS).

The data for each population were calculated as mean fluorescence intensity of GFP expression in each population using FlowJo software (FlowJo Llc).

Figure 1:
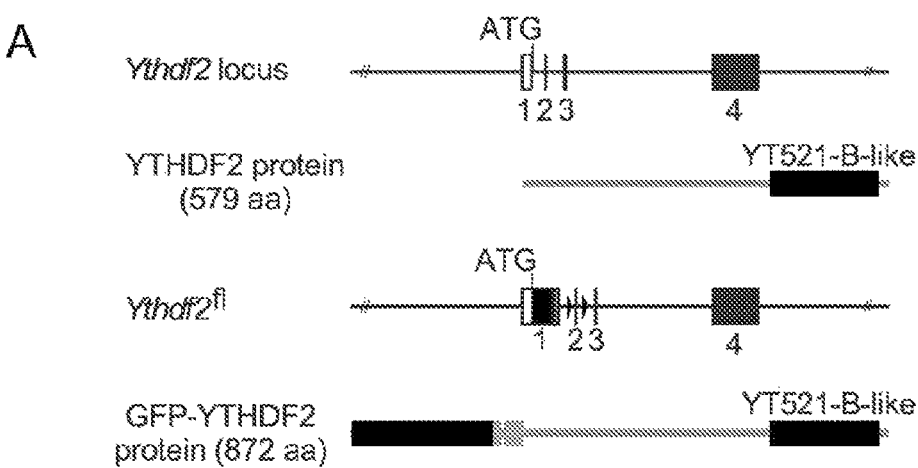
FIG. 1. YTHDF2 expression within the haematopoietic system.
Figure 1:
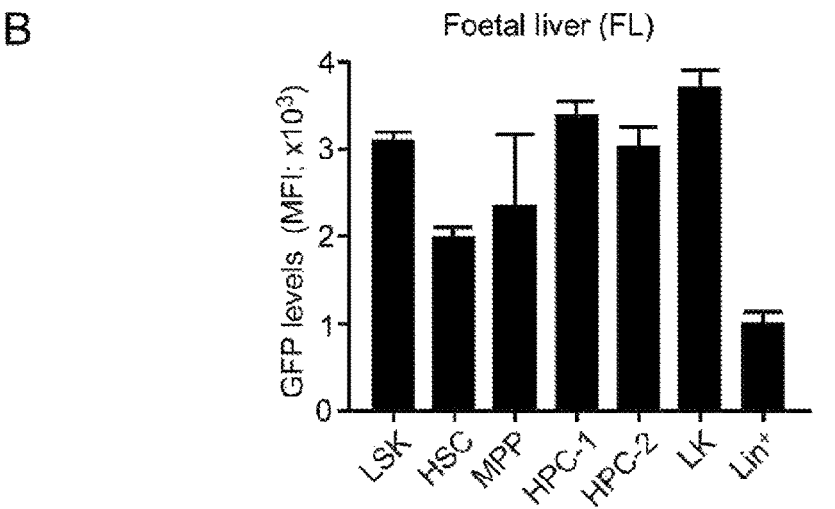
Figure 1:
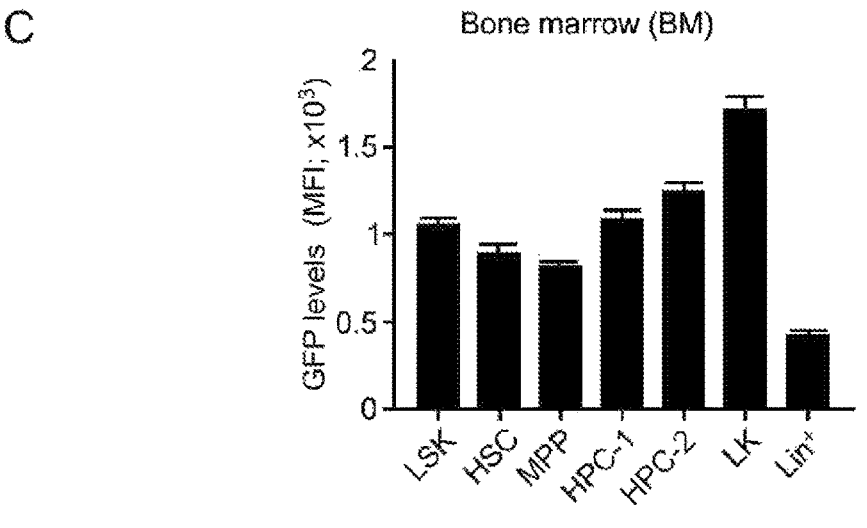

All hematopoietic cells in FL and adult BM expressed GFP-YTHDF2 (FIGS. 1B and 1C). Notably, YTHDF2 was highly expressed in Lin$^-$Sca-1$^+$c-Kit$^+$ (LSK) cells, LSKCD48$^-$CD150$^+$HSCs, LSKCD48$^-$CD150$^-$ multipotent progenitors (MPPs), primitive hematopoietic progenitor cells (i.e. LSKCD48$^+$CD150$^-$ HPC-1 and LSKCD48$^+$CD150$^+$ HPC-2 populations), and Lin$^-$Sca-1$^-$c-Kit$^+$ (LK) myeloid progenitors, and its expression was decreased in differentiated Lin$^+$ cells (FIGS. 1B and 1C).

These results indicated that YTHDF2 protein is highly expressed in stem and progenitor cells and its expression is decreased in more mature haematopoietic cells.

Example 2. The Impact of Ythdf2 Deletion on Numbers of Foetal Liver (FL) and Adult Stem and/or Primitive Progenitor Cells To reveal the role of YTHDF2 in HSC biology and multilineage haematopoiesis, we conditionally deleted Ythdf2 specifically from the haematopoietic system shortly after the emergence of definitive HSCs using Vav-iCre (de Boer et al., Eur J Immunol. 33(2): 314-325, 2003). To achieve this, we mated adult Ythdf2$^{fl/fl}$ mice as described in Ivanova et al., (ibid) with adult Vav-iCre mice as described in de Boer et al., (ibid).

We next performed timed matings (as described in Bamforth et al., Nat Genet. 29(4): 469-474, 2001, Kranc et al., Mol Cell Biol. 23(21): 7658-7666, 2003, Guitart et al., J Exp Med. 214(3): 719-735, 2017)) to generate Ythdf2$^{fl/fl}$; Vav-iCre (referred to as Ythdf2$^{cKO}$ or Ythdf2$^{CKO}$) and control (referred to as Ythdf2$^{CTL}$) embryos at 14.5 days dpc. FACS analyses of FL cells indicated that Ythdf2$^{cKO}$ cells from FLs did not express the YTHDF2 protein indicating that Ythdf2$^{cKO}$ cells have lost YTHDF2 expression (FIG. 2A-C).

We next determined the frequencies and absolute numbers of HSCs and primitive progenitors in FLs using FACS analyses as previously described (Guitart et al., J Exp Med. 214(3): 719-735, 2017). We found that FLs of Ythdf2$^{cKO}$ embryos displayed significantly increased frequencies and absolute numbers of HSCs and primitive progenitors compared to control FLs (FIG. 2D-E). Therefore, loss of YTHDF2 expression results in enhanced expansion of HSCs and primitive cells within FL.

To rule out compensatory mechanisms resulting from Vav-iCre-mediated-recombination during embryonic hematopoiesis, we employed Mx1-Cre, which upon plpC injection, acutely deletes Ythdf2 in Ythdf2$^{iCKO}$ adult mice (FIG. 2F). Acute Ythdf2 deletion (FIG. 2G) had no impact on mouse survival (data not shown) or multilineage hematopoiesis (FIG. 2H-l)) and resulted in increased numbers of BM LSK cells but not LK myeloid progenitor cells (FIG. 2J). Thus, Ythdf2 hematopoietic-specific ablation during development or acute deletion in the adult mouse leads to an expansion of the primitive cell compartment at the top of the hematopoietic differentiation hierarchy and does not derail normal hematopoiesis.

Example 3. Transplantation of Ythdf2-Deficient HSCs into Primary Recipient Mice We employed long-term competitive transplantation assays (FIG. 3A) to determine the reconstitution and self-renewal capacity of FL Ythdf2-deficient and control HSCs. To achieve this, we used standard transplantation protocols as previously described (Guitart et al., J Exp Med. 214(3): 719-735, 2017).

Lethal irradiation of CD45.1$^+$/CD45.2$^+$ recipient mice was achieved using a split dose of 11 Gy (two doses of 5.5 Gy administered at least 4 h apart) at a mean rate of 0.58 Gy/min using a Cesium 137 irradiator (GammaCell 40; Best Theratronics).

For primary transplantations, 100 HSCs (LSKCD48$^-$CD150$^+$CD45.2$^+$) sorted from FLs of 14.5-dpc embryos or 200,000 unfractionated FL cells were mixed with 200,000 support CD45.1$^+$ BM cells and injected into lethally irradiated (11 Gy delivered in a split dose) CD45.1$^+$/CD45.2$^+$ recipient mice.

Peripheral blood analyses (described previously (Guitart et al., J Exp Med. 214(3): 719-735, 2017)) indicated that Ythdf2-deficient HSCs gave equal overall long-term reconstitution compared to control HSCs for at least 16 weeks after transplantation (FIGS. 3B and 3C). However, while Ythdf2-deficient HSCs had slightly enhanced myeloid lineage reconstitution capacity compared to control HSCs, they had normal B-cell and slightly compromised T-cell reconstitution potentials (FIGS. 3B and 3C).

Notably, FACS analyses of BM of recipient mice 16 weeks after transplantation (which employed previously described approaches (Mortensen et al., J Exp Med. 208(3): 455-467, 2011, Guitart et al., Blood. 122(10): 1741-1745, 2013, Vukovic et al., Blood. 127(23): 2841-2846, 2016, Guitart et al., J Exp Med. 214(3): 719-735, 2017)) demonstrated that HSCs lacking Ythdf2 displayed enhanced contribution to the HSC/primitive progenitor cell compartments of the recipient mice (FIG. 3D) and reconstituted normal BM haematopoiesis (FIG. 3E).

Example 4. Transplantation of Ythdf2-Deficient FL HSCs into Secondary Recipient Mice To test the self-renewal capacity of Ythdf2-deficient HSCs, we culled the primary recipients, isolated BM cells and sorted stem and progenitor cells from the primary recipient mice. 2,000 CD45.2$^+$ LSK cells sorted from BM of primary recipients were mixed with 200,000 support CD45.1$^+$ wild-type BM cells and re-transplanted into secondary recipients (Mortensen et al., J Exp Med. 208(3):

455-467, 2011, Guitart et al., Blood. 122(10): 1741-1745, 2013, Vukovic et al., Blood. 127(23): 2841-2846, 2016, Guitart et al., J Exp Med. 214(3): 719-735, 2017).

FACS analyses of BM of the recipient mice (16 weeks after transplantation) revealed that Ythdf2-deficient HSCs had increased ability to reconstitute all haematopoietic compartments of the secondary recipient mice, compared to control HSCs (FIG. 3F-G), Therefore, Ythdf2 deletion promotes HSC and primitive progenitor cell expansion and enhances their reconstitution capacity.

Example 5. Analyses of Adult Mice Lacking Ythdf2 Specifically from the Haematopoietic System We next investigated the impact of Ythdf2 deletion on adult haematopoiesis and HSC functions. We mated $Ythdf2^{fl/fl}$ mice to $Ythdf2^{fl/fl}$; Vav-iCre mice to generate $Ythdf2^{CKO}$ and control mice. $Ythdf2^{CKO}$ mice were born at normal Mendelian ratios, matured to adulthood without any obvious defects (as defined by their survival, appearance and daily monitoring of their behaviour). Furthermore, FACS analyses (using protocols we previously described (Kranc et al., Cell Stem Cell. 5(6): 659-665, 2009, Vukovic et al., Blood. 127(23): 2841-2846, 2016, Guitart et al., J Exp Med. 214(3): 719-735, 2017) revealed that they had normal multilineage haematopoiesis (FIG. 4A).

Colony-forming cell (CFC) assays in GM 3434 medium (from Stemcell Technologies), as described previously (Kranc et al., Cell Stem Cell. 5(6): 659-665, 2009) indicated normal differentiation potential of BM cells lacking Ythdf2 (FIG. 4B). Thus, despite the modest changes in the peripheral blood upon Ythdf2 deletion, we conclude that YTHDF2 is not critical for steady-state hematopoiesis.

Notably, FACS analyses (using our standard approaches (Kranc et al., Cell Stem Cell. 5(6): 659-665, 2009, Guitart et al., Blood. 122(10): 1741-1745, 2013, Vukovic et al., Blood. 127(23): 2841-2846, 2016, Guitart et al., J Exp Med. 214(3): 719-735, 2017)) of adult $Ythdf2^{CKO}$ mice indicated that they displayed expansion of BM HSCs and primitive (HPC-1 and HPC-2) progenitor cells compared to $Ythdf2^{CTL}$ mice (FIG. 4C).

Example 6. Analyses of HSCs and Progenitor Cells in Adult Ythdf2-Deficient Mice Treated with 5-Fluorouracil We next examined the consequences of Ythdf2 deletion on HSC responses to haematopoietic injury, by subjecting $Ythdf2^{CKO}$ and $Ythdf2^{CTL}$ mice to serial injections of the myelosuppressive agent 5-fluorouracil (5-FU), which depletes cycling haematopoietic cells and forces HSCs to proliferate and self-renew.

8-10 weeks old $Ythdf2^{CKO}$ and $Ythdf2^{CTL}$ mice received 3 sequential doses of 5-FU (150 mg/kg; 25-30 days apart) and were analysed 30 days after the last 5-FU administration. BM analyses (carried out as described previously (Guitart et al., Blood. 122(10): 1741-1745, 2013, Vukovic et al., Blood. 127(23): 2841-2846, 2016)) indicated that 5-FU-treated $Ythdf2^{CKO}$ mice displayed strikingly increased numbers of HSCs and primitive progenitors compared to control mice (FIG. 4D).

Example 7. Analyses of Reconstitution Capacity of Adult Ythdf2-Deficient HSCs To reveal the repopulation capacity of Ythdf2-deficient HSCs, we transplanted 200 CD45.2$^+$ HSCs sorted from BM of $Ythdf2^{CKO}$ and $Ythdf2^{CTL}$ mice (as we described previously (Guitart et al., Blood. 122(10): 1741-1745, 2013, Vukovic et al., Blood. 127(23): 2841-2846, 2016, Guitart et al., J Exp Med. 214(3): 719-735, 2017)) into lethally irradiated syngeneic CD45.1$^+$/CD45.2$^+$ recipients (together with competitor BM cells obtained from CD45.1$^+$ mice), using our standard transplantation protocols as descried in (Guitart et al., Blood. 122(10): 1741-1745, 2013, Vukovic et al., Blood. 127(23): 2841-2846, 2016, Guitart et al., J Exp Med. 214(3): 719-735, 2017). FACS analyse revealed that Ythdf2-deficient HSCs displayed significantly increased capacity to contribute to the HSC, MPP, HPC-1 and HPC-2 compartments (FIG. 4E) and differentiated cell compartments (FIG. 4F) of the recipient mice compared to control HSCs, indicating that Ythdf2-deficient HSCs outcompeted control HSCs and displayed enhanced reconstitution capacity. Therefore, targeting Ythdf2 promotes HSC expansion, and enhances their reconstitution and regenerative capacity.

These data taken together suggest that YTHDF2 can be a therapeutic target for ex vivo HSC expansion or enhancing regenerative capacity of HSCs upon chemotherapy or transplantation.

Example 8. The Role of YTHDF2 in AML

To determine the expression of YTHDF2 in different AML samples, we used the following publicly available datasets:

| Dataset | # samples | Reference |
|---------|-----------|-----------|
| GSE52891 | 18 | (Bachas et al., PLoS One. 10(4): e0121730, 2015) |
| GSE61804 | 160 | (Metzelder et al., Leukaemia. 29(7): 1470-1477, 2015) |
| GSE12417 | 73 | (Metzeler et al., Blood. 112(10): 4193-4201, 2008) |
| GSE13159 | 576 | (Haferlach et al., J Clin Oncol. 28(15): 2529-2537, 2010) |
| GSE15061 | 505 | (Mills et al., Blood. 114(5): 1063-1072, 2009) |
| GSE15434 | 54 | (Klein et al., BMC Bioinformatics. 10(422, 2009) |
| GSE16015 | 65 | (Haferlach et al., Blood. 114(14): 3024-3032, 2009) |
| GSE19577 | 40 | (Pigazzi et al., Leukaemia. 25(3): 560-563, 2011) |
| GSE22845 | 45 | (Taskesen et al., Blood. 117(8): 2469-2475, 2011) |
| GSE10358 | 99 | (Tomasson et al., Blood. 111(9): 4797-4808, 2008) |

Affymetrix data were downloaded as raw CEL files from the GEO database. Only bone marrow samples, with a total of 1732 samples (11 datasets), were used for analysis. The Simpleaffy package from Bioconductor was used to extract quality measurement of microarrays. RNA degradation was assessed through GAPDH and ACTB housekeeping genes. Samples with NUSE<1.05 and relative log expression (RLE)<0.15 were excluded from further analysis. Finally, the retained samples were assessed for their homogeneity using the Bioconductor array QualityMetrics package. Low quality RNA and outlier samples were excluded from further analysis. High quality samples retained after quality control were background corrected and normalized using RMAexpress software (http://rmaexpress.bmbolstad.com/). Pairwise comparisons between each karyotype and control were performed using student t-test. Adjustment for multiple comparisons was done using Benjamini and Hochberg.

ANOVA test was used for multiclass comparisons. Figures were created using R/Bioconductor package "ggplot2".

The analyses of these global gene expression datasets of different AML samples revealed that the expression of YTHDF2 was significantly higher across the AML samples with diverse cytogenetic abnormalities compared to non-leukaemic controls (FIG. 5A). This was corroborated by western blotting, which demonstrated that YTHDF2 is highly expressed in patient-derived AML samples (FIG. 5B).

For western blotting shown in FIG. 5B, the following samples were used: 70 (karyotype 46,XY,del(7)(q22q32) [20]), 104 (karyotype 46,XX,t(6; 9; 11)(p2?1; p22; q23)[6]/45,idem,der(15)t(15; 17)(p11.2; q11.2),−17[4] [variant of t(9; 11)]0, 108 (karyotype 46,XX,t(6; 11)(q27; q23)[10]), 149 (karyotype 46,XX,t(15; 17)(q22; q11.2)[7]/46,sl,−6,add (16)(q12),+mar[3]/46,XX[3]), 163 (karyotype 45,X,−Y,t(8; 21)(q22; q22)[8]/46,XY[2]), 191 (karyotype 46,XX [20]), 205 (karyotype 44,XX,add(3)(p25),−5,−7[12]), 419 (karyotype 46,XX,t(1; 22)(p21; p11.2),ins(10; 11)(p12; q23q1?4) [10] nb variant of t(10; 11) MLL-MLLT10 fusion), 539 (karyotype 46,XY [20]), 685 (karyotype 46,XX,t(6; 9)).

Using the analyses described above, we next compared YTHDF2 expression in publicly available datasets (Ng et al., Nature. 540(7633): 433-437, 2016) from AML primitive cell compartments which gave rise to leukaemia upon xeno-transplantation and the equivalent AML cell compartments which failed to initiate leukaemia. These in silico analyses showed that LSC activity correlated with increased YTHDF2 expression (FIG. 5C). Thus, YTHDF2 expression is increased in LSCs compared to cells which do not possess the LSC activity.

Furthermore, given that the majority of CD34$^+$ and a minority of CD34$^−$ fractions have LSC activity (Eppert et al., Nat Med 17:1086-1093, 2011; Ng et al., Nature. 540 (7633): 433-437, 2016; Sarry et al., J Clin Invest 121:384-395, 2011), we also compared YTHDF2 expression between these fractions and found that YTHDF2 was expressed at higher levels in CD34$^+$ fractions of AML samples (FIG. 5D).

These data indicate that YTHDF2 expression level can be a biomarker for diseases that can be treated with a YTHDF2 inhibitor.

Example 9. The Role of YTHDF2 in Leukaemic Transformation In Vitro

To investigate the functional requirement for YTHDF2 in leukemogenesis we employed conditional genetics and a mouse model of AML in which Meis1 and Hoxa9, onco-genes frequently overexpressed in human AML subtypes (Lawrence et al., Leukaemia. 13(12): 1993-1999, 1999, Drabkin et al., Leukaemia. 16(2): 186-195, 2002), drive the development and maintenance of LSCs. We have previously described this model and the protocol in detail (Vukovic et al., J Exp Med. 212(13):2223-2234, 2015, Guitart et al., J Exp Med. 214(3): 719-735, 2017).

In this model (FIG. 6A), HSPCs (c-Kit$^+$ cells) were sorted from FLs of 14.5-dpc embryos after c-Kit (CD117) enrich-ment using magnetic-activated cell-sorting columns (Milte-nyi Biotec). 10,000 cells were simultaneously transduced with mouse stem cell virus (MSCV)-Meis1a-puro and MSCV-Hoxa9-neo retroviruses and subsequently subjected to three rounds of CFC assays in MethoCult (M3231) supplemented with 20 ng/ml stem cell factor, 10 ng/ml IL-3, 10 ng/ml IL-6, and 10 ng/ml granulocyte/macrophage stem cell factor.

Colonies were counted 6-7 d after plating, and 2,500 cells were replated. Serial replating generates pre-leukaemic cells, which upon transplantation to recipient mice give rise to self-renewing LSCs causing AML (Kroon et al., EMBO J. 17(13): 3714-3725, 1998, Wang et al., Science. 327 (5973): 1650-1653, 2010, Velasco-Hernandez et al., Blood. 2014, Vukovic et al., J Exp Med. 212(13):2223-2234, 2015, Guitart et al., J Exp Med. 214(3): 719-735, 2017).

We mated Ythdf2$^{fl/fl}$ mice (as described by Ivanova et al., ibid; in which GFP is inserted after the start codon of Ythdf2 and exon 2 of Ythdf2 is flanked by LoxP sites) with the Vav-iCre deleter (de Boer et al., Eur J Immunol. 33(2): 314-325, 2003) which recombines specifically within the haematopoietic system. Timed matings of Ythdf2$^{fl/fl}$ with Ythdf2$^{fl/fl}$; Vav-iCre Ythdf2$^{CKO}$ mice gave rise to Ythdf2$^{fl/fl}$; Vav-iCre (Ythdf2$^{CKO}$) and control Ythdf2$^{fl/fl}$ or (Ythdf2$^{CTL}$) embryos. We observed at weaning normal Mendelian dis-tribution of Ythdf2$^{CTL}$ and Ythdf2$^{CKO}$ mice (i.e. Ythdf2$^{fl/fl}$ X Ythdf2$^{fl/fl}$; Vav-iCre matings resulted in 65 Ythdf2$^{CTL}$ and 47 Ythdf2$^{CKO}$ mice at weaning, P=0.28) and found no increased mortality of Ythdf2$^{CKO}$ mice thereafter.

Fetal liver (FL) HSPC were prepared from these embryos as previously described (Guitart et al., J Exp Med. 214(3): 719-735, 2017). We subsequently transduced FL HSPCs with Meis1/Hoxa9 retroviruses (FIG. 6A), as per protocol described above. While Ythdf2$^{CKO}$ cells produced signifi-cantly lower numbers of colonies upon serial re-plating (FIG. 6B).

Thus, we found that Ythdf2$^{CKO}$ cells produced signifi-cantly lower numbers of colonies upon serial re-plating (FIG. 6B). These results indicated that Ythdf2$^{CKO}$ have compromised ability to undergo leukaemic transformation.

Example 10. The Role of YTHDF2 in AML Initiation

To test the ability of Ythdf2$^{CKO}$ and Ythdf2$^{CTL}$ pre-leukaemic cells (i.e. cells produced in 3 rounds of serial re-plating, as previously described (Vukovic et al., J Exp Med. 212(13):2223-2234, 2015; Guitart et al., J Exp Med. 214(3): 719-735, 2017), to generate AML upon transplan-tation (FIG. 6A), we transplanted them into recipient mice as we described previously (Vukovic et al., 2015, ibid; Guitart et al., 2017 ibid). The monitoring and analyses of these mice (according to standard protocols described in (Vukovic et al., 2015, ibid; Guitart et al., 2017 ibid), demonstrated that Ythdf2-deficient pre-leukaemic cells generated AML with substantially longer disease latency compared to control cells (FIG. 6C-D). The loss of YTHDF2 expression was confirmed in Ythdf2$^{CKO}$ cells isolated from moribund recipi-ent mice based of the lack of the GFP expression (FIG. 6E), excluding the possibility that the disease with the delayed latency is caused by the accumulation of cells which escaped Ythdf2 deletion. Therefore, Ythdf2 is required for LSC development and disease initiation in AML driven by Meis1/Hoxa9.

Example 11. The Role of YTHDF2 in AML Propagation

We next asked whether acute deletion of Ythdf2 from established LSCs using Mx1-Cre impacts on LSC mainte-nance and leukaemia propagation. To achieve this, we crossed adult Ythdf2$^{fl/fl}$ mice (described in Ivanova et al., ibid) with Mx1-Cre mice (described in (Kuhn et al., Science. 269(5229): 1427-1429, 1995)) in which Cre expression is induced by interferon. By performing timed matings as described (Guitart et al., J Exp Med. 214(3): 719-735, 2017), we generated 14.5 dpc Ythdf2$^{fl/fl}$; Mx1-Cre (Ythdf2$^{iKO}$) and control Ythdf2$^{fl/fl}$ (Ythdf2$^{CTL}$) embryos and extracted FL HSPCs from them using c-Kit enrichment (by employing magnetic-activated cell-sorting columns (Miltenyi Biotec)).

Using the Meis1/Hoxa9 mouse AML model described above (Examples 9 and 10), we next transduced HSPCs with Meis1/Hoxa9 retroviruses and transplanted them into lethally irradiated primary recipient mice (FIG. 6F). Upon leukaemia development (determined by the presence of leukaemic cells in peripheral blood using FACS) the mice were culled and BM cell suspensions were generated as we previously described (Kranc et al., Cell Stem Cell. 5(6): 659-665, 2009; Guitart et al., Blood. 122(10): 1741-1745, 2013; Vukovic et al., J Exp Med. 212(13):2223-2234, 2015; Vukovic et al., Blood. 127(23): 2841-2846, 2016; Guitart et al., J Exp Med. 214(3): 719-735, 2017).

c-Kit$^+$ cells (a population enriched for LSCs) were isolated from BM using magnetic-activated cell-sorting columns (Miltenyi Biotec). Given the leakiness of Mx1-Cre upon transplantation (i.e. Cre can be induced even without interferon administration) (Velasco-Hernandez et al., Stem Cell Reports. 7(1): 11-18, 2016), the population was further sorted for GFP$^+$ cells to enrich for those expressing GFP-YTHDF2 protein (FIG. 6G, before secondary transplantation). GFP$^+$ cell sorting was performed on a FACSAria Fusion cell sorter (BD). 100,00 of c-Kit$^+$ cells GFP$^+$ were re-transplanted into secondary recipients using protocols described previously (Vukovic et al., J Exp Med. 212(13): 2223-2234, 2015; Guitart et al., J Exp Med. 214(3): 719-735, 2017).

While Ythdf2$^{CTL}$ c-Kit$^+$ GFP$^+$ cells caused aggressive AML upon transplantation to secondary recipients (FIG. 6H), Ythdf2$^{iKO}$ c-Kit$^+$GFP$^+$ cells lost YTHDF2 expression (FIG. 6G, after secondary transplantation) due to spontaneous Mx1-Cre activation upon LSC transplantation (even without the administration of polyinosinic-polycytidylic acid; plpC) (Velasco-Hernandez et al., Stem Cell Reports. 7(1): 11-18, 2016), and failed to efficiently propagate the disease (FIG. 6H). Thus, YTHDF2 is required for disease propagation in Meis1/Hoxa9 model of AML.

Example 12. The Role of YTHDF2 in Human AML Cell Line with MLL Translocation To investigate the requirement for YTHDF2 in human established leukaemic cells, we knocked down the expression of YTHDF2 in human AML THP-1 cells harbouring MLL-AF9 translocation using shRNA approaches as we previously described (Karvela et al., Autophagy. 12(6): 936-948, 2016, Sinclair et al., Blood. 128(3): 371-383, 2016, Guitart et al., J Exp Med. 214(3): 719-735, 2017). The sequences of shRNA targeting human YTHDF2 were:

```
(KD1)
                              (SEQ ID NO: 3)
CCGGTACTGATTAAGTCAGGATTAACTCGAGTTAATCCTGACTTAATCAG
TATTTTTG (KD2)
                              (SEQ ID NO: 4)
CCGGCGGTCCATTAATAACTATAACCTCGAGGTTATAGTTATTAATGGAC
CGTTTTTG
```

THP-1 cells were cultured at 400,000 cells/ml in RPMI-1640 GlutaMAX containing 10% FBS, 25 mM HEPES, 100 U/ml penicillin, and 100 µg/ml streptomycin. Lentiviruses were prepared and THP-1 cells were transduced as we previously described (Kranc et al., Cell Stem Cell. 5(6): 659-665, 2009; Vukovic et al., J Exp Med. 212(13):2223-2234, 2015). Transduced THP-1 cells were grown in the presence of 5 µg/ml puromycin. Knockdown efficiency (e.g. YTHDF2 gene expression) was determined using RT-quantitative PCR as we previously described (Kranc et al., Cell Stem Cell. 5(6): 659-665, 2009, Sinclair et al., Blood. 128(3): 371-383, 2016, Guitart et al., J Exp Med. 214(3): 719-735, 2017).

Efficient YTHDF2 knockdown was validated by Q-PCR and western blotting (FIG. 7A), as previously described (Guitart et al., J Exp Med. 214(3): 719-735, 2017). We next performed cell proliferation assays by measuring cell numbers by flow cytometry using the Accuri C6 Flow Cytometer (BD) as described (Vukovic et al., J Exp Med. 212(13): 2223-2234, 2015). Apoptosis of THP-1 cells with YTHDF2 knockdown was determined by staining with Annexin V-FITC and DAPI followed by FACS analysis. Percentage of Annexin V$^+$DAPI$^-$ cells (% of apoptotic cells) was calculated using FlowJo software. Notably, we found that YTHDF2 knockdown (FIG. 7A) inhibited THP-1 cell growth and increased their apoptosis (FIG. 7B-C) but had no impact on their myeloid differentiation status (FIG. 7D). This finding was corroborated in NOMO-1 AML cells harbouring MLL-AF9 translocation (FIG. 7E-F). Furthermore, THP-1 cells with YTHDF2 knockdown had decreased capacity to engraft AML compared to those with control shRNA (FIG. 7G) and displayed impaired ability to cause fatal AML upon xenotransplantation (FIG. 7H). Finally, we performed knockdown experiments in independent human primary AML samples and found that YTHDF2 depletion significantly decreased the clonogenic potential of AML cells in CFC assays (FIG. 7I-J). In summary, YTHDF2 is necessary for human AML cell survival and leukaemic cell engraftment.

For CFC assays shown in FIG. 7I-J, the following samples were used: 160 (AML1) (karyotype 46,XX,t(9; 11)(p22; q23),der(21; 22)(q10; q10),+der(21; 22)[cp10]; MLL-MLLT3 rearrangement; clonal evolution with add (Xp); add(4q); add(7q); +21 at relapse), 292 (AML2) (karyotype 46,XX,t(15; 17); PML-RARA rearrangement [no cyto report available]), 251 (AML3) (karyotype 46,XY,t(6; 9)(p22; q34)[9]/46,XY,der(6)t(6; 9),der(9)t(6; 9)del(9) (q21q34)[2]).

Therefore, YTHDF2 is required for human AML cell survival.

Taken together, these data indicate that the m$^6$A reader YTHDF2 is required for development and maintenance of LSCs in a mouse model of AML and is necessary for survival of human established AML cells. Our data indicate the m$^6$A reader YTHDF2 as a critical mediator of AML whose inhibition selectively compromises leukemogenesis. This suggests that YTHDF2 can be a therapeutic target in AML.

Example 13. YTHDF2 Decreases m$^6$A RNA Stability in AML

We next sought to understand the mechanism by which YTHDF2 loss impedes LSC function. YTHDF2 is known to promote transcript decay through deadenylation (Du et al. Nat Commun 7:12626, 2016; Wang et al., Nature 505:117-120, 2014). We performed gene expression analysis (as described by Ivanova et al., ibid) in Ythdf2$^{CKO}$ and Ythdf2$^{CTL}$ pre-leukemic cells. The loss of YTHDF2 resulted in deregulated gene expression with 754 upregulated and 582 downregulated genes, P<0.05) in Ythdf2$^{CKO}$ compared to Ythdf2$^{CTL}$ pre-leukemic cells (FIG. 8A). To understand which of the deregulated transcripts could be direct targets of YTHDF2, we determined transcriptome-wide mRNA m$^6$A in Ythdf2$^{CTL}$ and Ythdf2$^{CKO}$ pre-leukemic cells (as previously described (Lin et al., Mol Cell 62, 335-345, 2016)). This revealed the expected m$^6$A consensus motif as well as distribution of m$^6$A within the transcriptome and enrichment around the stop codon within transcripts in both genotypes. YTHDF2 loss is expected to result in the upregulation of direct target transcripts, indeed we observed an enrichment for m$^6$A occupancy in the significantly upregulated genes (P<0.05, 754 genes) in Ythdf2$^{CKO}$ pre-leukemic cells compared to the corresponding unchanged or downregulated gene sets (FIG. 8B). Reciprocally, we analyzed the transcriptome based on RNA m$^6$A modification and found that transcripts that contain m$^6$A show increased expression in the Ythdf2$^{CKO}$ pre-leukemic cells (FIG. 8C-D).

The upregulation of m$^6$A-containing transcripts in the absence of YTHDF2 may arise from an increase in their half-life. We therefore measured mRNA half-life transcriptome-wide in pre-leukemic cells using SLAM-seq (as previously described (Herzog et al., Nat Methods 14:1198-1204, 2017)) which revealed an overall modest increase in mRNA half-life in Ythdf2$^{CKO}$ cells (FIG. 8E). Interestingly, m$^6$A-containing transcripts displayed overall shorter half-lives compared to non-m$^6$A transcripts in Ythdf2$^{CTL}$ cells (FIG. 8F). YTHDF2 loss extended the half-life of m$^6$A-containing transcripts (FIG. 8F-G). These data indicate that m$^6$A-directed YTHDF2-mediated mRNA decay regulates the leukemic transcriptome.

Example 14. YTHDF2 Decreases Stability in Tnfrsf1b Encoding TNFR2

Inspecting m$^6$A modified transcripts that contain m$^6$A in both mouse and human AML, are upregulated in Ythdf2$^{CKO}$ LSCs we found TNF receptor 2 (TNFR2) encoded by Tnfrsf1b gene (FIG. 8H). Tnfrsf1 transcript negatively correlated with YTHDF2 expression and was highly associated with the loss of leukemogenic potential (FIG. 8I). We found that TNFRSF1B is highly methylated in mouse pre-leukemic cells and human AML cells (FIG. 8J). RIP-qPCR revealed co-precipitation of the Tnfrsf1b transcript with YTHDF2 (FIG. 8K). Concurrent with the increased half-life of Tnfrsf1b transcript (FIG. 8L), the surface expression of TNFR2 is upregulated on Ythdf2$^{CKO}$ pre-leukemic cells (FIG. 8M). We therefore tested if TNF stimulation had differential impact on Ythdf2$^{CTL}$ and Ythdf2$^{CKO}$ pre-leukemic cells. YTHDF2 loss rendered cells more sensitive to TNF-induced apoptosis (FIG. 8N). This indicates that TNFR2 upregulation may, at least in part, mediate decreased leukaemogenic capacity of YTHDF2 deficient AML cells.

Sequence Listing Notes:

SEQ ID NO: 1=YTHDF2 protein sequence (NCBI ACCESSION: NP_057342)

YTHDF2 protein (579 amino acids) consists of two key domains, namely P/Q/N-rich domain (residues 1-400) which binds CNOT (of the CCR4-NOT deadenylase complex) and the YTH domain (residues 401-579) responsible for binding to m$^6$A of m$^6$A-modified transcripts.

Residues 101-200 within the P/Q/N-rich domain of YTHDF2 are sufficient to bind CNOT (doi: 10.1038/ncomms12626).

YTHDF2 recognises m$^6$A through the aromatic cage within its YTH domain. The aromatic cage is formed by Trp432, Trp486 and Trp491 residues (doi:10.1038/cr.2014.153).

SEQ ID NO: 2=YTHDF2 transcript sequence (NCBI ACCESSION: NM_016258)

---

The invention claimed is:

1. A method for treating a hematological cancer in a patient in need thereof, comprising administering to the patient an effective amount of an YTHDF2 (YTH domain family 2) inhibitor, wherein the YTHDF2 inhibitor is a nucleic acid based inhibitor molecule selected from the group consisting of a small interfering RNA interference molecule (RNAi), an antisense oligonucleotide (ASO), and a nucleic acid aptamer.

2. The method according to claim 1, wherein the hematological cancer is selected from the group consisting of: acute myeloid leukemia (AML), chronic lymphocytic leukemia (CLL), diffuse large B-cell lymphoma (DLBCL), T-cell acute lymphoblastic leukemia (T-ALL) and B-cell acute lymphoblastic leukemia (B-ALL).

3. The method according to claim 1, wherein the cancer cells express increased levels of YTHDF2 mRNA or YTHDF2 protein relative to normal cells.

4. The method according to claim 1, wherein the nucleic acid based inhibitor molecule is a small interfering RNA interference molecule (RNAi).

5. The method according to claim 1, wherein the amount of the YTHDF2 inhibitor is effective to reduce YTHDF2 protein level, YTHDF2 function, YTHDF2 interactions with the CCR4-NOT complex or YTHDF2 interaction with m6A mRNA in a cell.

6. The method according to claim 1, wherein the YTHDF2 inhibitor is administered before, during or after chemotherapy.

7. The method according to claim 1, wherein the nucleic acid based inhibitor molecule is an antisense oligonucleotides (ASO).

* * * * *